United States Patent [19]

Wells et al.

[11] Patent Number: 5,773,411

[45] Date of Patent: Jun. 30, 1998

[54] CYCLIC COMPOUNDS LINKED BY A HETEROCYCLIC RING USEFUL AS INHIBITORS OF PLATELET GLYCOPROTEIN IIB/IIIA

[75] Inventors: Gregory James Wells, Wilmington, Del.; John Wityak, West Grove, Pa.; Anju Parthasarathy, New Castle, Del.; William Frank DeGrado, Moylan, Pa.; Sharon Anne Jackson, Chadds Ford, Pa.; Shaker Ahmed Mousa, Lincoln University, Pa.

[73] Assignee: The DuPont Merck Pharmaceutical Company, Wilmington, Del.

[21] Appl. No.: 338,977

[22] Filed: Nov. 14, 1994

Related U.S. Application Data

[63] Continuation of Ser. No. 978,475, Nov. 18, 1992, abandoned.

[51] Int. Cl.⁶ .............................. A61K 38/12; C07K 7/54
[52] U.S. Cl. .................... 514/11; 514/9; 514/2; 514/802; 530/317; 930/270; 930/DIG. 532; 930/DIG. 534; 930/DIG. 535; 930/DIG. 537
[58] Field of Search .............................. 514/9, 11, 2, 802; 530/317; 930/270, DIG. 532, DIG. 534, DIG. 535, DIG. 537

[56] References Cited

U.S. PATENT DOCUMENTS

| | | | |
|---|---|---|---|
| 4,578,079 | 3/1986 | Ruoslahti et al. | 514/18 |
| 4,614,517 | 9/1986 | Ruoslahti et al. | 514/18 |
| 4,857,508 | 8/1989 | Adams et al. | 514/18 |
| 4,952,562 | 8/1990 | Klein et al. | 514/18 |
| 5,041,380 | 8/1991 | Ruoslahti et al. | 514/18 |
| 5,192,746 | 3/1993 | Lobl et al. | 530/317 |

FOREIGN PATENT DOCUMENTS

| | | |
|---|---|---|
| 0406428 | 3/1990 | European Pat. Off. |
| 0422937 | 10/1990 | European Pat. Off. |
| 0422938 | 10/1990 | European Pat. Off. |
| 0410541 | 1/1991 | European Pat. Off. |
| 0425212 | 2/1991 | European Pat. Off. |
| 0478362 | 4/1992 | European Pat. Off. |
| 0341915 | 11/1992 | European Pat. Off. |
| 0343085 | 11/1992 | European Pat. Off. |
| 2289598 | 4/1989 | Japan. |
| 8907609 | 8/1989 | WIPO. |
| 9101331 | 2/1991 | WIPO. |
| 9104247 | 4/1991 | WIPO. |
| 9200995 | 1/1992 | WIPO. |
| 9207568 | 5/1992 | WIPO. |
| 9207870 | 5/1992 | WIPO. |

OTHER PUBLICATIONS

Cadroy et al. (1989) J. Clin. Invest. 84: 939–944.

Phillips et al. (1991) Cell 65: 359–362.

Burnier et al., in Peptides, Chemistry and Biology, Proc. 12th A.P.S., Jun. 16–21, 1991.

Davies et al, Biochemical Society Transactions, pp. 1326–1328, (1990).

Pierschbacher et al, PNAS, vol. 81, pp. 5985–5988 (Oct. 1984).

Ali et al, Peptides, Proceedings of the 11th Am. Pept. Symp., pp. 94–95 (1990).

*Primary Examiner*—Christina Y. Chan
*Assistant Examiner*—T. D. Wessendorf

[57] ABSTRACT

This invention relates to novel cyclic compounds linked by a heterocyclic ring system, which are useful as antagonists of the platelet glycoprotein IIb/IIIa complex, to pharmaceutical compositions containing such cyclic compounds, and to methods of using these compounds for the inhibition of platelet aggregation. A representative compound of the invention is cyclo-(D-Val-N(Me)Arg-Gly-Asp-[5-aminomethyl]-2-furoate).

12 Claims, No Drawings

CYCLIC COMPOUNDS LINKED BY A HETEROCYCLIC RING USEFUL AS INHIBITORS OF PLATELET GLYCOPROTEIN IIb/IIIa

This is a continuation of application Ser. No. 07/978,475 filed Nov. 18, 1992, now abandoned.

FIELD OF THE INVENTION

This invention relates to novel cyclic compounds linked by a heterocyclic ring system, which are useful as antagonists of the platelet glycoprotein IIb/IIIa complex, to pharmaceutical compositions containing such cyclic compounds, and to methods of using these compounds for the inhibition of platelet aggregation.

BACKGROUND OF THE INVENTION

Activation of platelets and the resulting platelet aggregation and secretion of factors by the platelets have been associated with different pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are known to play an essential role in the maintenance of hemostasis and in the pathogenesis of arterial thrombosis. Platelet activation has been shown to be enhanced during coronary thrombolysis which can lead to delayed reperfusion and reocclusion. Clinical studies with aspirin, ticlopidine and a monoclonal antibody for platelet glycoprotein IIb/IIIa provide biochemical evidence for platelet involvement in unstable angina, early stage of acute myocardial infarction, transient ischemic attack, cerebral ischemia, and stroke.

Platelets are activated by a wide variety of agonists resulting in platelet shape change, secretion of granular contents and aggregation. Aggregation of platelets serves to further focus clot formation by concentrating activated clotting factors in one site. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. (1991) Cell 65: 359–362. The development of a GPIIb/IIIa antagonist represents a promising new approach for antiplatelet therapy. Recent studies in man with a monoclonal antibody for GPIIb/IIIa indicate the antithrombotic benefit of a GPIIb/IIIa antagonist.

There is presently a need for a GPIIb/IIIa-specific antiplatelet agent which inhibits the activation and aggregation of platelets in response to any agonist. Such an agent should represent a more efficacious antiplatelet therapy than the currently available agonist-specific platelet inhibitors.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-containing peptides and related compounds have been reported which block fibrinogen binding and prevent the formation of platelet thrombi. For example, see Cadroy et al. (1989) J. Clin. Invest. 84: 939–944; Klein et al. U.S. Pat. No. 4,952,562, issued Aug. 28, 1990; European Patent Application EP 0319506 A; European Patent Application EP 0422938 A1; European Patent Application EP 0422937 A1; European Patent Application EP 0341915 A2; PCT Patent Application WO 89/07609; PCT Patent Application WO 90/02751; PCT Patent Application WO 91/04247; and European Patent Application EP 0343085 A1.

In the present invention we use conformationally-constraining heterocyclic ring systems as templates for cyclizing peptides such that they have high affinity and selectivity for GPIIb/IIIa.

DETAILED DESCRIPTION OF THE INVENTION

This invention is directed to novel compounds of the formula (I):

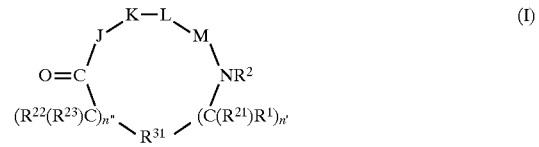

or a pharmaceutically acceptable salt or prodrug form thereof wherein:

$R^{31}$ is a 5–14 membered saturated, partially unsaturated, or aromatic heterocyclic ring system, and N-oxide forms thereof, wherein said heterocyclic ring:

contains from 1 to 4 heteroatoms selected, independently, from the group consisting of N, O and S, is substituted with 0–4 $R^{10}$;

is bonded to $(C(R^{23})R^{22})_{n''}$ and $(C(R^{21})R^1)_{n'}$ at 2 different atoms on said heterocyclic ring;

n" and n' are independently 0–3;

$R^1$ and $R^{22}$ are independently selected from the following groups:

hydrogen, $C_1$–$C_8$ alkyl substituted with 0–2 $R^{11}$, $C_2$–$C_8$ alkenyl substituted with 0–2 $R^{11}$, $C_2$–$C_8$ alkynyl substituted with 0–2 $R^{11}$, $C_3$–$C_8$ cycloalkyl substituted with 0–2 $R^{11}$, $C_6$–$C_{10}$ bicycloalkyl substituted with 0–2 $R^{11}$, aryl substituted with 0–2 $R^{12}$, a 5–10 membered heterocyclic ring system substituted with 0–2 $R^{12}$, said ring containing from 1 to 3 heteroatoms selected, independently, from the group consisting of N, O and S, =O, F, Cl, Br, I, —$CF_3$, —CN, —$CO_2R^{13}$, —C(=O)$R^{13}$, —C(=O)$NR^{13}R^{14}$, —CHO, —CH$_2$OR$^{13}$, —OC(=O)R$^{13}$, —OC(=O)OR$^{13}$, —OR$^{13}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_3$H, —SO$_2$R$^{13}$, —SR$^{13}$, —S(=O)R$^{13}$, —SO$_2$NR$^{13}$R$^{14}$, —NR$^{13}$R$^{14}$, —NHC(=NH)NHR$^{13}$, —C(=NH)NHR$^{13}$, =NOR$^{14}$, NO$_2$, —C(=O)NHOR$^{13}$, —C(=O)NHNR$^{13}$R$^{14}$, oxime, boronic acid, —OCH$_2$CO$_2$H, 2-(1-morpholino)ethoxy;

R$^1$ and R$^{21}$ can alternatively join to form a 5–7 membered carbocyclic ring substituted with 0–2 R$^{12}$;

R$^{22}$ and R$^{23}$ can alternatively join to form a 5–7 membered carbocyclic ring substituted with 0–2 R$^{12}$;

R$^1$ and R$^2$, where R$^{21}$ is H, can alternatively join to form a 5–8 membered carbocyclic ring substituted with 0–2 R$^{12}$;

R$^{11}$ is selected from one or more of the following:
=O, F, Cl, Br, I, —CF$_3$, —CN, —CO$_2$R$^{13}$, —C(=O)R$^{13}$, —C(=O)NR$^{13}$R$^{14}$, —CHO, —CH$_2$OR$^{13}$, —OC(=O)R$^{13}$, —OC(=O)OR$^{13}$, —OR$^{13}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_3$H, —SO$_2$R$^{13}$, —SR$^{13}$, —S(=O)R$^{13}$, —SO$_2$NR$^{13}$R$^{14}$, —NR$^{13}$R$^{14}$, —NHC(=NH)NHR$^{13}$, —C(=NH)NHR$^{13}$, =NOR$^{14}$, NO$_2$, —C(=O)NHOR$^{13}$, —C(=O)NHNR$^{13}$R$^{14}$, oxime, boronic acid, —OCH$_2$CO$_2$H, 2-(1-morpholino)ethoxy,
C$_1$-C$_5$ alkyl, C$_2$-C$_4$ alkenyl, C$_3$-C$_6$ cycloalkyl, C$_3$-C$_6$ cycloalkylmethyl, C$_2$-C$_6$ alkoxyalkyl, C$_3$-C$_6$ cycloalkoxy, C$_1$-C$_4$ alkyl (substituted with —NR$^{13}$R$^{14}$, —CF$_3$, NO$_2$, —SO$_2$R$^{13a}$, or —S(=O)R$^{13a}$)
aryl substituted with 0–2 R$^{12}$,
a 5–10 membered heterocyclic ring system substituted with 0–2 R$^{12}$, said ring containing from 1 to 3 heteroatoms selected, independently, from the group consisting of N, O and S, R$^{12}$ is selected from one or more of the following:
phenyl, benzyl, phenethyl, phenoxy, benzyloxy, halogen, hydroxy, nitro, cyano, C$_1$-C$_5$ alkyl, C$_3$-C$_6$ cycloalkyl, C$_3$-C$_6$ cycloalkylmethyl, C$_7$-C$_{10}$ arylalkyl, C$_1$-C$_4$ alkoxy, —CO$_2$R$^{13}$, —C(=O)NHOR$^{13}$, —C(=O)NHNR$^{13}$R$^{14}$, oxime, boronic acid, C$_3$-C$_6$ cycloalkoxy, —OC(=O)R$^{13}$, —C(=O)R$^{13}$, —OC(=O)OR$^{13}$, —OR$^{13}$, —CH$_2$OR$^{13}$, —NR$^{13}$R$^{14}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13a}$, —SO$_3$H, —SO$_2$R$^{13a}$, —S(=O)R$^{13a}$, —SR$^{13}$, —SO$_2$NR$^{13}$R$^{14}$, C$_2$-C$_6$ alkoxyalkyl, C$_1$-C$_4$ hydroxyalkyl, methylenedioxy, ethylenedioxy, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, —OCH$_2$CO$_2$H, 2-(1-morpholino)ethoxy, C$_1$-C$_4$ alkyl (substituted with —NR$^{13}$R$^{14}$, —CF$_3$, NO$_2$, or —S(=O)R$^{13a}$);

R$^{13}$ is H, C$_1$-C$_7$ alkyl, aryl, —(C$_1$-C$_6$ alkyl)aryl, or C$_3$-C$_6$ alkoxyalkyl;

R$^{13a}$ is C$_1$-C$_7$ alkyl, aryl, —(C$_1$-C$_6$ alkyl)aryl, or C$_3$-C$_6$ alkoxyalkyl;

R$^{14}$ is OH, H, C$_1$-C$_4$ alkyl, or benzyl;

R$^{21}$ and R$^{23}$ are independently selected from:
hydrogen;
C$_1$-C$_4$ alkyl, optionally substituted with halogen;
C$_1$-C$_2$ alkoxy;
benzyl;

R$^2$ is H or C$_1$-C$_8$ alkyl;

R$^{10}$ is selected from one or more of the following:
hydrogen phenyl, benzyl, phenethyl, phenoxy, benzyloxy, halogen, hydroxy, nitro, cyano, C$_1$-C$_8$ alkyl, C$_3$-C$_6$ cycloalkyl, C$_3$-C$_6$ cycloalkylmethyl, C$_7$-C$_{10}$ arylalkyl, C$_1$-C$_4$ alkoxy, —CO$_2$R$^{13}$, —C(=O)NHOR$^{13}$, —C(=O)NHNR$^{13}$R$^{14}$, oxime, boronic acid, C$_3$-C$_6$ cycloalkoxy, —OC(=O)R$^{13}$, —C(=O)R$^{13}$, —OC(=O)OR$^{13}$, —OR$^{13}$, —CH$_2$OR$^{13}$, —NR$^{13}$R$^{14}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13a}$, —SO$_3$H, —SO$_2$R$^{13a}$, —S(=O)R$^{13a}$, —SR$^{13}$, —SO$_2$NR$^{13}$R$^{14}$, C$_2$-C$_6$ alkoxyalkyl, C$_1$-C$_4$ hydroxyalkyl, methylenedioxy, ethylenedioxy, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, —OCH$_2$CO$_2$H, 2-(1-morpholino)ethoxy, C$_1$-C$_4$ alkyl (substituted with —NR$^{13}$R$^{14}$, —CF$_3$, NO$_2$, or —S(=O)R$^{13a}$), =O;

J is b-Ala or an L-isomer or D-isomer amino acid of structure —N(R$^3$)C(R$^4$)(R$^5$)C(=O)—, wherein:
R$^3$ is H or C$_1$-C$_8$ alkyl;
R$^4$ is H or C$_1$-C$_3$ alkyl;
R$^5$ hydrogen,
C$_1$-C$_8$ alkyl substituted with 0–2 R$^{11}$,
C$_2$-C$_8$ alkenyl substituted with 0–2 R$^{11}$,
C$_2$-C$_8$ alkynyl substituted with 0–2 R$^{11}$,
C$_3$-C$_8$ cycloalkyl substituted with 0–2 R$^{11}$,
C$_6$-C$_{10}$ bicycloalkyl substituted with 0–2 R$^{11}$,
aryl substituted with 0–2 R$^{12}$,
a 5–10 membered heterocyclic ring system substituted with 0–2 R$^{12}$, said ring containing from 1 to 3 heteroatoms selected, independently, from the group consisting of N, O and S,
=O, F, Cl, Br, I, —CF$_3$, —CN, —CO$_2$R$^{13}$, —C(=O)R$^{13}$, —C(=O)NR$^{13}$R$^{14}$, —CH$_2$OR$^{13}$, —OC(=O)R$^{13}$, —OC(=O)OR$^{13}$, —OR$^{13}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13a}$, —SO$_3$H, —SO$_2$R$^{13a}$, —SR$^{13}$, —S(=O)R$^{13a}$, —SO$_2$NR$^{13}$R$^4$, —NR$^{13}$R$^{14}$, —NHC(=NH)NHR$^{13}$, —C(=NH)NHR$^{13}$, =NOR$^{14}$, N$_2$, —C(=O)NHOR$^{13}$, —C(=O)NHNR$^{13}$R$^{14}$, oxime, boronic acid, —OCH$_2$CO$_2$H, 2-(1-morpholino)ethoxy, —SC(=NH)NHR$^{13}$, N$_3$, —Si(CH$_3$)$_3$, (C$_1$-C$_5$ alkyl)NHR$^{16}$;
—(C$_0$-C$_6$ alkyl)X;

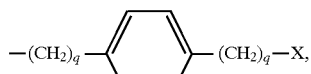

where q is independently 0,1;

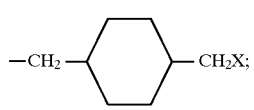

—(CH$_2$)$_m$S(CH$_2$)$_2$X, where m=1,2;

wherein X is defined below; and
R³ and R⁴ may also be taken together to form $$-CH_2CHCH_2-,\quad \overset{|}{(CH_2)_nX}$$

where
n=0,1 and X is $$-NH-C\overset{\displaystyle NR^{13}}{\underset{\displaystyle N(R^{13})R^{13}}{\diagup\!\!\!\diagdown}};$$

R³ and R⁵ can also be taken together to form —(CH$_2$)$_t$— (t=2–4) or —CH$_2$SC(CH$_3$)$_2$—; or R⁴ and R⁵ can also be taken together to form —(CH$_2$)$_u$—, where u=2–5;

R¹⁶ is selected from:
  an amine protecting group;
  1-2 amino acids;
  1-2 amino acids substituted with an amine protecting group;

K is a D-isomer or L-isomer amino acid of structure —N(R⁶)CH(R⁷)C(=O)—, wherein:
  R⁶ is H or C$_1$–C$_8$ alkyl;
  R⁷ is selected from:
    —(C$_1$–C$_7$ alkyl)X;

$$-(CH_2)_q-\!\!\!\left\langle\!\!\!\bigcirc\!\!\!\right\rangle\!\!\!-(CH_2)_q-X,$$

where q is independently 0,1;

$$-CH_2-\!\!\!\left\langle\!\!\!\bigcirc\!\!\!\right\rangle\!\!\!-CH_2X;$$

—(C$_1$–C$_6$ alkyl)—[bicyclic NH group]$_{0-3}$

—(CH$_2$)$_m$O—(C$_1$–C$_4$ alkyl)—X, where m=1,2;
(CH$_2$)$_m$S—(C$_1$–C$_4$ alkyl)—X, where m=1,2; and X is selected from:

$$-NH-C\overset{\displaystyle NR^{13}}{\underset{\displaystyle N(R^{13})R^{13}}{\diagup\!\!\!\diagdown}},$$

—N(R¹³)R¹³, —C(=NH)(NH$_2$), —SC(NH)—NH$_2$;

R⁶ and R⁷ may also be taken together to form $$-CH_2CHCH_2-,\quad \overset{|}{(CH_2)_nX}$$

where $$-NH-C\overset{\displaystyle NR^{13}}{\underset{\displaystyle N(R^{13})R^{13}}{\diagup\!\!\!\diagdown}};$$

n=0,1 and X is
L is —Y(CH$_2$)$_v$C(=O)—, wherein:
  Y is NH, N(C$_1$–C$_3$ alkyl), O, or S; and v=1,2;
M is a D-isomer or L-isomer amino acid of structure —NR¹⁷—CH(R⁸)C(=O)—, wherein:
  R¹⁷ is H, C$_1$–C$_3$ alkyl;
  R⁸ is —CH$_2$CO$_2$R¹³, —CH$_2$SO$_3$R¹³ᵃ, —CH(CH$_3$)CO$_2$R¹³, —SO$_2$NR¹³R¹⁴, —CH$_2$-boronic acid, —CH$_2$-tetrazole, —NHSO$_2$CF$_3$, —CONHNHSO$_2$CF$_3$, —PO(OR¹³)$_2$, —PO(OR¹³)R¹³, —CONHOR¹³, —SO$_2$NH-heteroaryl, —CH$_2$SO$_2$NH-heteroaryl, —SO$_2$NHCOR¹³, —CH$_2$SO$_2$NHCOR¹³, —CONHSO$_2$R¹³ᵃ, —CH$_2$CONHSO$_2$R¹³ᵃ, —NHSO$_2$NHCOR¹³ᵃ, —NHCONHSO$_2$R¹³, —SO$_2$NHCONR¹³.

This invention includes those compounds above of the formula:

$$\begin{array}{c} K-L \\ J \diagup \quad \diagdown M \\ O=C \quad \quad NR^2 \\ (R^{22}(R^{23})C)_{n''} \diagdown \quad \diagup (C(R^{21})R^1)_{n'} \\ R^{31} \end{array}$$

or a pharmaceutically acceptable salt or prodrug form thereof wherein:

R³¹ is a 5–14 membered saturated, partially unsaturated, or aromatic heterocyclic ring system, and N-oxide forms thereof, wherein said heterocyclic ring:
  contains from 1 to 4 heteroatoms selected, independently, from the group consisting of N, O and S;
  is substituted with 0–4 R¹⁰;
  is bonded to (C(R²³)R²²)$_{n''}$ and (C(R²¹)R¹)$_{n'}$ at 2 different atoms on said heterocyclic ring;

n" and n' are independently 0–3;

R¹ and R²² are independently selected from the following groups:
  hydrogen,
  C$_1$–C$_8$ alkyl substituted with 0–2 R¹¹,
  C$_2$–C$_8$ alkenyl substituted with 0–2 R¹¹,
  C$_2$–C$_8$ alkynyl substituted with 0–2 R¹¹,
  C$_3$–C$_8$ cycloalkyl substituted with 0–2 R¹¹,
  C$_6$–C$_{10}$ bicycloalkyl substituted with 0–2 R¹¹,
  aryl substituted with 0–2 R¹²,
  a 5–10 membered heterocyclic ring system substituted with 0–2 R¹², said ring containing from 1 to 3 heteroatoms selected, independently, from the group consisting of N, O and S,
  =O, F, Cl, Br, I, —CN, —CO$_2$R¹³, —C(=O)R¹³, —C(=O)NR¹³R¹⁴, —CHO, —CH$_2$OR¹³, —OC(=O)R¹³, —OC(=O)OR¹³, —OR¹³, —OC(=O)NR¹³R¹⁴, —NR¹⁴C(=O)R¹³, —NR¹⁴C(=O)OR¹³, —NR¹³C(=O)NR¹³R¹⁴, —NR¹⁴SO$_2$NR¹³R¹⁴, —NR¹⁴SO$_2$R¹³ᵃ, —SO$_3$H, —SO$_2$R¹³ᵃ, —SR¹³, —S(=O)R¹³ᵃ, —SO$_2$NR¹³R¹⁴, —CH$_2$NR¹³R¹⁴, —NR¹³R¹⁴, —NHC(=NH)NHR¹³, —C(=NH)NHR¹³, NO$_2$;

R¹ and R²¹ can alternatively join to form a 5–7 membered carbocyclic ring substituted with 0–2 R¹²;

$R^{22}$ and $R^{23}$ can alternatively join to form a 5–7 membered carbocyclic ring substituted with 0–2 $R^{12}$;

$R^1$ and $R^2$, where $R^{21}$ is H, can alternatively join to form a 5–8 membered carbocyclic ring substituted with 0–2 $R^{12}$;

$R^{11}$ is selected from one or more of the following:
=O, F, Cl, Br, I, —CF$_3$, —CN, —CO$_2$R$^{13}$, —C(=O)R$^{13}$, —C(=O)NR$^{13}$R$^{14}$, —CH$_2$OR$^{13}$, —OC(=O)R$^{13}$, —OC(=O)OR$^{13}$, —OR$^{13}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13a}$, —SO$_3$H, SO$_2$R$^{13a}$, —SR$^{13}$, —S(=O)R$^{13a}$, —SO$_2$NR$^{13}$R$^{14}$, —CH$_2$NR$^{13}$R$^{14}$, —NR$^{13}$R$^{14}$, —NHC(=NH)NHR$^{13}$, —C(=NH)NHR$^{13}$, =NOR$^{14}$, NO$_2$, C$_1$–C$_5$ alkyl, C$_2$–C$_4$ alkenyl, C$_3$–C$_6$ cycloalkyl, C$_3$–C$_6$ cycloalkylmethyl, C$_2$–C$_6$ alkoxyalkyl, C$_1$–C$_4$ alkyl (substituted with —NR$^{13}$R$^{14}$, —CF$_3$, NO$_2$, —SO$_2$R$^{13}$, or —S(=O) R$^{13a}$)

aryl substituted with 0–2 $R^{12}$, a 5–10 membered heterocyclic ring system substituted with 0–2 $R^{12}$, said ring containing from 1 to 3 heteroatoms selected, independently, from the group consisting of N, O and S, $R^{12}$ is selected from one or more of the following:
phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_7$–C$_{10}$ arylalkyl, C$_1$–C$_4$ alkoxy, —CO$_2$R$^{13}$, hydroxamic acid, hydrazide, oxime, boronic acid, sulfonamide, formyl, C$_3$–C$_6$ cycloalkoxy, —OC(=O)R$^{13}$, —C(=O)R$^{13}$, —OC(=O)OR$^{13}$, —OR$^{13}$, —CH$_2$OR$^{13}$, —NR$^{13}$R$^{14}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13a}$, —SO$_3$H, —SO$_2$R$^{13a}$, —S(=O)R$^{13a}$, —SR$^{13}$, —SO$_2$NR$^{13}$R$^{14}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, C$_1$–C$_4$ alkyl (substituted with —NR$^{13}$R$^{14}$, —CF$_3$, NO$_2$, or —S(=O)R$^{13a}$);

$R^{13}$ is H, C$_1$–C$_7$ alkyl, aryl, —(C$_1$–C$_6$ alkyl)aryl, or C$_3$–C$_6$ alkoxyalkyl;

$R^{14}$ is OH, H, C$_1$–C$_4$ alkyl, or benzyl;

$R^{21}$ and $R^{23}$ are independently selected from:
hydrogen;
C$_1$–C$_4$ alkyl, optionally substituted with halogen;
C$_1$–C$_2$ alkoxy;
benzyl;

$R^2$ is H or C$_1$–C$_8$ alkyl;

$R^{10}$ is selected from one or more of the following:
phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_7$–C$_{10}$ arylalkyl, C$_1$–C$_4$ alkoxy, —CO$_2$R$^{13}$, hydroxamic acid, hydrazide, oxime, boronic acid, sulfonamide, formyl, C$_3$–C$_6$ cycloalkoxy, —OC(=O)R$^{13}$, —C(=O)R$^{13}$, —OC(=O)OR$^{13}$, —OR$^{13}$, —CH$_2$OR$^{13}$, —NR$^{13}$R$^{14}$, —OC(=O)NR$^{13}$R$^{14}$, —NR$^{14}$C(=O)R$^{13}$, —NR$^{14}$C(=O)OR$^{13}$, —NR$^{13}$C(=O)NR$^{13}$R$^{14}$, —NR$^{14}$SO$_2$NR$^{13}$R$^{14}$, —NR$^{14}$SO$_2$R$^{13a}$, —SO$_3$H, —SO$_2$R$^{13a}$, —S(=O)R$^{13a}$, —SR$^{13}$, —SO$_2$NR$^{13}$R$^{14}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, C$_1$–C$_4$ alkyl (substituted with —NR$^{13}$R$^{14}$, —CF$_3$, NO$_2$, or —S(=O)R$^{13a}$), =O;

J is b-Ala or an L-isomer or D-isomer amino acid of structure —N(R$^3$)C(R$^4$)(R$^5$)C(=O)—, wherein:
$R^3$ is H or CH$_3$;
$R^4$ is H or C$_1$–C$_3$ alkyl;
$R^5$ is H, C$_1$–C$_8$ alkyl, C$_3$–C$_6$ cycloalkyl, C$_3$–C$_6$ cycloalkylmethyl, C$_1$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, (CH$_2$)$_s$NHC(=NH)(NH$_2$), (CH$_2$)$_s$NHR$^{16}$, where s=3–5;
$R^3$ and $R^5$ can be taken together to form —(CH$_2$)$_t$—(t=2–4) or —CH$_2$SC(CH$_3$)$_2$—; or
$R^4$ and $R^5$ can be taken together to form —(CH$_2$)$_u$—, where u=2–5;
$R^{16}$ is selected from:
an amine protecting group;
1-2 amino acids;
1-2 amino acids substituted with an amine protecting group;

K is a D-isomer or L-isomer amino acid of structure —N(R$^6$)CH(R$^7$)C(=O)—, wherein:
$R^6$ is H or C$_1$–C$_8$ alkyl;
$R^7$ is selected from:
—(C$_1$–C$_7$ alkyl)X;

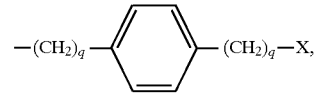

where q is independently 0,1;

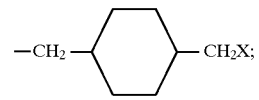

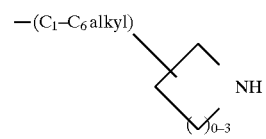

—(CH$_2$)$_m$O—(C$_1$–C$_4$ alkyl)—X, where m=1,2;
—(CH$_2$)$_m$S—(C$_1$–C$_4$ alkyl)—X, where m=1,2; and
X is selected from:

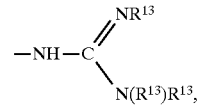

—N(R$^{13}$)R$^{13}$, —C(=NH)(NH$_2$), —SC(NH)—NH$_2$;
$R^6$ and $R^7$ may also be taken together to form

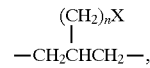

where n=0,1 and X is

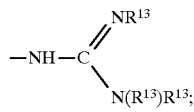

L is —Y(CH$_2$)$_v$C(=O)—, wherein:
Y is NH, N(C$_1$-C$_3$ alkyl), O, or S; and v=1,2;
M is a D-isomer or L-isomer amino acid of structure —NR$^{17}$—CH(R$^8$)C(=O)—, wherein:
R$^{17}$ is H, C$_1$-C$_3$ alkyl;
R$^8$ is —CH$_2$CO$_2$R$^{13}$, —CH$_2$SO$_3$R$^{13a}$, —CH(CH$_3$)CO$_2$R$^{13}$, —SO$_2$NR$^{13}$R$^{14}$, —CH$_2$-boronic acid, or —CH$_2$-tetrazole.

Included in the present invention are those compounds above, wherein:
K=NMeArg.

Included in the present invention are those compounds above, wherein:
n" is 0 and n' is 0;
n" is 0 and n' is 1;
n" is 0 and n' is 2;
n" is 0 and n' is 3;
n" is 1 and n' is 0;
n" is 1 and n' is 1;
n" is 1 and n' is 2;
n" is 1 and n' is 3.
n" is 2 and n' is 0;
n" is 2 and n' is 1;
n" is 2 and n' is 2; or
n" is 2 and n' is 3.

Included in the present invention are those compounds above, wherein:
R$^{31}$ is selected from the group, and N-oxide forms thereof, consisting of:
(a) a 5 membered saturated, partially unsaturated or aromatic monocyclic heterocyclic ring containing 1–3 heteroatoms selected independently from nitrogen, sulfur, or oxygen atom, and containing 0–3 nitrogen, 0–1 sulfur, and 0–1 oxygen atoms, said heterocyclic ring being substituted with 0–2 R$^{10}$;
(b) a 6 membered saturated, partially unsaturated or aromatic monocyclic heterocyclic ring containing 1–3 heteroatoms selected independently from nitrogen, sulfur, or oxygen atom, and containing 0–3 nitrogen, 0–1 sulfur, and 0–1 oxygen atoms, said heterocyclic ring being substituted with 0–2 R$^{10}$;
(c) a 8–11 membered saturated, partially unsaturated or aromatic monocyclic or bicyclic heterocycle containing 1–4 heteroatoms selected independently from nitrogen, sulfur, or oxygen atom, and containing 0–4 nitrogen, 0–2 sulfur, and 0–2 oxygen atoms, said heterocycle being substituted with 0–2 R$^{10}$; or
(d) a 11–14 membered saturated, partially unsaturated, or aromatic fused bicyclic or tricyclic heterocycle containing 1–4 heteroatoms selected independently from nitrogen, sulfur, or oxygen atom, and containing 0–4 nitrogen, 0–2 sulfur, and 0–2 oxygen atoms, said heterocycle being substituted with 0–2 R$^{10}$.

The present invention includes those compounds of formula (I) described above wherein:
R$^{31}$ is a 5, 6, 8, 9, or 10 membered saturated, partially saturated, or aromatic heterocycle, and N-oxide forms thereof, selected from the group consisting of:

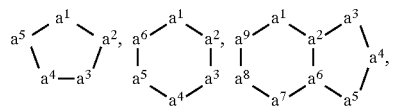

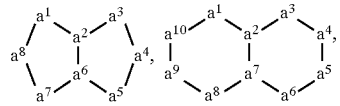

wherein:
any of the bonds forming the heterocycle may be a single or double bond;
a$^1$, a$^2$, a$^3$, a$^4$, a$^5$, a$^6$, a$^7$, a$^8$, a$^9$, and a$^{10}$ are independently selected from N, S, O, or CH;
provided that:
said heterocycle contains 1–4 heteroatoms selected independently from nitrogen, oxygen, or sulfur; and
said heterocycle contains 0–3 nitrogen, 0–1 oxygen, and 0–1 sulfur; and
the bonds to (C(R$^{23}$)R$^{22}$)$_{n"}$ and to (C(R$^{21}$)R$^1$)$_{n'}$ are to any two different carbon atoms on the heterocycle;
wherein said heterocycle is substituted with 0–2 R$^{10}$.

The present invention includes those compounds of formula (I) described above wherein:
R$^{31}$ is a 11, 13, or 14 membered saturated, partially saturated, or aromatic heterocycle, and N-oxide forms thereof, selected from the group consisting of:

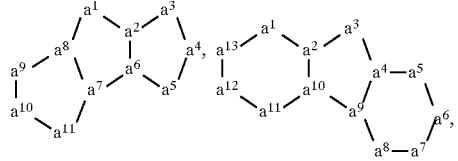

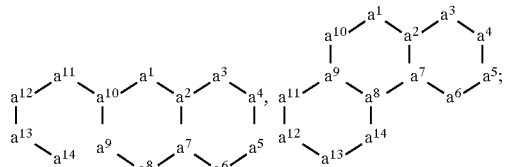

wherein:
any of the bonds forming the heterocyclic ring may be a single or double bond;
a$^1$ through a$^{14}$ are independently selected from N, S, O, or CH;
provided that:
said heterocycle contains 1–4 heteroatoms selected independently from nitrogen, oxygen, or sulfur; and
said heterocycle contains 0–3 nitrogen, 0–1 oxygen, and 0–1 sulfur; and
the bonds to (C(R$^{23}$)R$^{22}$)$_{n"}$ and to (C(R$^{21}$)R$^1$)$_{n'}$ are to any two different carbon atoms on the heterocycle;
wherein said heterocycle is substituted with 0–2 R$^{10}$.

The present invention includes those compounds of formula (I) described above wherein:
R$^{31}$ is a 5, 6, or 10 membered saturated, partially saturated, or aromatic heterocycle, and N-oxide forms thereof, selected from the group consisting of (the bonds to f(C(R$^{23}$)R$^{22}$)$_{n"}$ and to (C(R$^{21}$)R$^1$)$_{n'}$ are shown):

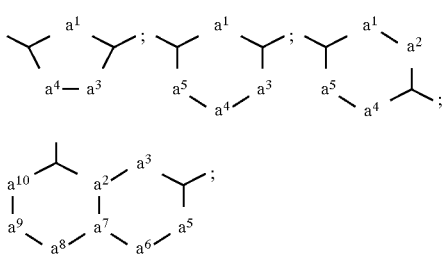

wherein:
any of the bonds forming the heterocyclic ring may be a single or double bond;
$a^1$ through $a^{10}$ are independently selected from N, S, O, or CH;
provided that:
said heterocycle contains 1–3 heteroatoms selected independently from N, S, or O; and
said heterocycle contains 0–3 nitrogen, 0–1 oxygen, and 0–1 sulfur; and
wherein said heterocycle is substituted with 0–2 $R^{10}$.

The present invention includes those compounds of formula (I) described above wherein:
$R^{31}$ is a 5 membered aromatic heterocycle, and N-oxide forms thereof, which is (the bonds to $(C(R^{23})R^{22})_{n''}$ and to $(C(R^{21})R^1)_{n'}$ are shown)

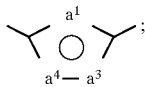

wherein:
$a^1$, $a^3$, and $a^4$ are independently selected from N, S, O, or CH;
provided that:
said heterocycle contains 1–3 heteroatoms independently selected from nitrogen, oxygen, or sulfur; and
said heterocycle contains 0–3 nitrogen, 0–1 oxygen, and 0–1 sulfur; and
wherein said heterocycle is substituted with 0–2 $R^{10}$.

The present invention includes those compounds of formula (I) described above wherein:
$R^{31}$ is a 6 or 10 membered aromatic heterocycle, and N-oxide forms thereof, selected from the group consisting of (the bonds to $(C(R^{23})R^{22})_{n''}$ and to $(C(R^{21})R^1)_{n'}$ are shown):

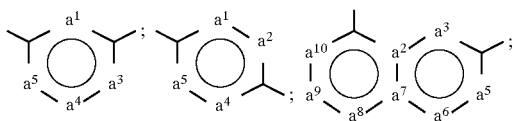

wherein:
$a^1$ through $a^{10}$ are independently selected from N or CH;
provided that said heterocycle contains 1–3 nitrogen; and
wherein said heterocycle is substituted with 0–2 $R^{10}$.

This invention includes those compounds described above, wherein:
$R^{31}$ is a 5 or 6 membered aromatic heterocycle, $(C(R^{23})R^{22})_{n''}$ and $(C(R^{21})R^1)_{n'}$ being bonded in a 1,3-fashion to atoms on said heterocyclic ring heterocycle, said heterocycle being substituted with 0–2 $R^{10}$, said heterocycle being selected from the group consisting of: furan, thiophene, pyrrole, imidazole, pyrazole, oxazole, isoxazole, thiazole, isothiazole, 1,2,4-triazole, 1,2,4-oxazole, 1,3,4-oxazole, 1,2,4-thiazole, 1,3,4-thiazole, pyridine, pyridazine, pyrimidine, pyrazine, 1,2,3-, 1,2,4- and 1,3,5-triazine, and N-oxide forms thereof.

This invention includes those compounds described above, including a pharmaceutically acceptable salt or prodrug form thereof wherein:
n" is 0 or 1;
n' is 0–2.
$R^1$ and $R^{22}$ are independently selected from H, $C_1$–$C_4$ alkyl, phenyl, benzyl, phenyl-$(C_2$–$C_4)$alkyl, $C_1$–$C_4$ alkoxy;
$R^{21}$ and $R^{23}$ are independently H or $C_1$–$C_4$ alkyl;
$R^2$ is H or $C_1$–$C_8$ alkyl;
$R^{10}$ is H, $C_1$–$C_8$ alkyl, phenyl, halogen, or $C_1$–$C_4$ alkoxy;
J is b-Ala or an L-isomer or D-isomer amino acid of structure —N($R^3$)C($R^4$)($R^5$)C(=O)—, wherein:
$R^3$ is H or $CH_3$;
$R^4$ is H or $C_1$–$C_3$ alkyl;
$R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sX$ where X is —$NH_2$ or —NHC(=NH)($NH_2$) and s=3–5; or
$R^3$ and $R^5$ can be taken together to form —$(CH_2)_t$— (t =2–4) or —$CH_2SC(CH_3)_2$—;or
$R^4$ and $R^5$ can be taken together to form —$(CH_2)_u$—, where u=2–5;
K is an L-isomer amino acid of structure —N($R^6$)CH($R^7$)C(=O)—, wherein:
$R^6$ is H or $C_1$–$C_8$ alkyl;
$R^7$ is —$(CH_2)_p$NHC(=NH)($NH_2$), where p=3–5;

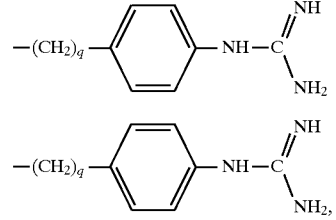

where q=0,1; —$(CH_2)_rX$, where r=4–6;

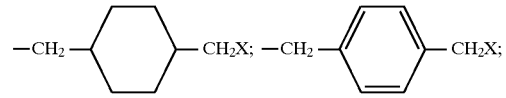

—$(CH_2)_mS(CH_2)_2X$, where m=1,2;
—$(C_3$–$C_7$ alkyl)—N—$(C_1$–$C_6$ alkyl)

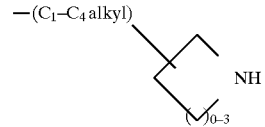

—$(CH_2)_m$—O—$(C_1$–$C_4$ alkyl)—NH—$(C_1$–$C_6$ alkyl), where m=1,2;
—$(CH_2)_m$—S—$(C_1$–$C_4$ alkyl)—NH—$(C_1$–$C_6$ alkyl), where m=1,2; and
X is —$NH_2$ or —NHC(=NH)($NH_2$); or R⁶ and R⁷ are taken together to form

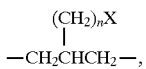

where n=0,1 and X is —NHC(=NH) (NH₂);
L is —Y(CH₂)ᵥC(=O)—, wherein:
  Y is NH, O, or S; and v=1,2;
M is an L-isomer amino acid of structure —NH—CH(R⁸)C(=O)—, wherein:
  R⁸ is —CH₂CO₂H, —CH₂SO₃H, or —CH(CH₃)CO₂H.

The present invention includes those compounds described above wherein:
n″ is 0;
n′ is 1
R²¹ is H;
R¹ is H, C₁–C₄ alkyl, phenyl, benzyl, or phenyl-(C₁–C₄) alkyl;
R² is H or methyl;
J is b-Ala or an L-isomer or D-isomer amino acid of structure —N(R³)C(R⁴) (R⁵)C(=O)—, wherein:
  R³ is H or CH₃;
  R⁴ is H or C₁–C₃ alkyl;
  R⁵ is H, C₁–C₈ alkyl, C₃–C₆ cycloalkyl, C₃–C₆ cycloalkylmethyl, C₁–C₆ cycloalkylethyl, phenyl, phenylmethyl, CH₂OH, CH₂SH, CH₂OCH₃, CH₂SCH₃, CH₂CH₂SCH₃, (CH₂)ₛX where X is NH₂ or NHC(=NH) (NH₂) and s=3–5; or
  R³ and R⁵ can be taken together to form —CH₂CH₂CH₂—; or
  R⁴ and R⁵ can be taken together to form —(CH₂)ᵤ—, where u=2–5;
K is an L-isomer amino acid of structure —N(R⁶)CH(R⁷)C(=O)—, wherein:
  R⁶ is H or C₁–C₈ alkyl;
  R⁷ is —(CH₂)ₚNHC(=NH) (NH₂), where p=3–5;

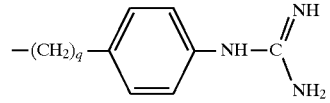

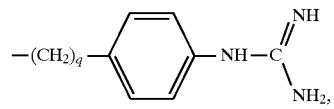

where q=0,1;
—(CH₂)ᵣX, where r=4–6;

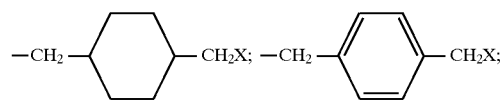

—(CH₂)ₘS(CH₂)₂X, where m=1,2;
—(C₃–C₇ alkyl)—N—(C₁–C₆ alkyl)

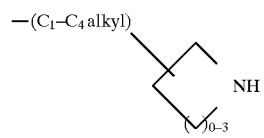

—(CH₂)ₘ—O—(C₁–C₄ alkyl)—NH—(C₁–C₆ alkyl), where m=1,2;

—(CH₂)ₘ—S—(C₁–C₄ alkyl)—NH—(C₁–C₆ alkyl), where m=1,2; and
X is —NH₂ or —NHC(=NH) (NH₂), provided that X is not —NH₂ when r=4; or
R⁶ and R⁷ are taken together to form

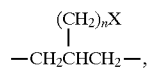

where n=0,1 and X is —NHC(=NH) (NH₂);
L is —Y(CH₂)ᵥC(=O)—, wherein:
  Y is NH, O, or S; and v=1,2;
M is an L-isomer amino acid of structure —NH—CH(R⁸)C(=O)—, wherein:
  R⁸ is —CH₂CO₂H, —CH₂SO₃H, or —CH(CH₃)CO₂H.

The present invention includes those compounds above wherein:
n″ is 0;
n′ is 1;
R²¹ is H;
R¹ is H, C₁–C₄ alkyl, phenyl, benzyl, or phenyl-(C₂–C₄) alkyl;
R² is H or methyl;
J is b-Ala or an L-isomer or D-isomer amino acid of structure —N(R³)C(R⁴)(R⁵)C(=O)—, wherein:
  R³ is H or CH₃;
  R⁴ is H;
  R⁵ is H, C₁–C₈ alkyl, C₃–C₆ cycloalkyl, C₃–C₆ cycloalkylmethyl, C₁–C₆ cycloalkylethyl, phenyl, phenylmethyl, CH₂OH, CH₂SH, CH₂OCH₃, CH₂SCH₃, CH₂CH₂SCH₃, (CH₂)ₛX where X is NH₂ or NHC(=NH) (NH₂) and s=3,4,5; or
  R³ and R⁵ can be taken together to form —CH₂CH₂CH₂—;
K is an L-isomer amino acid of structure —N(R⁶)CH(R⁷)C(=O)—, wherein:
  R⁶ is H or C₃–C₈ alkyl;
  R⁷ is —(CH₂)ₚNHC(=NH) (NH₂), where p=3–4;

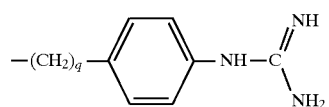

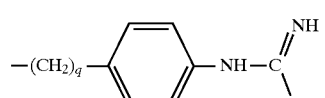

where q=0,1;
—(CH₂)ᵣX, where r=4–6;

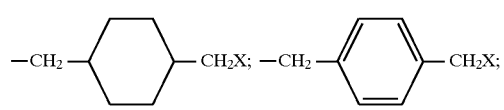

—(CH₂)ₘS(CH₂)₂X, where m=1,2;

—(C$_4$-C$_7$ alkyl)—N—(C$_1$-C$_6$ alkyl)

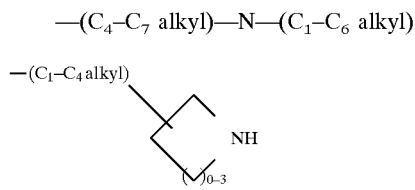

—(CH$_2$)$_m$—O—(C$_1$-C$_4$ alkyl)—NH—(C$_1$-C$_6$ alkyl), where m=1,2;
—(CH$_2$)$_m$—S—(C$_1$-C$_4$ alkyl)—NH—(C$_1$-C$_6$ alkyl), where m=1,2; and X is —NH$_2$ or —NHC(=NH)(NH$_2$), provided that X is not —NH$_2$ when r=4; or L is —YCH$_2$C(=O)—, wherein:
  Y is NH or O;

M is an L-isomer amino acid of structure —NH—CH(R$^8$)C(=O)—, wherein:
  R$^8$ is —CH$_2$CO$_2$H or —CH$_2$SO$_3$H.

The present invention includes those compounds above wherein:
  n" is 0;
  n' is 1;
  R$^{21}$ is H;
  R$^1$ is H;
  R$^2$ is H;

J is b-Ala or an L-isomer or D-isomer amino acid of formula —N(R$^3$)CH(R$^5$)C(=O)—, wherein:
  R$^3$ is H and R$^5$ is H, CH$_3$, CH$_2$CH$_3$, CH(CH$_3$)$_2$, CH(CH$_3$)CH$_2$CH$_3$, CH$_2$CH$_2$CH$_3$, CH$_2$CH$_2$CH$_2$CH$_3$, CH$_2$CH$_2$SCH$_3$, CH$_2$CH(CH$_3$)$_2$, (CH$_2$)$_4$NH$_2$; or
  R$^3$ is CH$_3$ and R$^5$ is H; or
  R$^3$ and R$^5$ can be taken together to form —CH$_2$CH$_2$CH$_2$—.

K is an L-isomer amino acid of formula —N(CH$_3$)CH(R$^7$)C(=O)—, wherein:
  R$^7$ is —(CH$_2$)$_3$NHC(=NH)(NH$_2$);

L is —NHCH$_2$C(=O)—; and

M is an L-isomer amino acid of formula —NHCH(CH$_2$COOH)C(=O)—.

The present invention includes those compounds above wherein:
  n" is 0;
  n' is 1;
  R$^{21}$ is H;
  R$^{10}$ is selected from H, halogen;
  R$^1$ and R$^2$ are independently selected from H, methyl;
  J is selected from D-Val, D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala;
  K is selected from NMeArg, Arg;
  L is selected from Gly, β-Ala, Ala;
  M is selected from Asp, αMeAsp, βMeAsp, NMeAsp, D-Asp;
  n" is 0–1;
  n' is 0–3.

In the present invention it has been discovered that the compounds above are useful as inhibitors of glycoprotein IIb/IIIa (GPIIb/IIIa). As discussed above, GPIIb/IIIa mediates the process of platelet activation and aggregation. The compounds of the present invention inhibit the activation and aggregation of platelets induced by all known endogenous platelet agonists.

The present invention also provides methods for the treatment of conditions involving platelet activation and aggregation, including cardiovascular and cerebrovascular thromboembolic disorders, including, for example, thromboembolic disorders associated with unstable angina, myocardial infarction, transient ischemic attack, stroke, atherosclerosis, and diabetes, by administering to a host in need of such treatment a pharmaceutically effective amount of the compounds described above. The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

The compounds of the present invention can also be co-administered with suitable anti-coagulant agents, such as heparin or warfarin, or anti-platelet agents, such as aspirin. The compounds of the present invention may also be combined with thrombolytic or fibrinolytic agents, such as plasminogen activators, anistreplase, urokinase, or streptokinase, to achieve synergistic effects in the treatment of thromboembolic disorders.

GPIIb/IIIa is known to be overexpressed in metastatic tumor cells. The compounds of the present invention may also be useful for the treatment of metastatic cancer.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. Two distinct isomers (cis and trans) of the peptide bond are known to occur; both can also be present in the compounds described herein, and all such stable isomers are contemplated in the present invention. Unless otherwise specifically noted, the L-isomer of the amino acid is used at positions J, K, L, and M of the compounds of the present invention. The D and L-isomers of a particular amino acid are designated herein using the conventional 3-letter abbreviation of the amino acid, as indicated by the following examples: D-Leu, D-Leu, L-Leu, or L-Leu.

When any variable (for example, R$^1$, R$^{10}$, R$^{11}$, R$^{12}$, R$^{21}$, R$^{22}$, R$^{23}$, m, n, p, X, Y, etc.) occurs more than one time in any constituent or in any formula, its definition on each occurrence is independent of its definition at every other occurrence. Thus, for example, if a group is shown to be substituted with 0–3 R$^{11}$, then said group may optionally be substituted with up to three R$^{11}$ and R$^{11}$ at each occurrence is selected independently from the defined list of possible R$^{11}$.

Combinations of substituents and/or variables in a chemical structure are permissible only if such combinations result in stable compounds.

When a bond to a substituent is shown to cross the bond connecting two atoms in a ring, then such substituent may be bonded to any atom on the ring.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "bicycloalkyl" is intended to include saturated bicyclic ring groups such as [3.3.0]

bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like. "Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated (i.e., partially saturated), or aromatic. Examples of such carbocyles include, but are not limited to cyclopentyl, cyclohexyl, phenyl, biphenyl, naphthyl, indanyl or tetrahydronaphthyl (tetralin).

As used herein, the term "heterocycle" or "heterocyclic ring system" is intended to mean a stable 5 to 14 membered monocyclic, bicyclic, or tricyclic heterocyclic ring which may be saturated, partially unsaturated (i.e. partially saturated), or aromatic, and which consists of carbon atoms and from 1 to 4 heteroatoms selected, independently, from the group consisting of N, O and S and wherein the nitrogen and sulfur heteroatoms may optionally be oxidized, and the nitrogen may optionally be quaternized, and including any heterocyclic ring system in which any of the above-defined heterocyclic rings is fused to a benzene ring. Unless specifically specified otherwise, the heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofurane, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H,6H-1,5, 2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4- oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperidine, piperazine, indoline, isoindoline, quinuclidine, or morpholine. Also included are fused ring and spiro compounds containing, for example, the above heterocycles.

By "stable compound" or "stable structure" is meant herein a compound that is sufficiently robust to survive isolation to a useful degree of purity from a reaction mixture, and formulation into an efficacious therapeutic agent.

The term "substituted", as used herein, means that an one or more hydrogen on the designated atom is replaced with a selection from the indicated group, provided that the designated atom's normal valency is not exceeded, and that the substitution results in a stable compound.

As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to: mineral or organic acid salts of basic residues such as amines; alkali or organic salts of acidic residues such as carboxylic acids; esters of carboxylates; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The term "amino acid" as used herein means an organic compound containing both a basic amino group and an acidic carboxyl group. Included within this term are modified and unusual amino acids,such as those disclosed in, for example, Roberts and Vellaccio (1983) *The Peptides*, 5: 342–429, the teaching of which is hereby incorporated by reference.

The term "amino acid residue" as used herein means that portion of an amino acid (as defined herein) that is present in a peptide or pseudopeptide. The term "peptide" as used herein means a linear compound that consists of two or more amino acids (as defined herein) that are linked by means of peptide or pseudopeptide bonds.

The compounds of the present invention can be prepared in a number of ways well known to one skilled in the art of organic synthesis. Preferred methods include but are not limited to those methods described below.

The following abbreviations are used herein:

| | |
|---|---|
| D-Abu | D-2-aminobutyric acid |
| β-Ala or βAla | 3-aminopropionic acid |
| Boc | t-butyloxycarbonyl |
| Boc-iodo-Mamb | t-butyloxycarbonyl-3-aminomethyl-4-iodobenzoic acid |
| Boc-Mamb | t-butyloxycarbonyl-3-aminomethylbenzoic acid |
| Boc-ON | [2-(tert-butyloxycarbonyloxylimino)-2-phenylacetonitrile |
| $Cl_2Bzl$ | dichlorobenzyl |
| CBZ | carbobenzyloxy |
| DCC | dicyclohexylcarbodiimide |
| DIEA | diisopropylethylamine |
| di-NMeOrn | N-αMe-N-γMe-ornithine |
| DMAP | 4-dimethylaminopyridine |
| HBTU | 2-(1H-Benzotriazol-1-yl)-1,1,3,3-tetramethyluronium hexafluorophosphate |
| NMeArg or MeArg | α-N-methyl arginine |
| NMeAmf | N-Methylaminomethylphenylalanine |
| NMeAsp | α-N-methyl aspartic acid |
| NMeGly or MeGly | N-methyl glycine |
| NMe-Mamb | N-methyl-3-aminomethylbenzoic acid |
| NMM | N-methylmorpholine |
| OcHex | O-cyclohexyl |
| OBzl | O-benzyl |
| TBTU | 2-(1H-Benzotriazol-1-yl)-1,1,3,3-tetramethyluronium tetrafluoroborate |
| Tos | tosyl |

The following conventional three-letter amino acid abbreviations are used herein; the conventional one-letter amino acid abbreviations are not used herein:

Ala=alanine
Arg=arginine
Asn=asparagine
Asp=aspartic acid
Cys=cysteine
Gln=glutamine
Glu=glutamic acid
Gly=glycine
His=histidine
Ile=isoleucine
Leu=leucine
Lys=lysine
Met=methionine
Nle=norleucine
Phe=phenylalanine
Phg=phenylglycine
Pro=proline
Ser=serine
Thr=threonine
Trp=tryptophan
Tyr=tyrosine
Val=valine

Peptide Synthesis

The compounds of the present invention can be synthesized using standard synthetic methods known to those skilled in the art. Generally, peptides are elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference. The compounds of the invention may also be synthesized using automated peptide synthesizing equipment. In addition to the foregoing, procedures for peptide synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Sythesis" Springer-Verlag, New York (1984), the disclosures of which are hereby incorporated by reference.

The coupling between two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference.

The α-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) J. Org. Chem. 45, 1295–1300) chloro or bromomethyl resin, hydroxymethyl resin, and aminomethyl resin. Many of these resins are commercially available with the desired C-terminal amino acid already incorporated.

The α-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred α-amino protecting group is either Boc or Fmoc. Many amino acid derivatives suitably protected for peptide synthesis are commercially available.

The α-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-identified groups. Those skilled in the art will appreciate that the selection and use of appropriate protecting groups for these side chain functionalities will depend upon the amino acid and presence of other protecting groups in the peptide. The selection of such a protecting group is important in that it must not be removed during the deprotection and coupling of the α-amino group.

For example, when Boc is chosen for the α-amine protection the following protecting groups are acceptable: p-toluenesulfonyl (tosyl) moieties and nitro for arginine; benzyloxycarbonyl, substituted benzyloxycarbonyls, or tosyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the α-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation and cyclization of the peptide is completed all of the protecting groups are removed. For the liquid phase synthesis the protecting groups are removed in whatever manner as dictated by the choice of protecting groups. These procedures are well known to those skilled in the art.

When a solid phase synthesis is used, the peptide should be removed from the resin without simultaneously removing protecting groups from functional groups that might interfere with the cyclization process. Thus, if the peptide is to be cyclized in solution, the cleavage conditions need to be chosen such that a free α-carboxylate and a free α-amino group are generated without simultaneously removing other protecting groups. Alternatively, the peptide may be removed from the resin by hydrazinolysis, and then coupled by the azide method. Another very convenient method involves the synthesis of peptides on an oxime resin, followed by intramolecular nucleophilic displacement from the resin, which generates a cyclic peptide (Osapay, Profit, and Taylor (1990) Tetrahedron Letters 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide can also be accomplished by other acid reagents such as trifluoromethanesulfonic acid/ trifluoroacetic acid mixtures.

Unusual amino acids used in this invention can be synthesized by standard methods familiar to those skilled in the art ("The Peptides: Analysis, Sythesis, Biology, Vol. 5, pp. 342–449, Academic Press, New York (1981)). N-Alkyl amino acids can be prepared using procedures described in previously (Cheung et al., (1977) Can. J. Chem. 55, 906; Freidinger et all, (1982) J. Org. Chem. 48, 77 (1982)), which are incorporated here by reference.

The compounds of the present invention may be prepared using the procedures further detailed below.

Representative materials and methods that may be used in preparing the compounds of the invention are described further below.

Manual solid phase peptide synthesis was performed in 25 mL polypropylene filtration tubes purchased from BioRad Inc. Oxime resin (substitution level=0.96 mmol/g) was prepared according to published procedures (DeGrado and Kaiser (1980) J. Org. Chem. 45, 1295). All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 3-cyanobenzoic acid and [2-(tert-butyloxycarbonyloxylimino)-phenylacetonitrile] (Boc-ON) were purchased from Aldrich Chemical Company. Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were purchased from EM Science. Palladium on carbon catalyst (10% Pd) was purchased from Fluka Chemical Company. Absolute ethanol was obtained from Quantum Chemical Corporation. Thin layer chromatography (TLC) was performed on Silica Gel 60 $F_{254}$ TLC plates (layer thickness 0.2 mm) which were purchased from EM Separations. TLC visualization was accomplished using UV light, iodine, and/or ninhydrin spray. Melting points were determined using a Thomas Hoover or Electrothermal 9200 melting point apparatus and are uncorrected. HPLC analyses were performed on either a HEWLETT PACKARD 1090, WATERS DELTA PREP 3000, RAININ, or DUPONT 8800 system. NMR spectra were recorded on a 300 MHz GENERAL ELECTRIC QE-300, VARIAN 300, or VARIAN 400 spectrometer. Fast atom bombardment mass spectrometry (FAB-MS) was performed on a VG ZAB-E double-focusing mass spectrometer using a XENON FAB gun as the ion source or a FINNIGAN MAT 8230.

Synthesis of Compounds of the Invention

The novel compounds of Formula (I) may be prepared using the reactions and techniques described in this section.

The reactions are performed in a solvent appropriate to the reagents and employed and suitable for the transformation being effected. It is understood by those skilled in the art of organic synthesis that the functionality present on the heterocycle and other portions of the molecule must be consistent with the chemical transformations proposed. This will frequently necessitate judgment as to the order of synthetic steps, protecting groups required, deprotection conditions, and activation groups required for synthesis of peptide bonds. Throughout the following section, not all compounds of Formula (I) falling into a given class may necessarily be prepared by all methods described for that class. Substituents on the starting materials or intermediates may be incompatible with some of the reaction conditions required in some of the methods described. Such restrictions to the substituents which are incompatible with the reaction conditions will be readily apparent to one skilled in the art and alternative methods described in the literature must then be used.

The following schemes describe routes to the variously claimed heterocyclic linkers possessing aminomethyl and carboxylic acid (or ester) functionalities which are 1,3-disposed on the ring system. Further incorporation of the amino acid residues leading to the final targeted cyclic peptide can be accomplished using the methods described in copending commonly assigned U.S. patent application U.S. Ser. No. 07/949,285, filed Sep. 9, 1992, abandoned. Representative examples of the fully elaborated cyclic peptides are described in the experimental section below.

1) Five-Membered Heterocyclics

Table 1 lists representative five-membered aromatic heterocycles $R^{31}$ groups of the compound of the invention.

TABLE 1

Five-membered Aromatic Heterocyclic $R^{31}$ Groups

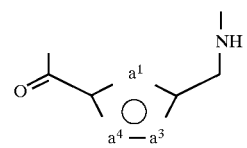

| Scheme No. | Intermediate Compound Number | Class | $a^1$ | $a^3$ | $a^4$ |
|---|---|---|---|---|---|
| 1 | I | furan | O | CH | CH |
| 2 | II | furan | CH | CH | O |
| 3 | III | furan | CH | O | CH |
| 4 | IV | thiophene | S | CH | CH |
| 5, 6 | V | thiophene | CH | S | CH |
| 5, 6 | VI | thiophene | CH | CH | S |
| 7, 8 | VII | imidazole | N(H) | N(H) | CH |
| 9 | VIII | imidazole | N(H) | CH | N(H) |
| 10 | IX | pyrrole | CH | CH | NH |
| 11 | X | pyrrole | NH | CH | CH |
| 12 | XI | pyrrole | CH | NH | CH |
| 13 | XII | pyrazole | CH | N(H) | N(H) |
| 14 | XIII | 1,2,4-triazole | N(H) | N(H) | N(H) |
| 15 | XIV | oxazole | N | O | CH |
| 16 | XV | oxazole | O | CH | N |
| 17 | XVI | thiazole | S | N | CH |
| 18, 19 | XVII | thiazole | S | CH | N |
| 20 | XVIII | isoxazole | CH | N | O |
| 20 | XIX | isoxazole | CH | O | N |
| 21 | XX | isothiazole | CH | N | S |
| 21 | XXI | isothiazole | CH | S | N |
| 22 | XXII | 1,2,4-oxadiazole | N | N | O |
| 23 | XXIII | 1,2,4-oxadiazole | N | O | N |
| 24 | XXIV | 1,2,4-thiadiazole | N | N | S |
| 25 | XXV | 1,2,4-thiadiazole | N | S | N |
| 26 | XXVI | 1,3,4-oxadiazole | O | N | N |
| 27 | XXVII | 1,3,4-thiadiazole | S | N | N | a) Furans

Synthesis of the 2,5-substituted linker (I) could be accomplished starting with an oxidative esterification (Corey, *J. Amer. Chem. Soc.*, 1968, 90. 5616) of the commercially available 5-methylfurfural (Scheme 1). The resulting methyl 5-methyl-2-furoic acid is then carefully monobrominated with NBS at room temperature, using VAZO® 52 as the initiator. Treatment of this benzylic-like bromide with sodium azide in a dipolar aprotic solvent, such as DMF or DMSO, provides the corresponding azido compound which is catalytically reduced in the presence of hydrochloric acid to give methyl 5-aminomethyl-2-furoate hydrochloride (I).

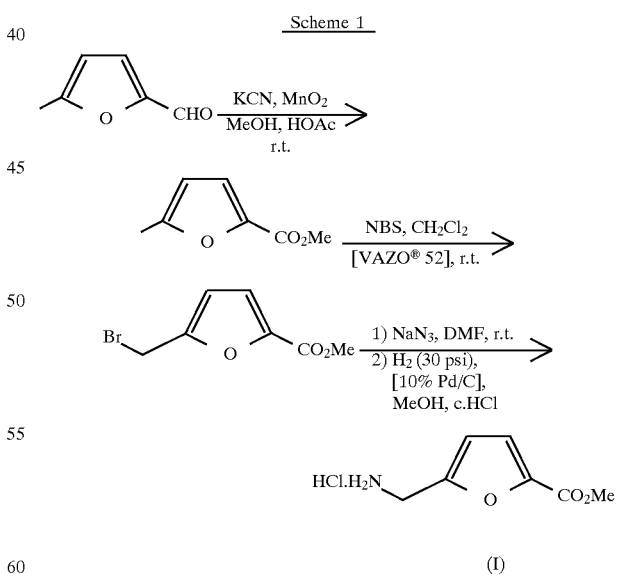

Synthesis of the corresponding 2,4-substituted isomer could be accomplished by using a similar approach starting with 4-methylfurfural (Chadwick, *J. Chem. Soc., Perkin Trans. I*, 1973, 2327, 2329) as shown by Scheme 2.

Scheme 2

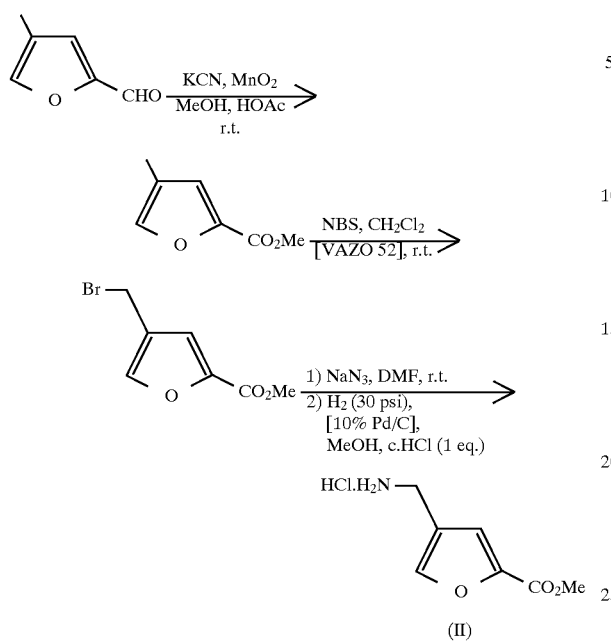

Analogously, the 3,5-isomeric linker (III) can be approached starting from 2-methyl-4-furaldedyde (Kotsuki, *Chem. Lett.* 1983, 7, 1007) using the same strategy (Scheme 3).

Scheme 3

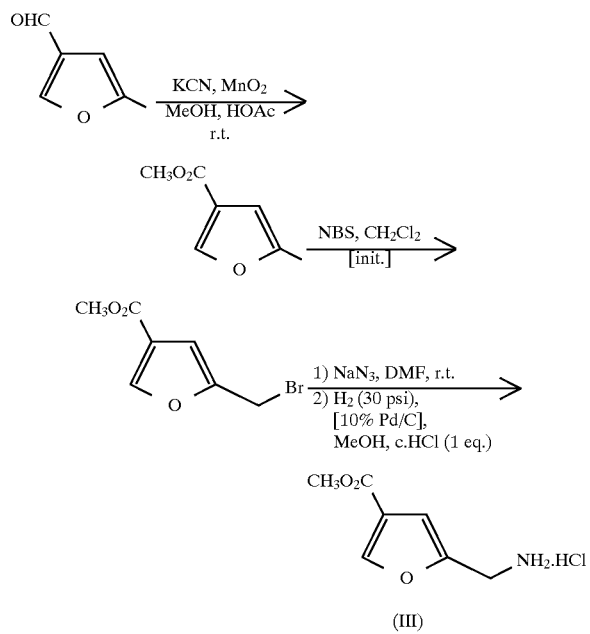

b) Thiophenes

Synthesis of 5-aminomethyl-2-thiophenecarboxylic acid hydrochloride can be accomplished starting from 5-methyl-2-thiophenecarboxylic acid (Rinker, Recl. Trav. Chim. Pays Bas, 1933, 52, 538, 546; Paal, Chem Ber. 1885, 18, 2253) using the same general strategy described above for the furan linkers, as shown by Scheme 4.

Scheme 4

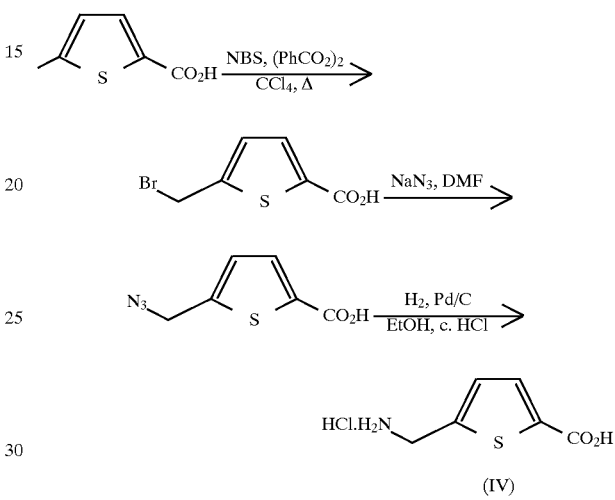

Access to the 4,2- and 5,3- linker species may be gained through a common starting material, 3-bromo-5-methylthiophene (Gronowitz, Holm, *Acta. Chem. Scand.* (B), 1976, 36, 505; Gronowitz, *Adv. Het. Chem.*, 1963, 1, 1).

Thus, as shown by Scheme 5, oxidation of the methyl group to the carboxylic acid, followed by its protection as the oxazoline (Meyers, *Tetrahedron Lett.*, 1989, 3303), lithiation of the bromide followed by treatment with Katritzky's benzotriazolephosphazene reagent (*Tetrahedron Lett.*, 1989, 3303), subsequent treatment with ammonium hydroxide, and finally acid deprotection leads to 3-(aminomethyl)thiophene-5-carboxylic acid (V).

Alternatively, initial lithiation of 3-bromo-5-methylthiophene followed by capture with methyl chloroformate gives methyl 5-methylthiophene-3-carboxylate. Free-radical bromination of the methyl group followed by treatment with an alkali azide, subsequent reduction and hydrolysis provides 5-(aminomethyl)thiophene-3-carboxylic acid (VI).

Scheme 5

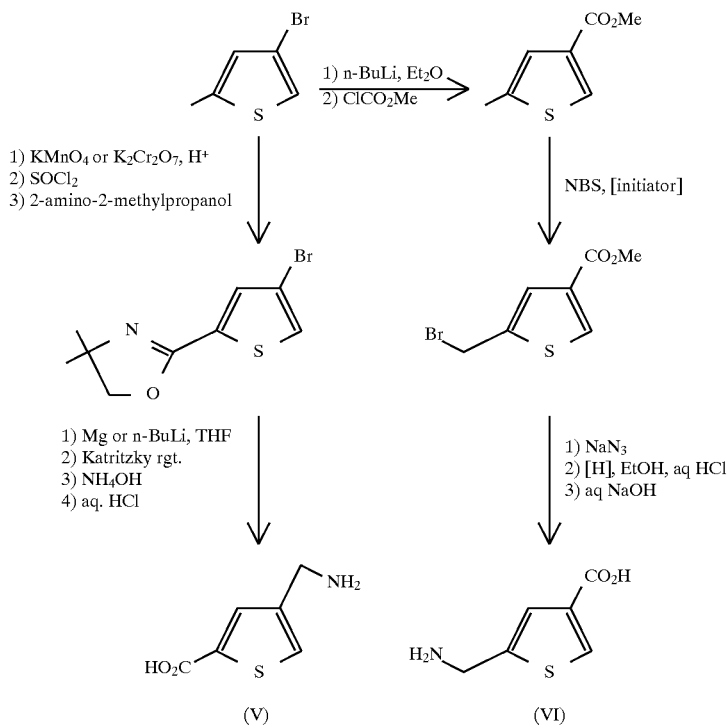

These same linkers, V and VI, may also be prepared from 3-methylthiophene. As shown in Scheme 6, Vilsmeier formylation of this compound (Newkome, Paudler, "Contemporary Heterocyclic Chemistry", Wiley-Interscience, N.Y., 1982; p.155) leads to both the 2- and 5-formyl isomers. The minor product, 2-formyl-4-methylthiophene, can be carried through to either linker species: oxidation of the aldehyde to the ester (Corey procedure) and conversion of methyl to aminomethyl, as described previously, gives methyl 4-(aminomethyl)thiophene-2-carboxylate hydrochloride (V). Alternatively, oximation of the aldehyde followed by dehydration ($Ac_2O$) to the nitrile and subsequent oxidation of methyl to carboxylic acid gives, following reduction of the nitrile to aminomethyl, 5-(aminomethyl)thiophene-3-carboxylic acid (VI).

Scheme 6

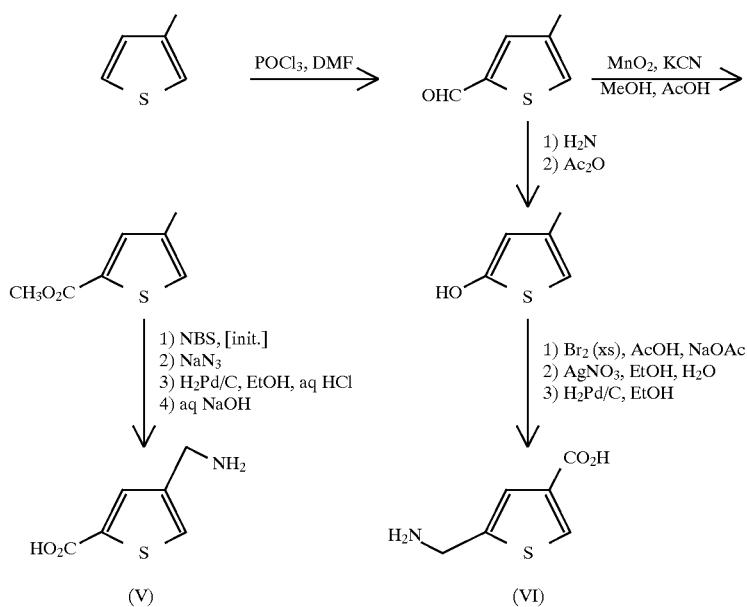

c) Imidazoles

An approach to the 2-(aminomethyl)-4(5)-imidazolecarboxylic acid (VII) is shown in Scheme 7. Treatment of the of the tosyl-protected aminoacetonitrile with anhydrous hydrogen chloride in ethanol gives the corresponding imido ester, as previously described (Mengelburg, Chem. Ber.,1954, 87. 1425). Conversion of this imidate into 2-(N-tosyl-aminomethyl)-4(5)-(hydroxymethyl)-imidazole can be accomplished with 1,3-dihydroxy-acetone dimer in anhydrous ammonia at about 70° C. in an autoclave. Sequential oxidation of the hydroxymethyl group to the aldehyde with MnO₂ followed by further oxidation to the corresponding ester, as described earlier above, and final deprotection and hydrolysis of the tosyl and ester groups leads to the targetted linker (VII).

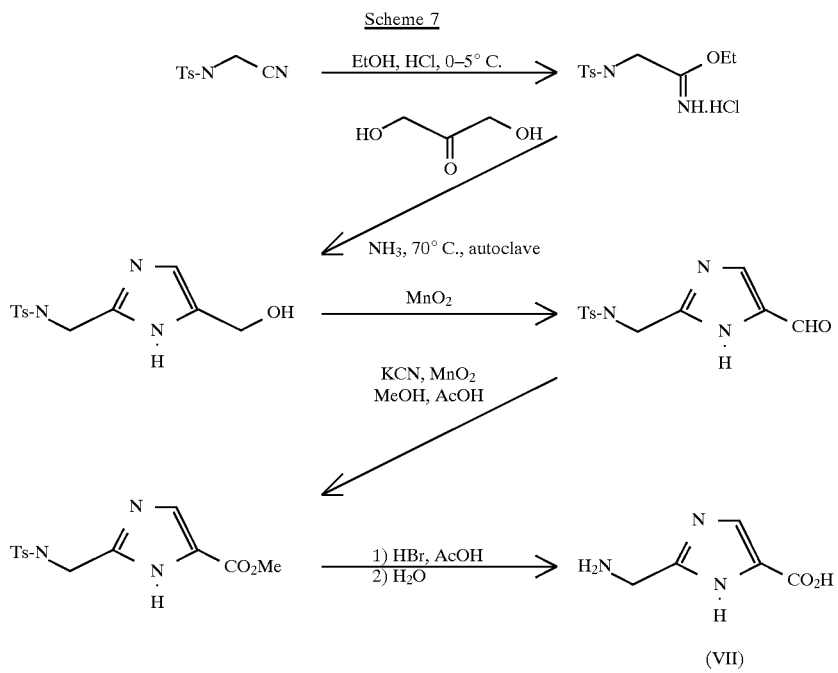

An alternative approach to this linker type is shown in Scheme 8 starting with 2-methylimidazole-4(5)-carboxylic acid (Fargher, J. Chem. Soc., 1919, 115, 235; Gemgross, Chem. Ber. 1912, 45, 525). Esterification followed by free-radical bromination (and consequential ring bromination) leads to methyl 2-(bromomethyl)-4-bromoimidazole-5-carboxylate. Displacement of the bromine at the 2-position with azide followed by catalytic reduction (and consequential reduction of the bromine at the 4-position) gives the desired linker (VII).

Scheme 8

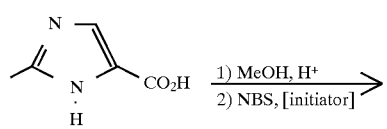

-continued
Scheme 8

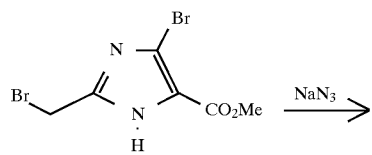

-continued
Scheme 8

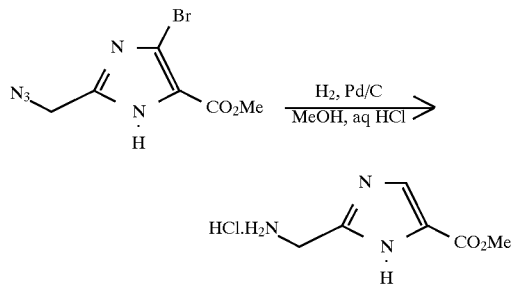

Synthesis of the isomeric imidazole linker, methyl 4(5)-(aminomethyl)imidazole-2-carboxylate hydrochloride (VIII) can be carried out using the strategy outlined in Scheme 9. Commercially available 4(5)-(hydroxymethyl) imidazole is protected as the N,O-(bis)tritylated species. Alternatively, other base-stable protecting groups may be employed (eg. TMS-, TBDMS-, Ts-). Formation of the 2-lithio intermediate with n-BuLi (or LDA), followed by quenching with methyl chloroformate and hydrolytic workup leads to methyl 4(5)-(hydroxymethyl)imidazole-2-carboxylate. The hydroxymethyl group is transformed into the aminomethyl group by conversion to the chloride or tosylate, displacement with azide (NaN$_3$, DMF) and finally reduction to the amine (H$_2$, Pd/C, methanol, aq HCl ), as previously described.

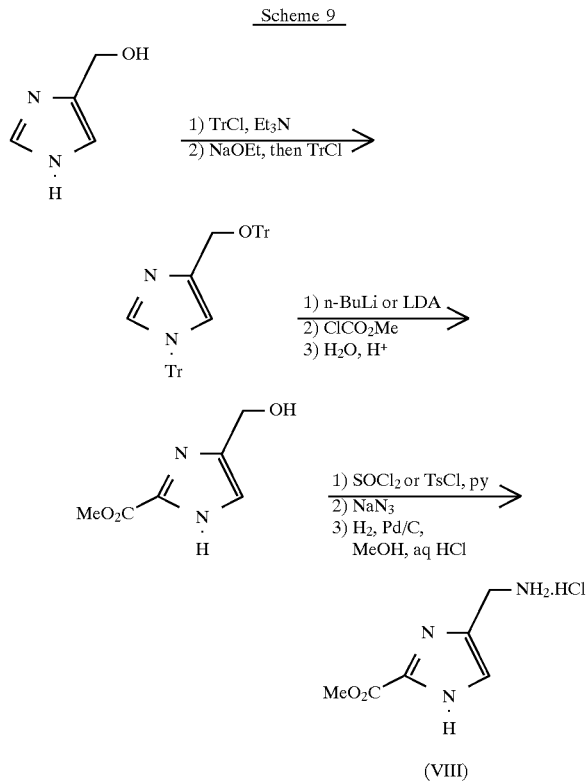

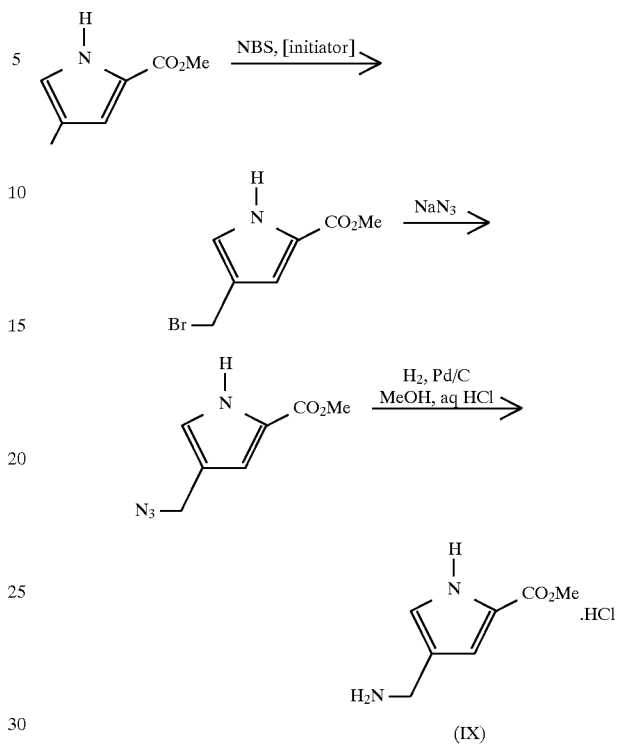

d) Pyrroles

Synthesis of methyl 4-(aminomethyl)pyrrole-2-carboxylate hydrochloride (IX) starts with methyl 4-methylpyrrole-2-carboxylate (Rapoport, *J. Org. Chem.*, 1964, 29, 2727). In similar fashion to several of the cases described above, the methyl group is converted to aminomethyl via free-radical halogenation, displacement with azide, and reduction as illustrated by Scheme 10.

Preparation of methyl 5-(aminomethyl)pyrrole-2-carboxylate hydrochloride (X) can be accomplished by the approach shown in Scheme 11. A three-step conversion of pyrrole into methyl 5-formylpyrrole-2-carboxylate has been described (*Org. Syn.*, Coll Vol. 4, 1963, p831). Alternatively, Muchowski (*Tetrahedron Lett.*, 1988, 29, 777) has described the bis(dimethylamino)azafulvene dimer resulting from treatment of 2-formylpyrrole with dimethylamine. Such species may be lithiated at low temperatures and captured with a variety of electrophiles, including methyl chloroformate, to also give methyl 5-formylpyrrole-2-carboxylate. The aldehyde group is then converted to the oxime under standard conditions and finally reduced by catalytic hydrogenation in the presence of hydrochloric acid to give the target linker (X).

Scheme 11

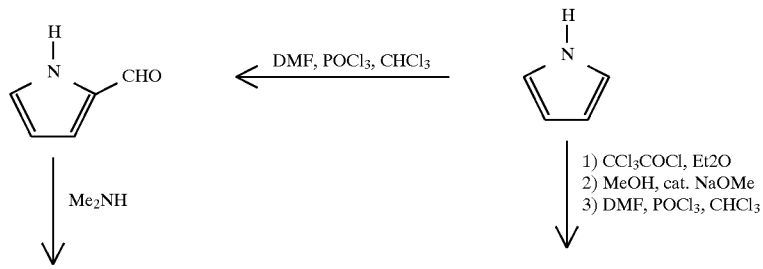

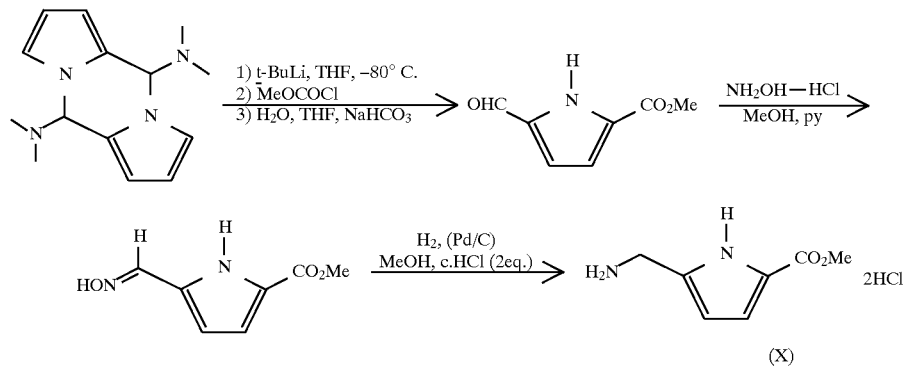

(X)

The third possible linker in the pyrrole cases, methyl 5-(aminomethyl)pyrrole-3-carboxylate hydrochloride (XI) can be prepared according to Scheme 12. Starting with methyl 5-methylpyrrole-3-carboxylate (Jones, *J. Amer. Chem. Soc.*, 1955, 77, 4069, 4072), the methyl group is converted into the amino methyl group as previously described above.

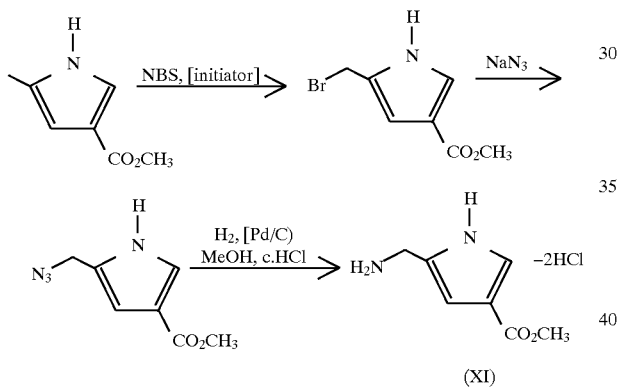

(XI)

e) Pyrazole

Preparation of 5-(aminomethyl)pyrazole-3-carboxylic acid (XII) may be approached by the methods outlined in Scheme 13. Treatment of acetylacetone with hydrazine followed by selective oxidation of one of the two methyl groups of the resulting 3,5-dimethylpyrazole gives 5-methyl-pyrazole-3-carboxylic acid (Rothenburg, *Chem. Ber.*, 1894, 27, 1097). Alternatively, this compound may be prepared in one step by treatment of commercially available 2,4-dioxovaleric acid with hydrazine. The methyl group may then be converted to aminomethyl as previously described.

Alternatively, in the event of unwanted ring bromination during treatment with NBS, one may make use of ethyl 5-(benzoyloxy)-2,4-dioxo-valerate (Tschesche, *Chem. Ber.*, 1958, 91, 2074, 2079) to prepare an hydroxymethyl-substituted pyrazole intermediate which may then be transformed into an aminomethyl group by standard methods (Scheme 13).

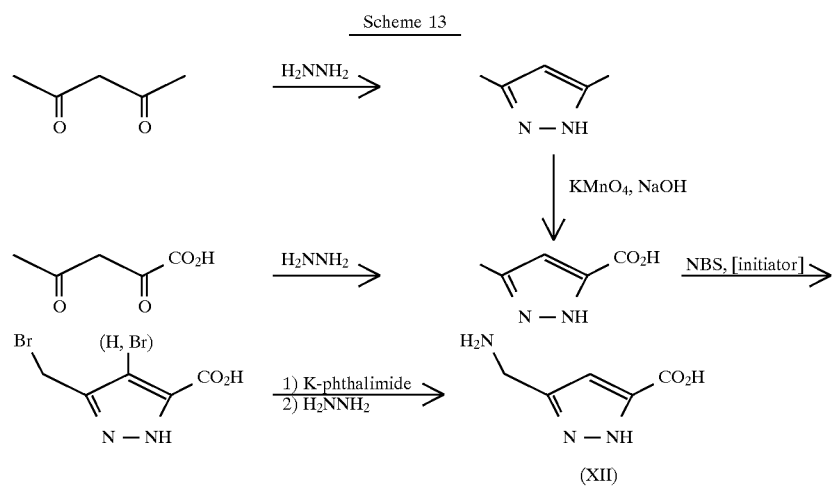

(XII)

-continued
Scheme 13

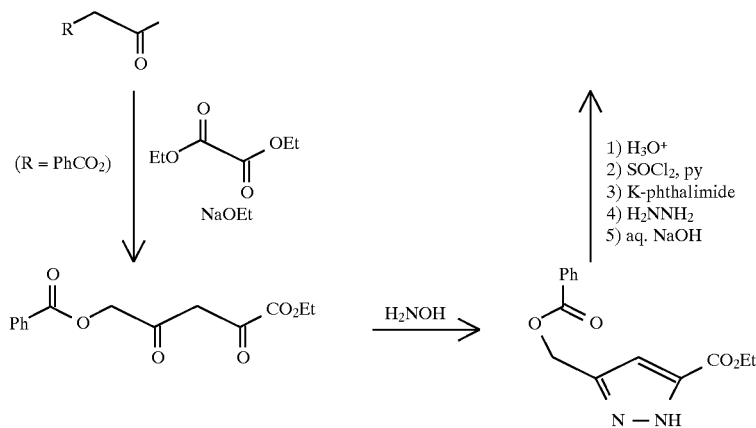

f) 1,2,4-Triazole

Synthesis of methyl 5-(aminomethyl)-1,2,4-triazole-3-carboxylate (XIII) can be accomplished using the approach shown in Scheme 14. The key intermediate, 3-(hydroxymethyl)- 5-methyl-1,2,4-triazole, can be prepared according to the method of Francis (*Tetrahedron Lett.,* 1987, 28, 5133) whereby hydroxyacetylhydrazide is condensed with acetamidine under base catalyzed conditions followed by thermolytic ring closure. The synthesis then proceeds in a similar fashion to some of the previously described linkers above in which the aldehyde is oxidatively esterified using Corey's procedure and the methyl group converted to aminomethyl via the bromide and azide intermediates.

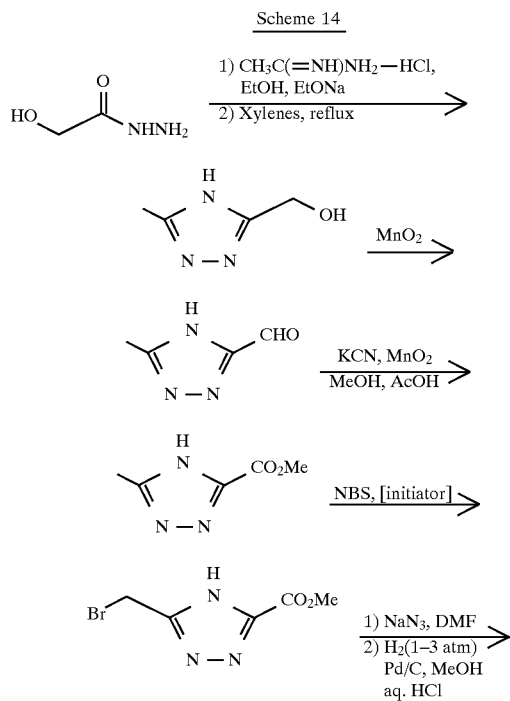

-continued
Scheme 14

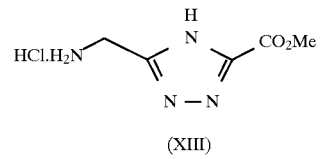

(XIII)

g) Oxazoles

Yokokawa (*Synthetic Lett.,* 1992, 2, 153) has recently described the preparation and cyclization of N-acylserine ester derivatives to give 2-substituted-4,5-dihydrooxazole-4-carboxylate esters which, after oxidation, give the corresponding 2-substituted-oxazole-4-carboxylate esters. By inference, N-acylation of serine methyl ester with N-phthaloylglycine, followed by cyclization, oxidation, and deprotection, should give methyl 2-(aminomethyl)oxazole-4-carboxylate (XIV), as outlined in Scheme 15 below.

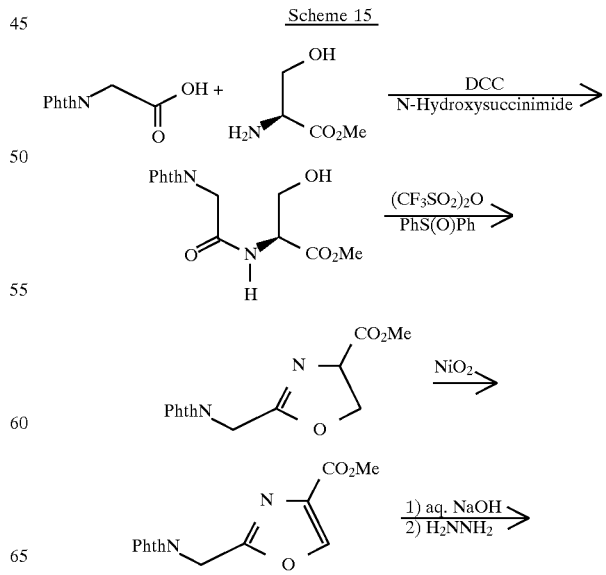

-continued
Scheme 15

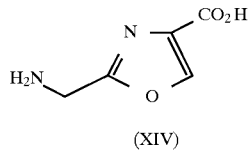

(XIV)

Tanimoto (*Chem. Pharm. Bull.*, 1984, 32, 1032) has reported the synthesis of ethyl 5-methyloxazole-2-carboxylate. The transformation of the methyl group to aminomethyl, as previously described above, should lead to the ethyl 5-(aminomethyl)-2-carboxylate linker (XV), as shown in Scheme 16.

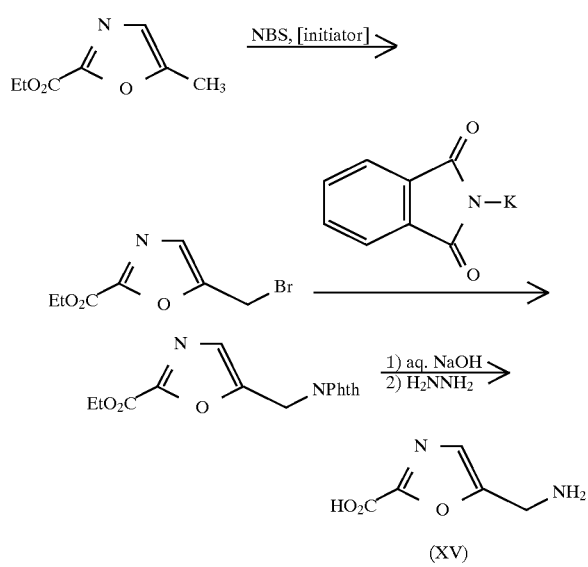

(XV)

h) Thiazoles

Synthesis of ethyl 2-(hydroxymethyl)thiazole-5-carboxylate (and the corresponding carboxylic acid) has been reported (Poittevin, Hardy; Fr. Pat. DE2548505, [1976]). As illustrated in Scheme 17 below, further transformation of the hydroxymethyl group to chloromethyl (SOCl$_2$) followed by displacement with potassium phthalimide and then hydrolysis and deprotection should provide the 2-(aminomethyl)thiazole-5-carboxylic acid linker (XVI).

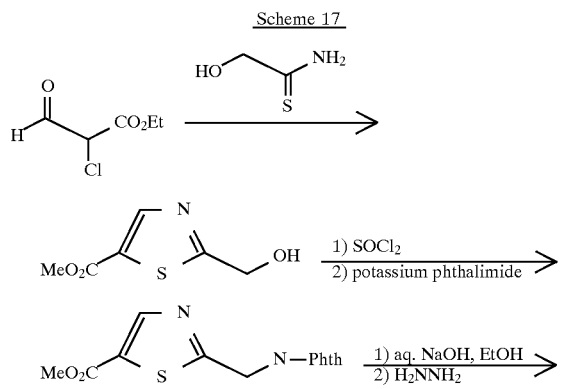

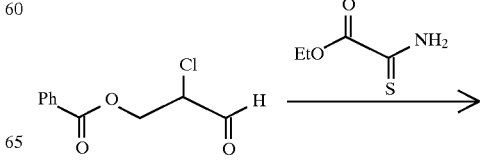

-continued
Scheme 17

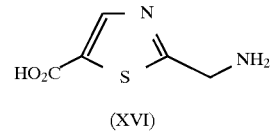

(XVI)

Synthesis of ethyl 5-methylthiazole-2-carboxylate has been accomplished by condensation of 2-bromopropionaldehyde with ethyl thiooxalamide (Erlenmeyer, Schmidt, *Helv. Chim. Acta.*, 1946, 29, 1957). As shown in Scheme 18, further transformation of the methyl group into aminomethyl, via a Gabriel-type approach as described earlier, provides 5-(aminomethyl)thiazole-2-carboxylic acid (XVII) after ester hydrolysis and cleavage of the N-phthaloyl group.

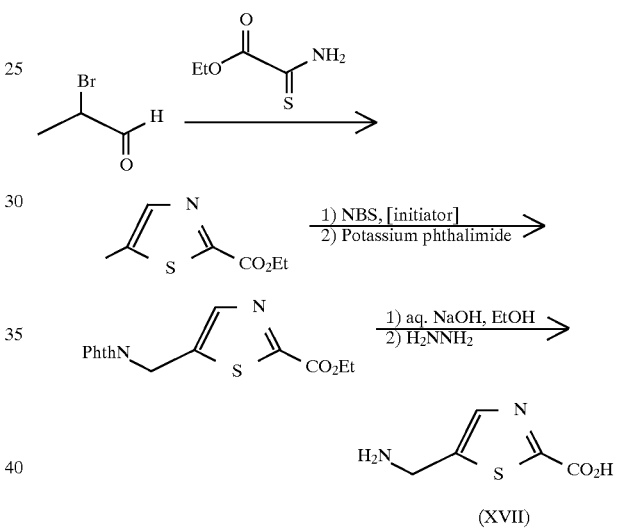

(XVII)

In the event of undesired ring bromination in the above scheme, one may make use of 2-chloro-3-(benzoyloxy) propionaldehyde (Hartman, *Theory Pract. Affinity Tech.* [*Int. Symp.*], 1978, 113) instead of 2-bromopropionaldehyde. Following comparable formation of the thiazole ring system, selective hydrolysis of the benzoate ester and conversion of hydroxymethyl to aminomethyl (via the chloride) may also lead to XVII after hydrolysis and deprotection, as shown by Scheme 19. Related known propionaldehyde derivatives such as 2-bromo-3-acetoxypropionaldehyde and 2-bromo-3-methoxypropionaldehyde may also serve as useful inroads to this series of thiazole compounds.

Scheme 19

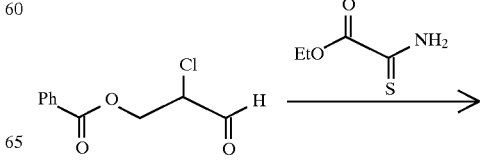

Scheme 19 -continued

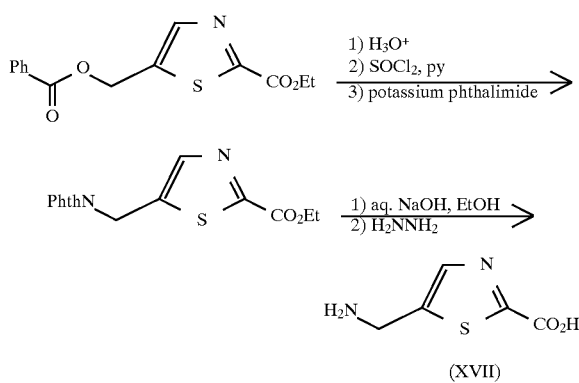

i) Isoxazoles and Isothiazoles

Analogous to the preparation of the pyrazole linker described above (Scheme 13), an appropriate ester of 2,4-dioxovaleric acid (or the commercially available carboxylic acid itself) may be condensed with hydroxylamine to give, in this case, a mixture of the isomeric 3,5-disubstituted isoxazoles. Following separation of these isomers, the methyl group is converted to aminomethyl as previously described. Again, as with the pyrazole case, in the event of unwanted ring bromination during treatment with NBS, one may instead start the synthesis using ethyl 5-(benzoyloxy)-2,4-dioxovalerate (Tschesche, *Chem. Ber.*, 1958, 91, 2074, 2079). Scheme 20 illustrates this overall approach to XVIII and XIX.

The corresponding isothiazoles (XX and XXI) can be prepared from their oxygen cogeners (XIX and XX) via a three step process involving reductive ring opening, replacement of oxygen by sulfur ($P_2S_5$), and oxidative ring closure (Newkome and Paudler, "Contemporary Heterocyclic Chemistry", Wiley-Interscience, N.Y., 1982; p41). Scheme 21 illustrates the approach.

Scheme 21

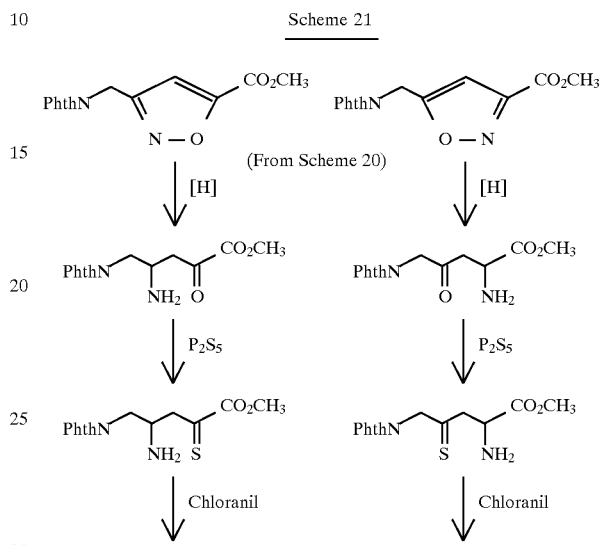

Scheme 20

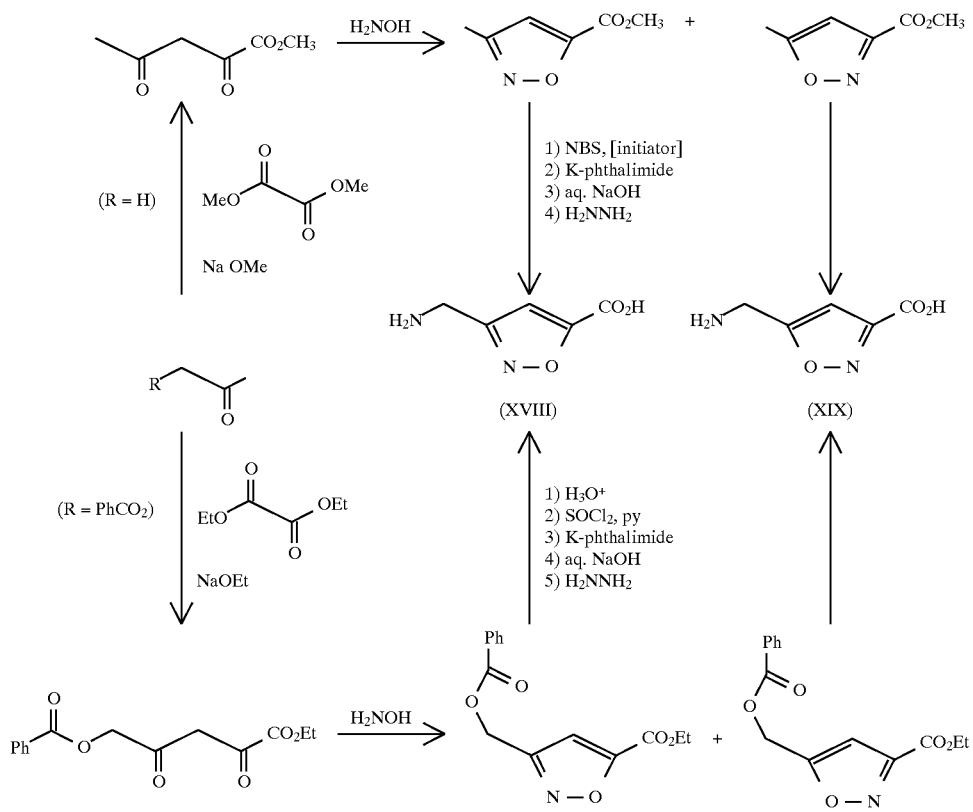

-continued
Scheme 21

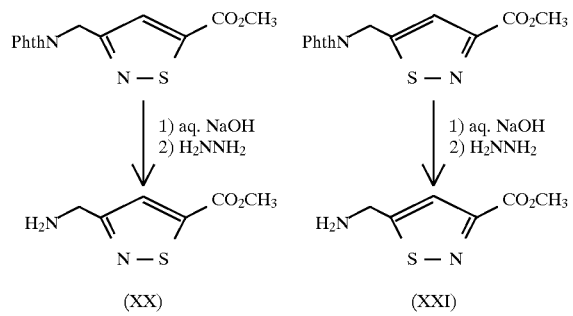

j) Oxadiazoles and Thiadiazoles

The transformation of 3,5-dimethyl-1,2,4-oxadiazole to 3-oximino-5-methyl-1,2,4-oxadiazole has been described (Bedford, *J. Med. Chem.*, 1986, 29, 2174). As further illustrated in Scheme 22, oxidative esterification of this oxime according to Said (*Synth. Commun.*, 1992, 22, 1851) leads to the corresponding ester. Conversion of methyl to aminomethyl as before (Gabriel Synthesis) ultimately gives XXII after hydrolysis and deprotection.

Scheme 22

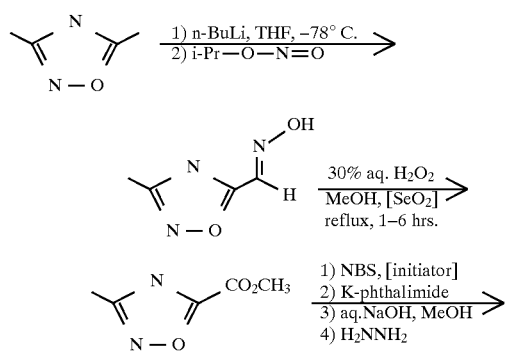

-continued
Scheme 22

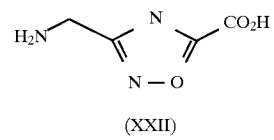

In analogous fashion, 5-aminomethyl-1,2,4-oxadiazole-3-carboxylic acid (XXIII) may be prepared from the known precursor 5-methyl-1,2,4-oxadiazole-3-carboxylic acid (Ruccia, *Ann. Chim.* (*Rome*), 1968, 58, 4, 484), according to Scheme 23. Prior esterification of the carboxylic acid of the starting material may be required to achieve efficient bromination in this case.

Scheme 23

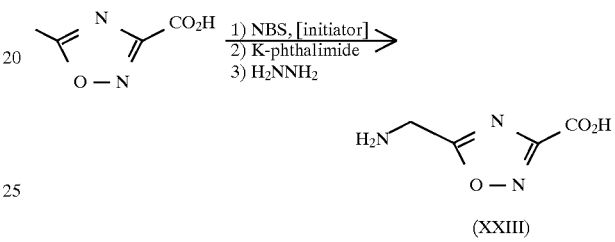

The condensation of acetamidine with trichloromethylsulfenyl chloride to give 3-methyl-5-chloro-1,2,4-thiadiazole has been reported (Goerdeler, *Chem. Ber.*, 1957, 90, 182, 184). Furthermore, MacLead (*J. Med. Chem.*, 1990, 33, 2052) has demonstrated displacement of the chlorine with various carbon and heteroatomic nucleophiles. Consequently, as shown in Scheme 24, displacement with cyanide followed by conversion of methyl to aminomethyl (Gabriel), standard hydrolysis of cyano and deprotection of phthalimino leads to 3-aminomethyl-5-carboxy-1,2,4-thiadiazole (XXIV). In an alternative approach shown here, 3,5-dimethyl-1,2,4-thiadiazole (Troyanski, *Izv. Akad., Nauk. SSSR, Ser. Khim.*, 1986, 5, 1143) may be treated with isoamylnitrite in the presence of potassium ethoxide to give 3-oximino-5-methyl-1,2,4-thiadiazole (Benschop, *J. Med. Chem.*, 1979, 22, 1306). Oxidation of the oxime to the methyl ester (Said, *Synth. Commun.*, 1992, 22, 1851) followed by Gabriel transformation of methyl to aminomethyl as previously described also leads to XXIV.

Scheme 24

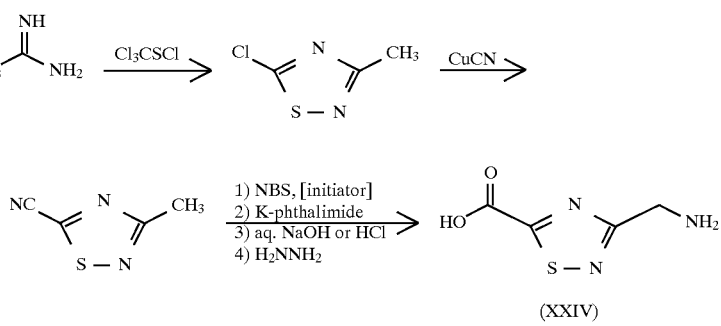

-continued
Scheme 24

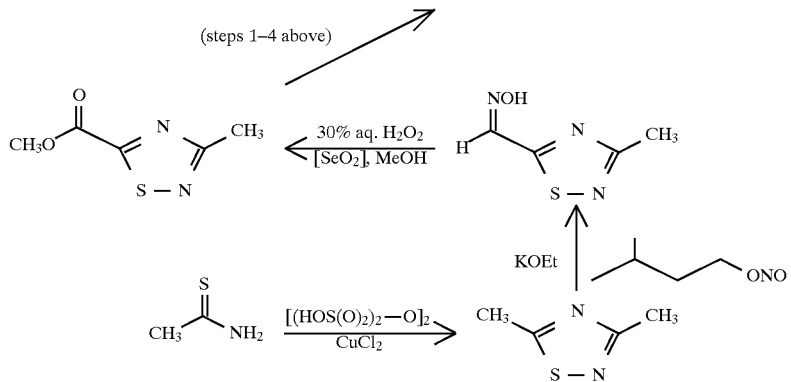

As shown in Scheme 25, 3-methyl-5-cyano-1,2,4-thiadiazole (prepared according to Scheme 24) may also be used for the synthesis of the isomeric 5-aminomethyl-1,2,4-thiadiazole-3-carboxylic acid (XXV) by applying standard functional group transformations already described.

Scheme 25

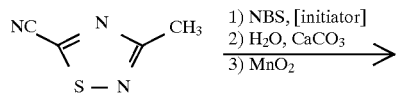

(from Scheme 24)

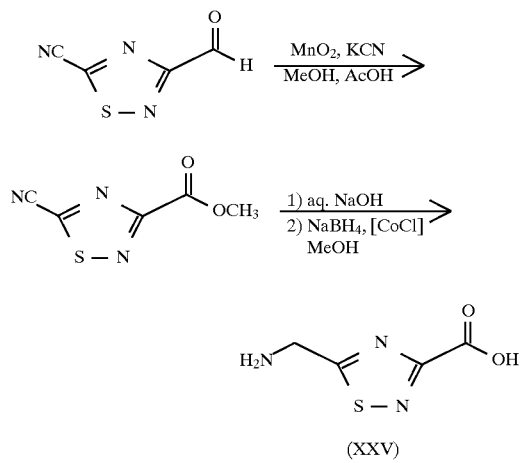

(XXV)

In Scheme 26, methyl 5-methyl-1,3,4-oxadiazole-2-carboxylate (Werber, *Atti. Scand. Accad. Sci. Lett., Arti Palermo Parte* 1, 1969–1970, 30, 175) is transformed by standard Gabriel amination, hydrolysis and deprotection to 5-aminomethyl-1,3,4-oxadiazole-2-carboxylic acid (XXVI).

Scheme 26

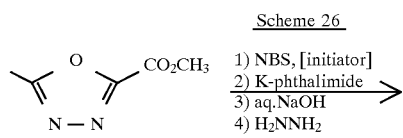

-continued
Scheme 26

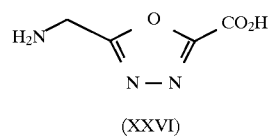

(XXVI)

Analogously, methyl 5-methyl-1,3,4-thiadiazole-2-carboxylate, prepared from the corresponding aldehyde precursor (Conway, EP125094 [1984]), is transformed by standard techniques to 5-aminomethyl-1,3,4-thiadiazole-2-carboxylic acid (XXVII, Scheme 27).

Scheme 27

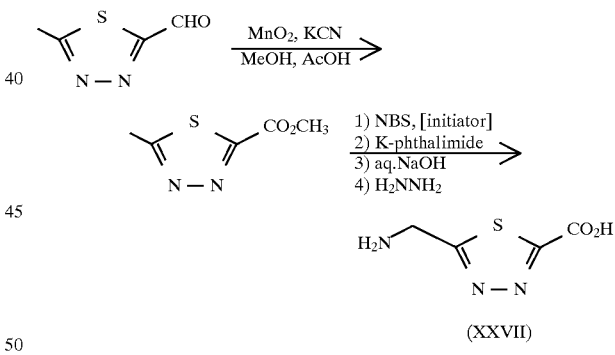

(XXVII)

Alternatively, p-chlorophenyl 5-cyano-1,3,4-thiadiazole-2-carboxylate (Irick, U.S. Pat. No. 4116928 [1978]) may be subjected to selective hydrolysis of the ester followed by reduction of nitrile to aminomethyl to give the same product (Scheme 28).

Scheme 28

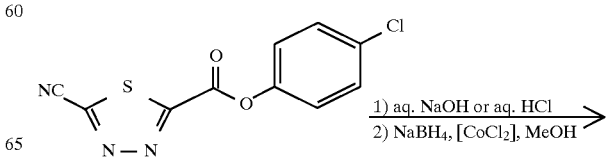

-continued
Scheme 28

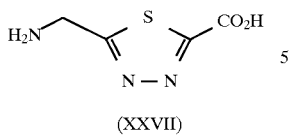

(XXVII)

2) Six-Membered Heterocyclic $R^{31}$ Groups

Table 2 lists representative six-membered nitrogenous aromatic heterocycle $R^{31}$ groups useful in the compounds of the present invention.

TABLE 2

Six-membered Heterocylics $R^{31}$ Groups

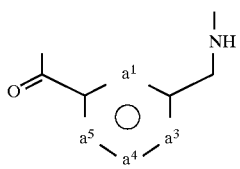

| Scheme No. | Intermediate Compound No. | Class | $a^1$ | $a^3$ | $a^4$ | $a^5$ |
|---|---|---|---|---|---|---|
| 29 | XXVIII | pyridine | N | CH | CH | CH |
| 30 | XXIX | pyridine | CH | CH | CH | N |
| 31 | XXX | pyridine | CH | CH | N | CH |
| 32 | XXXI | pyridine | CH | N | CH | CH |
| 33 | XXXII | pyrazine | N | CH | N | CH |
| 34 | XXXIII | pyrimidine | N | CH | CH | N |
| 34 | XXXIV | pyrimidine | N | N | CH | CH |
| 35 | XXXV | pyrimidine | CH | N | CH | N |
| 36 | XXXVI | pyridazine | CH | N | N | CH |
| 37 | XXXVII | pyridazine | CH | CH | N | N |
| 38 | XXXVIII | 1,2,3-triazine | CH | N | N | N |
| 39 | XXXIX | 1,2,4-triazine | N | N | N | CH |
| 40 | XL | 1,2,4-triazine | N | CH | N | N |

Pyridines

The 2,6-substituted linker may be prepared from commercially available 6-methylpicolinic acid (TCI, Japan) via Scheme 29. Esterification followed by previously discussed benzylic-type bromination, displacement with azide, and reduction give methyl 6-(aminomethyl)picolinate (XXXVIII).

Scheme 29

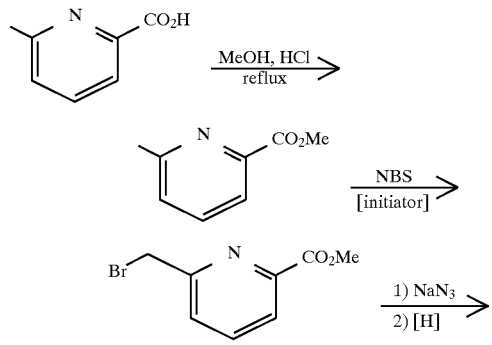

-continued
Scheme 29

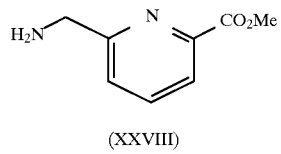

(XXVIII)

Synthesis of ethyl 4-(aminomethyl)picolinate (XXIX; Scheme 30) begins with 4-picoline which is converted to 2-amino-4-picoline according to Tschitchibabin (*J. Russ. Phys. Chem. Soc.*, 1914, 46, 1216). The amine in turn is subjected to Sandmeyer conditions to give the corresponding bromide. Halogen-metal exchange followed by quenching with ethyl chloroformate gives ethyl 4-methylpicolinate which is further converted to XXIX via the same sequence as for the 6-isomer described in the previous scheme.

Scheme 30

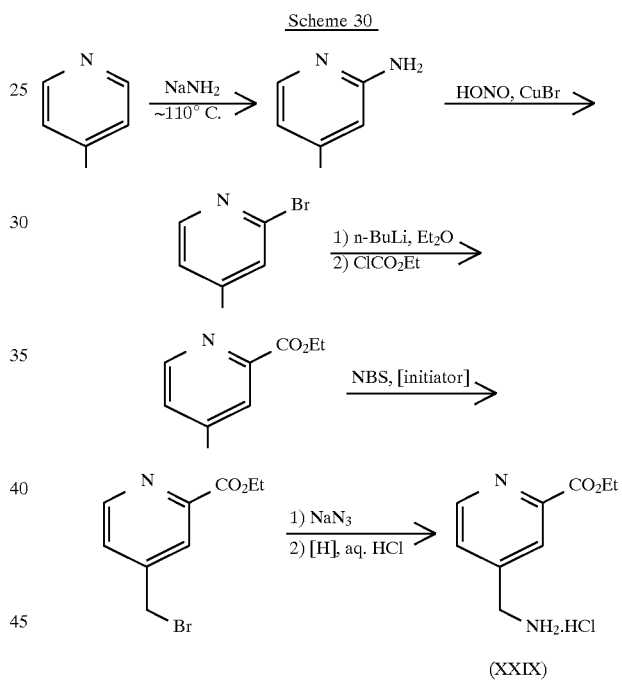

(XXIX)

Selective reduction of the half acid/ester of methyl pyridine-3,5-dicarboxylate (Delarge, *J. Pharm. Helv.,* 1969, 44, 637) with diborane to methyl 5-(hydroxymethyl) pyridine-3-carboxylate followed by conversion of hydroxymethyl to the corresponding chloride or sulfonate ester and subsequent displacement with azide gives, after catalytic hydrogenation and hydroysis, 5-(aminomethyl)-pyridine-3-carboxylic acid (XXX, Scheme 31), as illustrated below.

Scheme 31

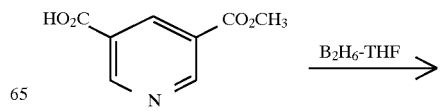

Scheme 31 -continued

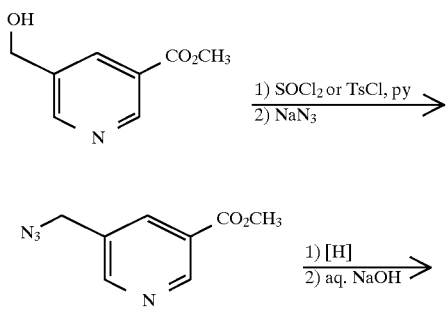

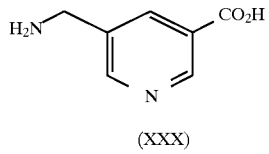

(XXX)

Synthesis of 2-(aminomethyl)pyridine-4-carboxylic acid (XXXI, Scheme 32) may be carried out starting with either 2-amino- or 2-bromo-4-methylpicoline, compounds described above (Scheme 30). In the former case, Sandmeyer conversion of the corresponding diazo salt with cyanide followed by oxidation of the methyl to the carboxylic acid gives, after reduction of cyano to aminomethyl, the target linker species. Alternatively, 2-bromo-4-methylpicoline is oxidized to the carboxylic acid which is protected as the oxazoline according to Meyers (*Tetrahedron Lett.*, 1989, 3303). Conversion of this bromide to the Grignard or lithio species followed by treatment with Katritzky's phosphazine which, following hydrolysis, introduces the aminomethyl functionality, may also give XXXI.

Scheme 32

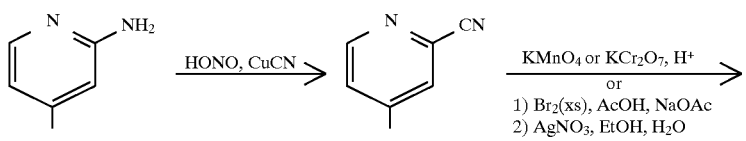

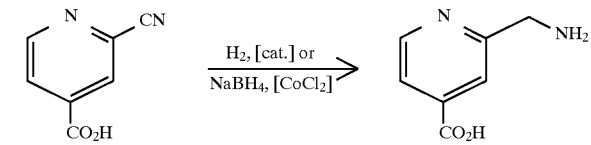

(XXXI)

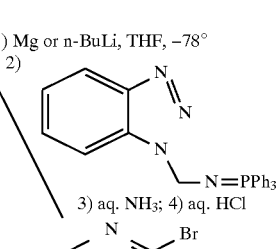

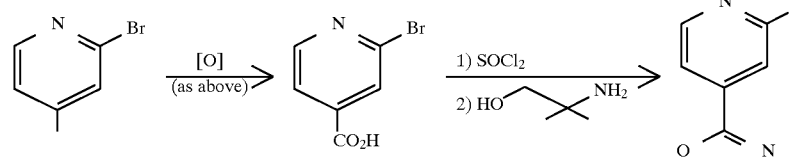

b) Pyrazine

The pyrazine linker may be prepared from either of two known precursors, as shown by Scheme 33. In the first, 6-methylpyrazine-2-carboxylic acid (Felder, *Chem. Ber.*, 1967, 100, 2, 255; Spoerri, *J. Amer. Chem. Soc.*, 1946, 68, 526) is esterified and the methyl group converted to aminomethyl using the previously described sequence (NBS/NaN$_3$/[H]). Saponification gives the target linker species, 6-(aminomethyl)pyrazine-2-carboxylic acid (XXXII).

Alternatively, 2-cyano-6-methylpyrazine (Sato, *J. Chem. Soc., Perkin Trans. I,* 1991,11, 2877; Yamagami, *J. Pharm. Sci.,* 1991, 80, 772) is converted to 2-cyano-6-([phthalimido]methyl)pyrazine (NBS/(Phth)$_2$O), the cyano group is hydrolysed to the carboxylic acid, and the amino group is liberated with hydrazine. More directly, this latter starting material may be oxidized to 6-cyanopyrazine-2-carboxylic acid followed by reduction of the cyano group to aminomethyl to also provide XXXII.

procedure). Reduction of the nitrile and saponification completes the synthesis of XXXIII).

Alternatively, selective reduction of the aldehyde to the hydroxymethyl group followed by its conversion to (phthalimido)-methyl via the chloride or sulfonate ester gives, after hydrolysis of nitrile to carboxylic acid and liberation of the amine with hydrazine, the isomeric linker (XXXIV).

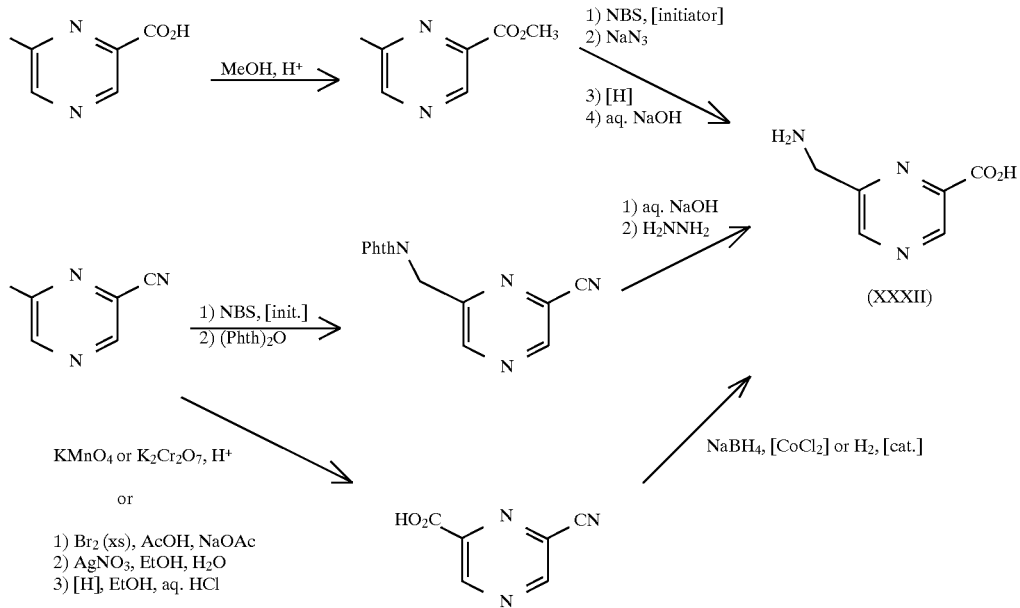

Scheme 33 c) Pyrimidines

Scheme 34 illustrates the preparation of either 4-(aminomethyl)pyrimidine-2-carboxylic acid (XXXIII) or

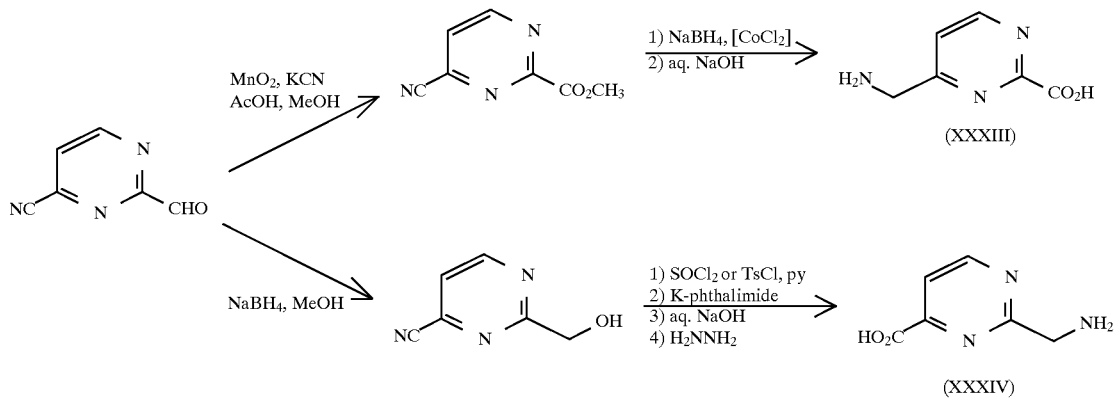

Scheme 34

2-(aminomethyl)pyrimidine-4-carboxylic acid (XXXIV) from the common intermediate 2-formyl-4-cyanopyrimidine (Stenck, EP335832, 1989; CA: 112, 21, 197872w). For the former target, the aldehyde is oxidized to the ester (Corey The third possible isomer in this series, 6-(aminomethyl)-pyrimidine-3-carboxylic acid (XXXV) can be prepared from 6-methylpyrimidine-3-carboxylic acid (Kiener, EP 442430; CA: 116, 7, 57572f). Analogous to Scheme 33 (and others above), esterification followed by transformation of methyl to aminomethyl gives the desired linker, as shown in Scheme 35.

Scheme 35

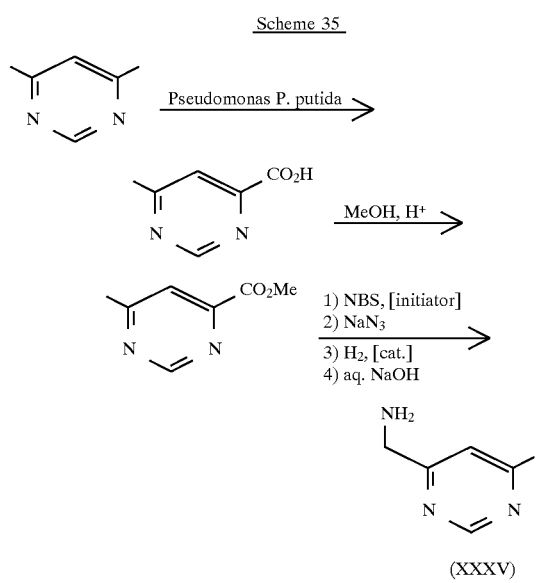

(XXXV)

d) Pyridazines

Ethyl 6-methylpyridazine-4-carboxylate has been described (Heinisch, *Tetrahedron*, 1985, 41, 1199; Turck, *C. R. Acad. Sci., Ser. C,* 1973, 277, 33). Conversion of methyl to aminomethyl, using the Gabriel-type approach as previously described in several other schemes above, followed by hydrolysis and dephthalation leads to 6-(aminomethyl) pyridazine-4-carboxylic acid (XXXVI), as illustrated in Scheme 36.

Scheme 36

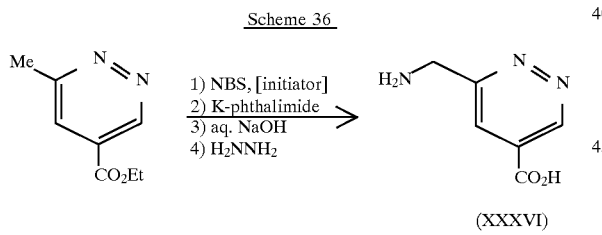

(XXXVI)

The other possible isomer in this series, 5-(aminomethyl)-pyridazine-3-carboxylic acid (XXXVII) can be obtained from the known precursor, 3-methyl-5-(hydroxymethyl) pyridazine (Ogata, *Chem. Commun.,* 1967, 22, 1176) using standard transformations previously discussed above for various other series. Scheme 37 shows the overall approach.

Scheme 37

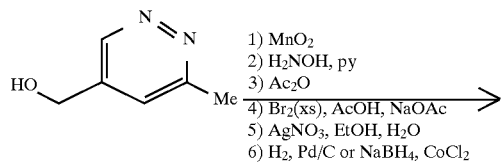

Scheme 37
-continued

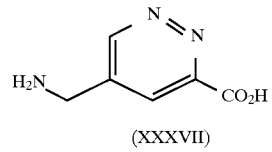

(XXXVII)

e) Triazines

Various methods have been described for the oxidative ring expansion of N-amino-pyrazoles to 1,2,3-triazines (Ohsawa, *J. Chem. Soc., Chem. Commun.,* 1980, 1182; Ibid, 1981, 1174; Ohsawa, *J. Org. Chem.,* 1985, 50, 5520; Ogata, *Chem. Pharm. Bull.,* 1988, 36, 3838). Thus, N(1)-amino-5-methylpyrazole-3-carboxylic acid, obtained from the corresponding pyrazole (Scheme 13) and hydroxylamine-O-sulfonic acid (Neunhoeffer, *Liebigs Ann. Chem.,* 1985, 9, 1732) is converted to 6-methyl-1,2,3-triazine-4-carboxylic acid according to Scheme 38. Standard transformation of methyl to aminomethyl then provides 6-(aminomethyl)-1,2,3-triazine-4-carboxylic acid (XXXVIII).

Scheme 38

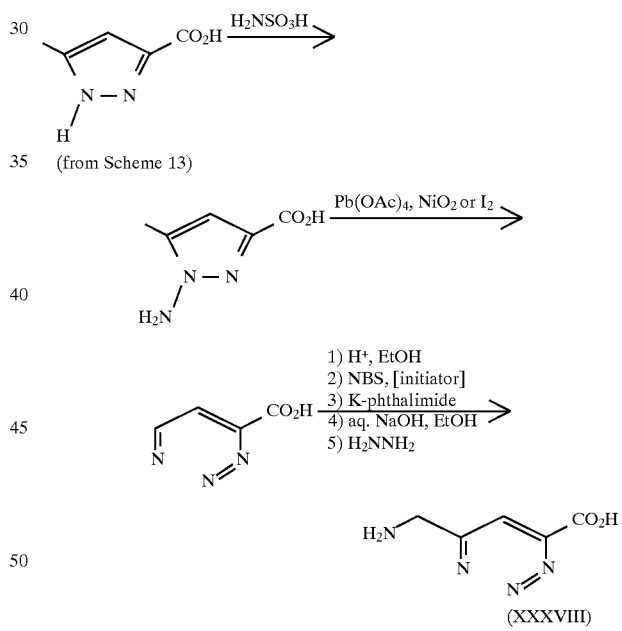

(XXXVIII)

Rykowski has described the base-catalysed oximation of 3-methyl-1,2,4-triazine to give 3-methyl-5-oximino-1,2,4-triazine (*Tetrahedron Lett.,* 1984, 4795). This oxime may serve as a key intermediate for either of the two possible 1,2,4-triazine linkers.

For example, as shown in Scheme 39, oxidative esterification of the oxime group according to Said (*Synth. Commun.,* 1992, 22, 1851) followed by standard conversion of methyl to aminomethyl leads to 3-aminomethyl-1,2,4-triazine-5-carboxylic acid (XXXIX).

Scheme 39

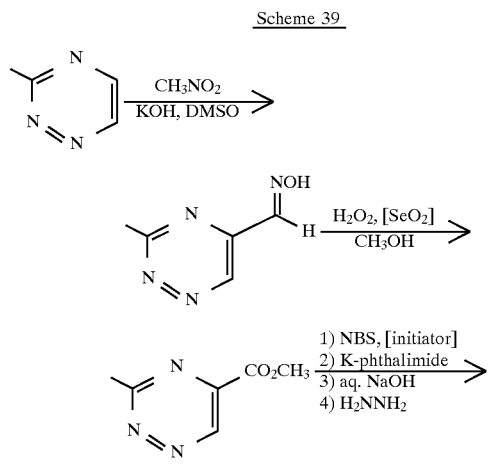

Alternatively, this oxime is reduced to aminomethyl and protected as the phthalimide. Oxidation of the methyl group to the carboxylic acid followed by deprotection of the amine leads to 5-aminomethyl-1,2,4-triazine-3-carboxylic acid (XL), as shown by Scheme 40.

Scheme 40

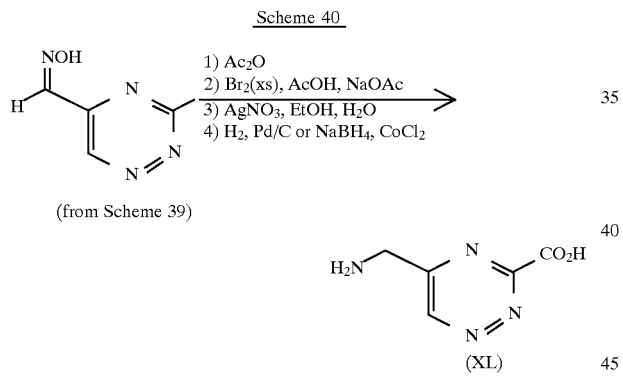

Synthesis of Cyclic Peptides

The cyclic peptide compounds of the present invention may be prepared by the method of DeGrado and Kaiser (*J. Org. Chem.*, 1980, 45, 1295) or through a modification thereof. Thus, as shown in Scheme 41 (for those examples where J=D-Val, K=N-(Me)Arg, L=Gly, and M=Asp), the linker species (Schemes 1–41) is protected as the N-Boc intermediate and then at the carboxy terminus as the p-nitrobenzophenone oxime ester. Liberation of the amine with TFA (or dilute aqueous mineral acid in THF) is followed by coupling with N-Boc-Asp(Chx)-OH. Following removal of the Boc group as before allows further coupling to the protected tripeptide Boc-D-Val-N-(Me)Arg(Tos)-Gly-OH. Following deprotection of this linear peptide with TFA, cyclization with concomitant cleavage of the oxime ester group is achieved by stirring in the presence of diisopropylethylamine and acetic acid in an appropriate solvent (DMF, ACN) at 50°–60° C. for 6–72 hours.

Alternatively, as shown in Scheme 42 the linker may be treated directly with the Asp-derivative activated by the formation of the succinimide ester. Removal of Boc-protection followed by the reaction with the succinimide-ester-activated Boc-tripeptide yields the pentapeptide. The Boc group is removed as before (TFA). The TFA-pentapeptide is then cyclized in the presence of HBTU at pH 8 in DMF-ACN.

The isolated product is then treated using standard procedures with anhydrous hydrogen fluoride (Stewart and Young, "Solid Phase Peptide Synthesis", 2nd Ed., Pierce Chemical Co., 1984; p85) containing 1 ml/g m-cresol or anisole as scavenger at 0° C. for 20–60 minutes to remove side-chain protecting groups. The crude product may be purified by reversed-phase HPLC using a 2.5 cm preparative Vydac C18 column with a linear acetonitrile gradient containing 0.1% TFA to produce the pure cyclized material.

Scheme 41

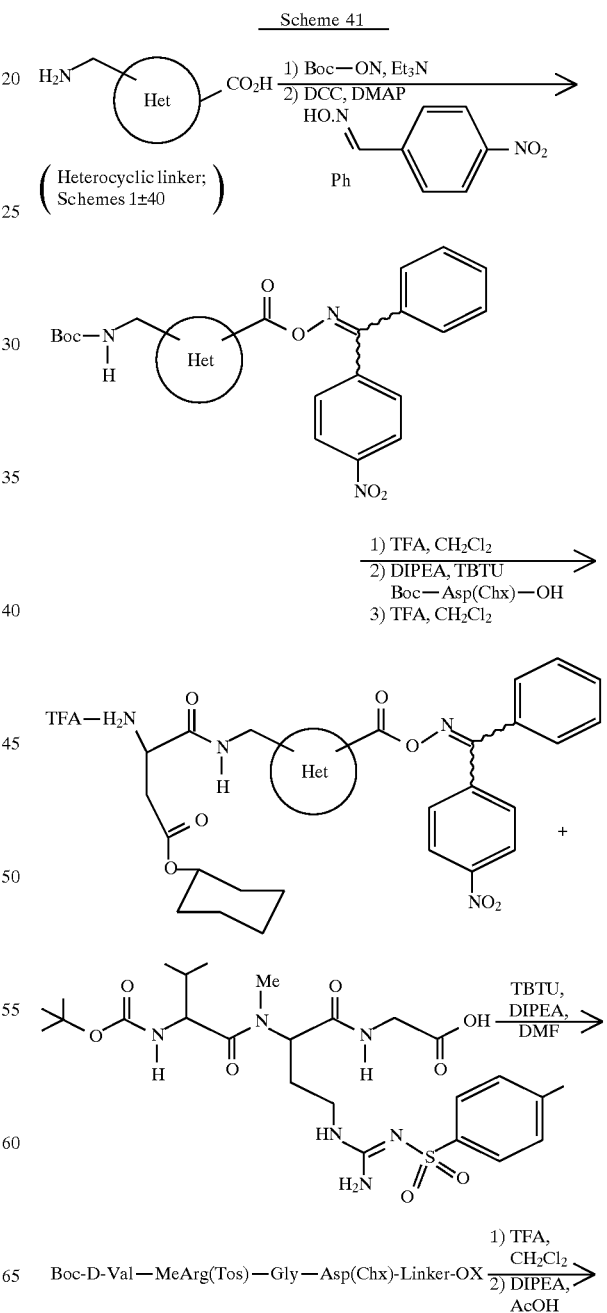

55
-continued
Scheme 41
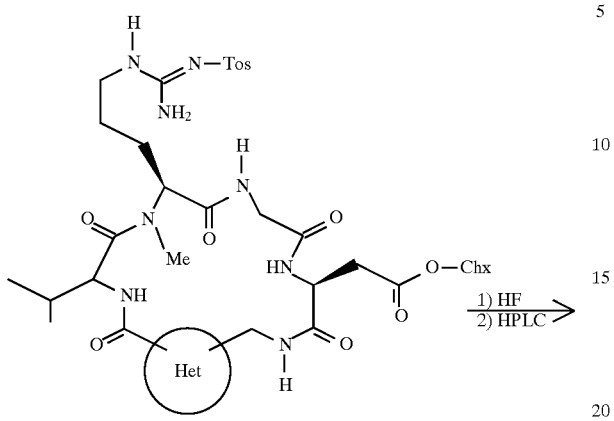
56
-continued
Scheme 41
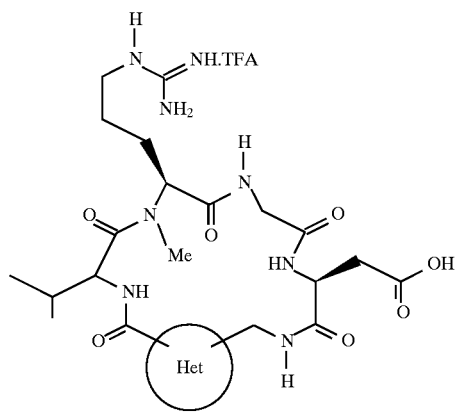
Scheme 42
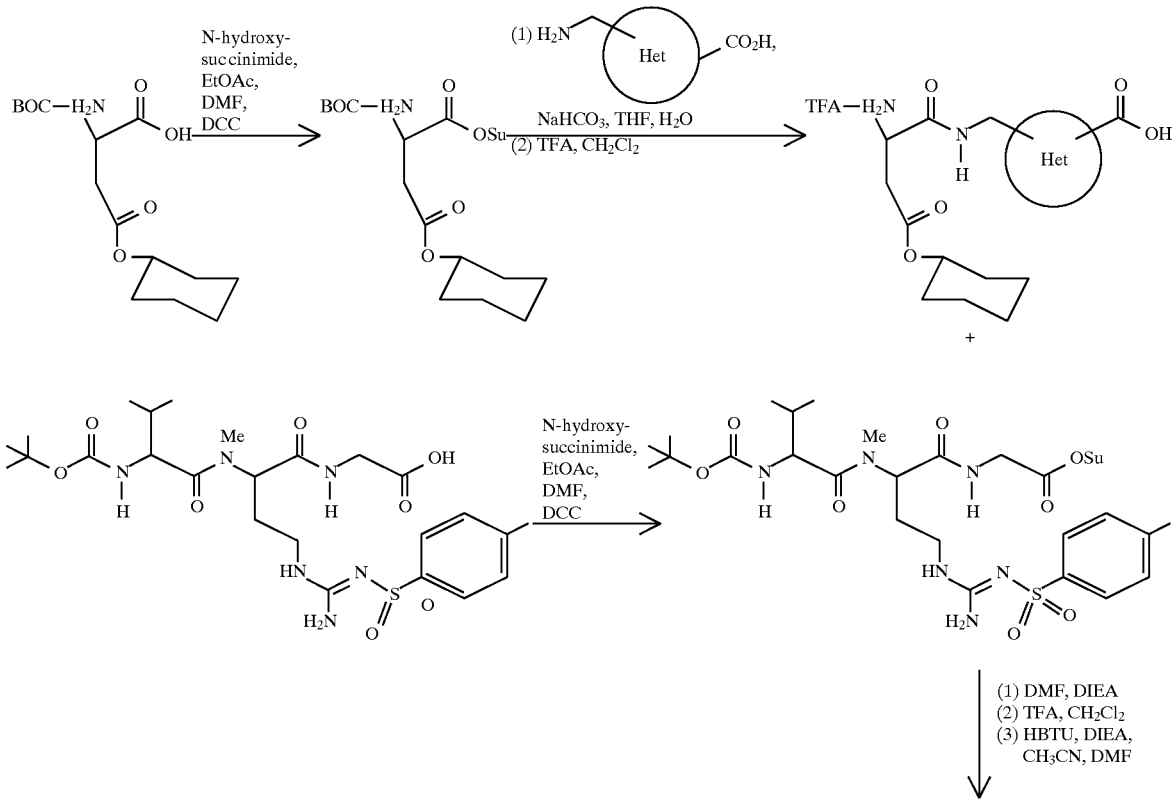

-continued
Scheme 42

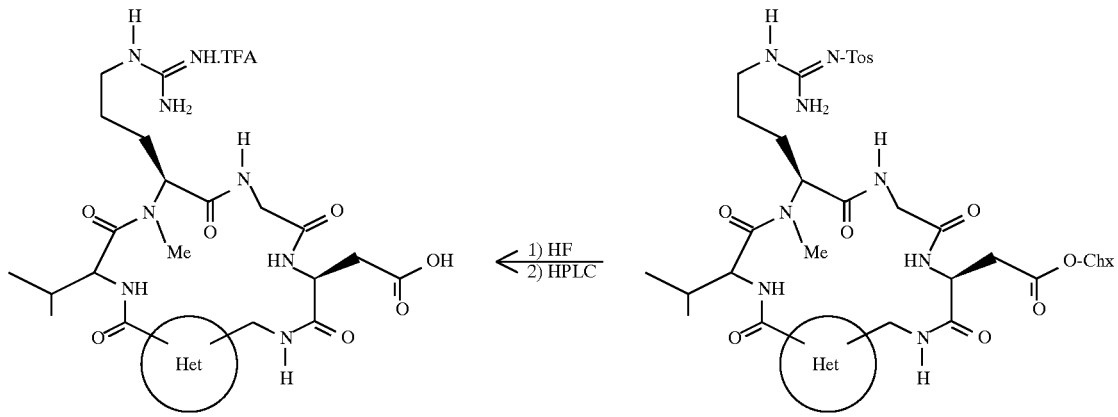

The synthesis of compounds of this invention is further exemplified below. Table 3 below sets forth representative compounds of the present invention.

Example 1 cyclo-(D-Val-N(Me)Arg-Gly-Asp-[5-aminomethyl]-2-furoate);

J=D-Val, K=N(Me)Arg, L=Gly, M=Asp
Part A—Methyl 5-methyl-2-furoate

To a stirred solution of 5-methylfurfural (10.0 g, 91 mmol) in methanol (500 ml) was added glacial acetic acid (5.5 g, 91 mmol), potassium cyanide (17.7 g, 273 mmol) and activated manganese dioxide (79 g, 910 mmol). After continued stirring for one hour at ambient temperature the mixture was filtered through a bed of Celite filter aid with applied house vacuum and the filtrate was concentrated on the rotary evaporator. The residue was partitioned between ethyl acetate (250 ml) and water (100 ml), the organic phase was washed further with saturated aqueous sodium bicarbonate (50 ml) and brine (50 ml), dried over anhydrous magnesium sulfate, filtered and concentrated to provide 10.3 g (81%) of the title compound as a yellow-orange liquid. 1H-NMR (300 MHz, CDCl$_3$): 7.10 ppm (m, 1H), 6.12 (d, 1H, J=2.5 Hz), 3.85 (s, 3H), 2.38 (s, 3H). MS (CH$_4$—CI): [M+H]$^+$=141.

Part B—Methyl 5-(bromomethyl)-2-furoate

To a solution of methyl 5-methyl-2-furoate (9.2 g, 65.6 mmol) in DCM (300 ml) was added N-bromosuccinimide (11.7 g, 65.6 mmol) and 2,2'-azobis(2,4-dimethylpentanenitrile (VAZO®52; 0.82 g, 3.3 mmol). The mixture was stirred at ambient temperature for 15 hours. The mixture was washed with 5% Na$_2$S$_2$O$_3$ (100 ml) and water (2×50 ml) and the organic phase was dried over anhydrous sodium sulfate before being filtered and concentrated to give 14.4 g of the title compound as a pale yellow oil. 1H-NMR (CDCl$_3$): 7.13 ppm (d, 1H, J=2 Hz), 6.50 (d, 1H, J=2 Hz), 4.49 (s, 2H), 3.90 (s, 3H). MS (CH$_4$—CI): [M+H]$^+$=221 ($^{81}$Br isotope; monobromo isotope pattern).

Part C—Methyl 5-(azidomethyl)-2-furoate

To a solution of methyl 5-(bromomethyl)-2-furoate (14.5 g, 66.2 mmol) in anhydrous DMF (250 ml) was added powdered sodium azide (6.5 g, 99.3 mmol). The mixture was stirred at ambient temperature for 18–24 hours. The bulk of the DMF was removed on the rotary evaporator and the residue was partitioned between DCM (250 ml) and water (100 ml). The organic phase was washed further with water (2×100 ml) and brine (100 ml), dried over anhydrous magnesium sulfate, filtered and concentrated to provide 12 g of the title compound as a yellow-orange oil. 1H-NMR (CDCl$_3$): 7.15 ppm (d, 1H, J=4 Hz), 6.47 (d, 1H, J=4 Hz), 4.39 (s, 2H), 3.90 (s, 3H). MS (CH$_4$—CI): [M+H]$^+$=182.

Part D—Methyl 5-(aminomethyl)-2-furoate hydrochloride salt

To a solution of methyl 5-(azidomethyl)-2-furoate (13 g, 71.8 mmol) in methanol (400 ml) was added 10% Pd/C (4.3 g) followed by concentrated hydrochloric acid (8.7 ml). The mixture was placed under hydrogen gas (30–40 psi) on a Paar apparatus and shaken at ambient temperature for three hours. The mixture was filtered through Celite with applied house vacuum and the filtrate was concentrated on the rotary evaporator. The solid residue was slurried with diethyl ether (200 ml), collected by suction filtration and dried under vacuum to give 11.8 g of the title compound. 1H-NMR (CDCl$_3$): 7.18 ppm (d, 1H, J=3 Hz), 6.75 (d, 1H, J=3 Hz), 4.23 (s, 2H), 4.01 (s, 5H; suppressed in D$_2$O), 3.91 (s, 3H). MS (NH$_3$—CI): [M+NH$_4$]$^+$=173 (free base).

Part E—N-(Boc)-5-aminomethyl-2-furoic acid

To a solution of methyl 5-aminomethyl-2-furoate hydrochloride (7.0 g, 36.5 mmol) in 1,4-dioxane (70 ml) and water (70 ml) was added triethylamine (7.6 ml, 54.8 mmol) followed by BOC-ON (9.9 g, 40.2 mmol). The mixture was stirred for about five hours whereupon 4N NaOH (70 ml) was added and the resulting mixture was allowed to stir for an additional 18 hours. The clear yellow mixture was extracted with diethyl ether (2×150 ml), the aqueous phase was adjusted to pH 4 with 4N HCl and the resulting oily precipitate was extracted with DCM (2×200 ml). The combined DCM phases were washed with brine (50 ml), dried over anhydrous magnesium sulfate, filtered, and concentrated to provide 16.8 g of a tan solid. Recrystallization from diethyl ether provided 4.1 g of the title compound as a white solid. $^1$NMR (CD$_3$OD): 7.13 ppm (d, 1H, J=3.5 Hz), 6.36 (d, 1H, J=3.5 Hz), 4.89 (s, 2H; suppressed in D$_2$O), 4.26 (s, 2H), 1.44 (s, 9H); MS (NH$_3$—CI): [M+NH$_4$]$^+$=259.

Part F—4'-nitrobenzophenimino N-(Boc)-5-aminomethyl-2-furoate

To a solution of N-(Boc)-5-aminomethyl-2-furoic acid (3.3 g, 13.7 mmol) in dichloromethane (130 ml) was added 4-nitrobenzo-phenone oxime (3.3 g, 13.7 mmol) followed by 4-(dimethylamino)-pyridine (1.7 g, 13.7 mmol) and dicyclohexylcarbodiimide (2.8 g, 13.7 mmol). The mixture was stirred at ambient temperature and filtered of dicyclohexylurea. The filtrate was concentrated and the residue was dissolved in ethyl acetate (200 ml). The organic phase was washed with 5% citric acid (2×100 ml), saturated aqueous sodium bicarbonate (2×100 ml), brine (100 ml), dried over anhydrous magnesium sulfate, filtered, and concentrated to provide 6.6 g of crude of-white solid. Recrystallization (ethyl acetate/hexanes, ½; 75 ml) gave 4.6 g of the pure title compound as a white solid. $^1$H-NMR (CDCl$_3$): 8.40–6.31 ppm (m, 11H), 4.95 (s, 1H; suppressed in D$_2$O), 4.32 (m, 2H), 1.44 (s, 9H); MS (NH$_3$—CI): [M+NH$_4$]$^+$=483.

Part G—4'-nitrobenzophenimino 5-aminomethyl-2-furoate trifluoroacetate salt

To a solution of 4-nitrobenzophenimino N-(Boc)-5-aminomethyl-2-furoate (0.70 g, 1.5 mmol) in DCM (3 ml) was added dropwise trifluoroacetic acid (1 ml). The mixture was stirred for one hour at ambient temperature, concentrated (first on the rotary evaporator, then at 1 mm Hg at 40° C.) and the residue was stirred in diethyl ether (20 ml) and stored overnight at 0° C. The solid was collected by suction filtration, washed with diethyl ether and dried to give the 0.71 g of the title compound as a pale yellow solid. $^1$H-NMR (CDCl$_3$): 8.46–8.31 ppm (m, 1H), 7.90–7.45 (m, 8H), 6.95–6.90 (m, 1H), 6.69 (m, 1H), 4.90 (s, 3H; suppressed in D$_2$O), 4.25 (m, 2H); $^{19}$F-NMR (CD$_3$OD): −76 ppm; MS (NH$_3$—CI): [M+NH$_4$]$^+$ (for free base)=383.

Part H—4'-nitrobenzophenimino N-(BOC)-Asp(CHX)-5-aminomethyl-2-furoate

To a solution of N-(BOC)-Asp(CHX)-OH (0.33 g, 1.04 mmol)) in anhydrous DMF (2 ml) was added diisopropylethylamine (0.38 ml, 2.2 mmol) and HBTU (0.40 g, 1.04 mmol). The mixture was stirred at ambient temperature for about five minutes whereupon 4-nitrobenzophenimino 5-aminomethyl-2-furoate trifluoroacetate (0.5 g, 1.04 mmol) was added and the resulting mixture was stirred further for 18 hours. The reaction mixture was dissolved into ethyl acetate (50 ml) and washed with 5% aqueous citric acid (2×25 ml), water (25 ml), saturated aqueous sodium bicarbonate (25 ml), brine (25 ml), dried over anhydrous magnesium sulfate, filtered and concentrated. The residue was triturated with hexanes, collected by filtration and dried to give 0.78 g of the title compound as a pale yellow solid. 1H-NMR (CDCl$_3$): 8.38 ppm (d, 1H, J=2 Hz), 8.23 (d, 1H, J =2 Hz), 7.05 (m, 9H), 6.80–6.75 (m, 1H), 6.23 (m, 1H), 5.65 (m, 1H), 4.75 (m, 1H), 4.50–4.40 (m, 2H), 3.00–2.60 (m, 2H), 1.85–1.20 (m, 19H); HRMS (NH$_3$—DCI): [M+H]$^+$ calc.=663.266619;[M+H]$^+$obsd.=663.264802.

Part I—4'-nitrobenzophenimino Asp(CHX)-5-aminomethyl-2-furoate trifluoroacetate salt This compound was prepared using the procedure described above in Part G. From 4-nitrobenzophenimino N-(BOC)-Asp(CHX)-5-aminomethyl-2-furoate (1.0 g, 1.5 mmol) in DCM/TFA (3 ml/1 ml) was obtained 1.1 g of the title compound as a light brown amorphous solid. 1H-NMR (CDCl$_3$): 8.80–8.60 ppm (m, 1H), 8.38 (d, 1H, J=2 Hz), 8.23 (d, 1H, J=2 Hz), 7.85–7.30 (m, 7H), 6.68–6.60 (m, 1H), 6.30 (m, 1H), 4.75–4.60 (m, 2H), 4.60–4.30 (m, 2H), 3.10–3.00 (m, 2H), 1.80–1.10 (m, 10H); $^{19}$F-NMR (CDCl$_3$): −76.4 ppm; MS (NH$_3$—DCI): [M+NH$_4$]$^+$ (for free base)=580.

Part J—4'-nitrobenzophenimino N-(BOC)-D-Val-N(Me)Arg(Tos)-Gly-Asp(CHX)-5-aminomethyl-2-furoate This compound was prepared according to the procedure described above in Part H. From 4-nitrobenzophenimino Asp(CHX)-5-aminomethyl-2-furoate trifluoroacetate (1.1 g) and N-(BOC)-D-Val-N(Me)Arg(Tos)-Gly-OH (0.97 g) was obtained 1.95 g of the title compound as a burnt yellow solid. Flash column chromatography (silica gel, 5% MeOH/CHCl$_3$) gave 1.68 g of purified material as a yellow solid. NMR (CDCl$_3$): 8.39 ppm (d, 1H, J=9 Hz), 8.22 (d, 1H, J=9 Hz), 7.79–7.18 (m, 11H), 6.75 & 6.70 (2d, 1H, J=3 Hz), 6.46 (s, 1H), 6.37 (d, 1H, J=3 Hz), 5.30–5.15 (m, 2H), 4.80 (m, 1H), 4.70 (m, 1H), 4.35 (m, 2H), 4.15 (m, 2H), 3.75 (m, 2H), 3.35–3.20 (m,2H), 3.05 (2s, 3H), 2.63 (m, 1H), 2.39 (s, 3H), 2.10 (m, 1H), 1.95 (m, 1H), 1.80–1.60 (m, 6H), 1.45–1.20 (m+s, 18H), 1.01–0.93 (2d, 6H, J=7 Hz); HRMS (FAB-NBA): [M+H]$^+$calc.=1143.482109; [M+H]$^+$obs.=1143.481018.

Part K—4'-nitrobenzophenimino D-Val-N(Me)Arg(Tos)-Gly-Asp(CHX)-5-aminomethyl-2-furoate trifluoroacetate salt This compound was prepared according to the procedure described above in Part G. From 4'-nitrobenzophenimino N-(BOC)-D-Val-N(Me)Arg(Tos)-Gly-Asp(CHX)-5-aminomethyl-2-furoate (1.47 g, 1.29 mmol) in DCM/TFA (6 ml/2 ml) was obtained 1.34 g of the title compound as a light yellow amorphous powder. $^1$H-NMR (CDCl$_3$): 8.35 ppm (d, 1H, J=9 Hz), 8.22 (d, 1H, J=9 Hz), 8.20–8.15 (m, 3H), 7.95–7.85 (m,1H), 7.82–6.95 (m, 13H), 5.30 (m, 2H), 4.85 (m, 1H), 4.65 (m, 1H), 4.37 (m, 5H), 3.80 (m, 2H), 3.23 (m, 2H), 2.95 (s, 3H), 2.75 (m, 1H), 2.38 (s, 3H), 2.21 (m, 1H), 2.08 (m, 1H), 1.80–1.60 (m, 6H), 1.31–1.19 (m, 9H), 1.19–0.96 (2d, 6H, J=7 Hz); $^{19}$F-NMR (CDCl$_3$): −76 ppm; MS (FAB-NBA): [M+H]$^+$=1043.

Part L—cyclo-(D-Val-N(Me)Arg(Tos)-Gly-Asp(CHX)-5-aminomethyl-2-furoate)

To a solution of 4'-nitrobenzophenimino D-Val-N(Me)Arg(Tos)-Gly-Asp(CHX)-5-aminomethyl-2-furoate trifluoroacetate (1.2 g, 1.07 mmol) in anhydrous DMF (110 ml) was added diisopropylethyl-amine (0.75 ml, 4.3 mmol) and glacial acetic acid (0.25 ml, 4.3 mmol). The mixture was stirred at 60° C. two hours at which time tlc analysis indicated complete consumption of starting material. The DMF was removed under vacuo and the yellow oily residue was dissolved into ethyl acetate/n-butanol (60 ml, 1/1), washed with 5% aqueous citric acid (3×30 ml), brine (30 ml), dried over anhydrous magnesium sulfate, filtered and concentrated. The resulting oil was triturated several times with diethyl ether and stirred overnight in ethyl acetate (100 ml) to give 0.68 g of the title compound as an off-white amorphous solid.

$^1$H-NMR (CDCl$_3$): 7.75 ppm (d, 2H, J=5 Hz), 7.25 (s, 1H), 7.23 (d, 2H, J=5 Hz), 7.03 (d, 1H, J=3 Hz), 6.27 (d, 1H, J=3 Hz), 5.16 (m, 1H), 4.90–4.57 (m, 7H), 4.11–3.80 (m, 3H), 3.23–3.10 (m, 2H), 2.89 (s, 3H), 2.88–2.58 (m, 2H), 2.38 (s, 3H), 2.30–2.22 (m,1H), 2.05–1.87 (m, 1H), 1.85–1.58 (m, 6H), 1.57–1.23 (m, 10H), 1.02 (d, 3H, J=6 Hz), 0.94 (d, 3H, J=6 Hz); HRMS (NH$_3$—DCI): [M+H]$^+$ calc.=801.360537; [M+H]$^+$obs.=801.359482.

Part M—cyclo-(D-Val-N(Me)Arg-Gly-Asp-5-aminomethyl-2-furoate) trifluoroacetate salt Cyclo-(D-Val-N(Me)Arg(Tos)-Gly-Asp(CHX)-5-aminomethyl-2-furoate) (0.55 g, 0.69 mmol) and 550 μL of m-cresol were treated with anhydrous hydrogen fluoride at 0° C. for 1 hour. The crude material was precipitated with ether, redissolved in aqueous HOAc, and lyophilized to generate the title compound as a pale yellow solid (0.39 g, 91%; calculated as the acetate salt). Purification was accomplished by reversed-phase HPLC on a preparative Vydac C18 column (2.5 cm) using a 0.23%/min. gradient of 9 to 23% acetonitrile containing 0.1% TFA and then lyophilized to give 0.17 g of the title compound as a fluffy white solid (44% recovery, overall yield 40%). $^1$H-NMR (CDCl$_3$): 8.46 ppm (d, 1H, J=7 Hz), 8.38 (d, 1H, J=7 Hz), 8.03 (m, 1H), 7.57 (t, 1H, J=6 Hz), 7.36 (t, 1H, J=6 Hz), 7.16 (d, 1H, J=3 Hz), 6.42 (d, 1H, J=3 Hz), 5.14–5.09 (m, 1H), 4.60–4.42 (m, 5H), 4.14–3.90 (m, 5H), 3.72–3.65 (m, 1H), 3.15–3.09 (m, 2H), 2.87 (s, 3H), 2.74–2.66 (2d, 1H, J=6 Hz), 2.17–2.12 (m, 1H), 1.93–1.91 (m, 1H), 1.66–1.53 (m, 1H), 1.38–1.31 (m, 1H), 0.99 (d, 3H, J=7 Hz), 0.92 (d, 3H, J=7 Hz); HRMS (FAB-NBA): [M+H]$^+$calc.=565.273436; [M+H]$^+$obs.= 565.272777.

Example 2 cyclo-(D-Val-N(Me)Arg-Gly-Asp-[5-aminomethyl]-2-thiophenecarboxylate);

J=D-Val, K=N(Me)Arg, L=Gly, M=Asp

Part A—2-Bromomethyl-5-thiophenecarboxylic acid.

To a solution of 5-methyl-2-thiophenecarboxylic acid (6.096 g, 42.88 mmol) in hot CCl$_4$ (150 mL) was added N-bromosuccinimide (7.63 g, 42.9 mmol) and benzoyl peroxide (300 mg, 1.24 mmol). Heat at reflux for 24 hr, then filter hot. Concentration of the filtrate then gave 6.8 g of crude bromide as a 4:1.5:1 mixture of desired product: succinimide: 5-methyl-2-thiophenecarboxylic acid. $^1$H NMR (acetone-d$_6$) 7.65 ppm (1H, d, J=3.5 Hz), 7.30 (1H, d, J=3.5 Hz), 4.97 (2H, s).

Part B—2-Azidomethyl-5-thiophenecarboxylic acid

Into a bomb was placed a solution of 2-bromomethyl-5-thiophenecarboxylic acid (21.3 g, 4:2:1 mixture) in DMF (300 mL). To this was added sodium azide (5.00 g, 76.9 mmol). The resulting mixture was heated at 70° C. for 2 h, then cooled to room temperature. After dilution with ethyl acetate, the mixture was washed with water (4×), followed by brine. The solution was then dried over MgSO$_4$, concentrated and placed under vacuum to constant weight, giving 11.53 g (82%) of a 4:2:1 mixture of desired product:succinimide:5-methyl-2-thiophenecarboxylic acid. $^1$H NMR (DMSO-d$_6$) 7.63 ppm (1H, d, J=3.6 Hz), 7.19 (1H, d, J=3.6 Hz), 4.73 (2H, s).

Part C 2-Aminomethyl-5-thiophenecarboxylic acid

To a solution of 2-azidomethyl-5-thiophenecarboxylic acid (11.53 g, 62.9 mmol) in ethanol (100 mL) was added 10% Pd/C (1.00 g) and 6M HCl (10.5 mL, 63 mmol). The mixture was placed under a pressure of hydrogen (50 psi) for 24 h, then filtered through celite™ (ethanol followed by water wash). Concentration, followed by crystallization from methanol/ethyl acetate gave 4.14 g (34%) of amino acid hydrochloride salt. 1H NMR (DMSO-d$_6$): 8.81 ppm (bs, 3H,), 7.66 (1 H, d, J=3.7 Hz), 7.36 (1H, d, J=3.7 Hz), 4.26 (2H, s); MS (DCI-NH$_3$): [M+NH$_4$]$^+$=175.

Part D—Dicyclohexylammonium 2-(Butyloxycarbonyl)amino-methyl-5-thiophenecarboxylate To a solution of 2-aminomethyl-5-thiophenecarboxylic acid (1.72 g, 9.4 mmol) in 50% aqueous dioxane (12 mL) was added triethylamine (3.2 mL, 23 mmol) followed by Boc-On (2.71 g, 11.0 mmol). The mixture was stirred overnight at room temperature (20 h), followed by dilution with water. After adjustment to pH 2, the mixture was extracted with ethyl acetate (4×). The combined organic extracts were washed with water, followed by brine, dried (MgSO$_4$) and concentrated to give a brown oil. To an ether solution of this oil was added dicyclohexylamine (1 eq) which caused the dicyclohexylammonium salt of the desired product to precipitate, giving 2.24 g (54%) after filtration and drying to constant weight.

$^1$H NMR (CDCl$_3$) 7.38 ppm (1H, d, J=3.3 Hz), 6.86 (1H, d, J=3.3 Hz), 4.9 (1H, bs), 4.44 (2H, d, J=5.5 Hz), 3.05 (2H, m), 2.09 (4H, m), 1.78 (4H, m), 1.58 (6H, m), 1.46 (9H, s), 1.21 (6H, m).

Part E—Boc-AMTC-Ox

To a solution of dicyclohexylammonium 2-(butyloxycarbonyl)aminomethyl-5-thiophenecarboxylate (877 mg, 2.00 mmol) in dichloromethane (10 mL) was added p-nitrobenzophenone oxime (484 mg, 2.00 mmol) and 4-dimethylaminopyridine (25 mg, 0.20 mmol). The resulting solution was cooled to 0° C. and dicyclohexylcarbodiimide (412 mg, 2.00 mmol) was added. The mixture was then stirred at room temperature overnight (18 h). The mixture was filtered through celite™ (dichloromethane wash) and the filtrate concentrated. The resulting residue was dissolved in ethyl acetate, washed with 0.1M HCl, sat NaHCO$_3$, brine and dried (MgSO$_4$). Concentration and crystallization from ethyl acetate/hexanes gave 451 mg (47%) after filtration and drying to constant weight.

$^1$H NMR (400 MHz, CDCl$_3$) 8.38 ppm (1.7H, d, J=9.0 Hz), 8.24 (0.3H, d, J=9.0 Hz), 7.85 (0.3H, d, J=9.0 Hz), 7.5 (8H, m), 6.91 (1H, d, J=3.9 Hz), 4.95 (1H, bs), 4.43 (2H, b), 1.46/1.44 (9H, app unresolved singlets); MS (DCI-NH$_3$): [M+H]$^+$=499.

Part F—H$_2$N-AMTC-Ox trifluoroacetate salt

To a solution of Boc-AMTC-Ox (200 mg, 0.415 mmol) in dichloromethane (1 mL) was added trifluoroacetic acid (0.5 mL, 6 mmol). The resulting mixture was stirred for 30 min at room temperature, then concentrated and placed under vacuum over NaOH overnight. The oily residue was dissolved in boiling chloroform and filtered hot. The product was then crystallized by adding hexanes to give 189 mg (92%) of the trifluoroacetate salt. $^1$H NMR (400 MHz, DMSO-d$_6$) 8.35 ppm (5H, m), 7.78 (2H, d, J=8.7), 7.57 (6H, m), 7.28 (1H, d J=3.9), 4.28 (2H, s); HRMS (DCI—NH$_3$) calc: 382.0862; found: 382.0872.

Part G—Boc-Asp(Chx)-AMTC-Ox

To a solution of Boc-Asp(Chx)-OH (124 mg, 0.393 mmol) in DMF (1 mL) was added diisopropylethylamine (0.14 mL, 0.80 mmol). To the resulting solution was added TBTU (125 mg, 0.389 mmol), followed by stirring for 2 min and the addition of H$_2$N-AMTC-Ox, trifluoroacetate salt (150 mg, 0.303 mmol). After 4 h at room temperature, the mixture was diluted with ethyl acetate and washed with water (4×), 0.1M HCl, sat NaHCO$_3$, brine and dried (MgSO$_4$). Concentration and drying to constant weight gave 211 mg (100%) of the desired dipeptide. $^1$H NMR (400 MHz, CDCl$_3$): 8.40 ppm (2H, m), 7.5 (8H, m), 7.05 (1H, m), 6.92 (1H, d J=3.7 Hz), 5.65 (1H, bs), 4.74 (1H, m), 4.55 (2H, m), 2.98 (0.4H, d, J=4.6 Hz), 2.94 (0.6H, d, J=4.7 Hz), 2.70 (0.6H, d, J=6.6 Hz), 2.65 (0.4H, d, J=6.6 Hz), 1.5 (20H, m); HRMS (DCI—NH$_3$) calc: 679.2438; found: 679.2439.

Part H—H$_2$N-Asp(Chx)-AMTC-Ox trifluoroacetate salt

To a solution of Boc-Asp(Chx)-AMTC-Ox (211 mg, 0.311 mmol) in dichloromethane (1 mL) was added trifluoroacetic acid (0.5 mL, 6 mmol). The resulting mixture was stirred for 1 h at room temperature, then concentrated. The oily residue was dissolved in boiling chloroform and filtered hot. Concentration and drying to constant weight the gave 221 mg (98%) of the trifluoroacetate salt as a foamy solid. $^1$H NMR (400 MHz, CDCl$_3$) 8.54 ppm (bt,1H,), 8.37 (m, 2H), 7.5 (m, 5H), 7.32 (d, 1H, J=4.0 Hz), 7.17 (m, 2H), 6.85 (d, 1H, J=3.7 Hz), 4.70 (m, 1H), 4.53 (m, 2H), 4.45 (d, 0.6H, J=5.4 Hz), 4.41 (d, 0.4H, J=5.4 Hz), 2.97 (m, 2H), 1.7 (m, 5H), 1.3 (m, 7H); HRMS (DCI—NH$_3$) calc: 579.1913, found: 579.1899.

Part I—Boc-D-Val-MeArg (Tos)-Gly-Asp (Chx)-AMTC-Ox

To a solution of Boc-D-Val-MeArg(Tos)-Gly-OH (191 mg, 0.319 mmol) in DMF (1 mL) was added diisopropylethylamine (0.16 mL, 0.92 mmol). To the resulting solution was added TBTU (102 mg, 0.318 mmol), followed by stirring for 2 min and the addition of H$_2$N-Asp(Chx)-AMTC-Ox, trifluoroacetate salt (221 mg, 0.319 mmol).

After 4 h at room temperature, the mixture was diluted with ethyl acetate and washed with water (4×), 0.1M HCl, sat NaHCO$_3$, brine and dried (MgSO$_4$). Concentration and drying to constant weight gave 260 mg of crude product, which upon purification using flash chromatography (CHCl$_3$–3% MeOH/CHCl$_3$) afforded 220 mg (59%) of the desired pentapeptide. HRMS (FAB) calc: 1159.4593, found: 1159.4577.

Part J—H$_2$N-D-Val-MeArg(Tos)-Gly-Asp(Chx)-AMTC-Ox trifluoroacetate salt

To a solution of Boc-D-Val-MeArg(Tos)-Gly-Asp(Chx)-AMTC-Ox (220 mg, 0.190 mmol) in dichloromethane (1 mL) was added trifluoroacetic acid (0.5 mL, 6 mmol). The resulting mixture was stirred for 30 min at room temperature, then concentrated to give 286 mg of crude product. Purification using flash chromatography (CHCl$_3$–7% MeOH/CHCl$_3$) afforded 152 mg (68%) of the desired trifluoroacetate salt. HRMS (FAB) calc: 1059.4068, found: 1059.4082.

Part K—cyclo-D-Val-MeArg(Tos)-Gly-Asp(Chx)-AMTC

To a solution of H$_2$N-D-Val-MeArg(Tos)-Gly-Asp(Chx)-AMTC-Ox, trifluoroacetate salt (150 mg, 0.128 mmol) in DMF (200 mL) was added diisopropylethylamine (0.18 mL, 1.03 mmol) and acetic acid (0.61 mL, 1.08 mmol). The resulting solution was heated at 60° C. for 20 h, after which time it was cooled to room temperature and the bulk of the DMF distilled at 30° C. (10 mmHg). The concentrated solution of crude product was diluted with ethyl acetate and washed with water (4×), 0.1M HCl, sat NaHCO$_3$ and brine, dried (MgSO$_4$) and concentrated to give 59 mg of crude product. Purification using flash chromatography (3% MeOH/CHCl$_3$) afforded 32 mg (31%) of cyclic peptide. $^1$H NMR (400 MHz, CDCl$_3$, 60° C.) 7.85 ppm (bs, 1H), 7.76 (bs, 1H), 7.70 (d, 2H, J=8.0 Hz), 7.56 (bs, 1H), 7.40 (d, 1H, J=3.4 Hz), 7.18 (d, 2H J=8.0 Hz), 7.03 (bs, 1H), 6.79 (d, 1H, J=3.4 Hz), 6.4 (bs, 3H), 5.22 (bt, 1H), 4.99 (m, 1H), 4.75 (m, 2H), 4.52 (t, 1H, J=9.3 Hz), 4.15 (bd, 1H, J=12.9 Hz), 4.04 (d, 1H, J=15.1 Hz), 3.76 (bd, 1H, J=15.9 Hz), 3.19 (bs, 2H), 2.91 (s, 3H), 2.8 (m, 1H), 2.63 (dd, 1H, J=11.0 Hz, 3.4 Hz), 2.35 (s, 3H), 1.95 (m, 4H), 1.7 (m, 4H), 1.3 (m, 9H), 0.96 (d, 3H, J=6.4 Hz), 0.86 (d, 3H, J =6.1 Hz); HRMS (FAB) calc: 817.3377, found: 817.3375.

Part L—cyclo-D-Val-MeArg-Gly-Asp-AMTC trifluoroacetate salt

Deprotection was carried out using the same procedure as described in Example 1, Part M. From cyclo-D-Val-MeArg(Tos)-Gly-Asp(Chx)-AMTC (32 mg, 0.039 mmol) was obtained 12 mg (46%) of the title compound following HPLC purification; $^1$H-NMR (400 MHz, D$_2$O) 7.40 ppm (d, 1H, J=3.7 Hz), 6.88 (d, 1H, J=3.7 Hz), 5.12 (dd, 1H, J =10.3 Hz, 5.1 Hz), 4.56 (m, overlapped by HOD), 4.31 (d, 1H, J=16.1 Hz), 3.85 (q, 2H, J=14.6 Hz), 3.06 (m, 2H), 2.85 (s, 3H), 2.75 (m, 1H), 2.6 (m, 1H), 2.05 (m, 1H), 1.8 (m, 1H), 1.65 (m, 1H), 1.35 (m, 2H), 0.88 (d, 3H, J=6.6 Hz), 0.79 (d, 3H, J=6.6); HRMS (FAB) calc: 581.2506, found: 581.2516.

Example 3 cyclo(6-(D-Val-NMeArg-Gly-Asp)aminomethyl-2-pyridinecarboxylate);

J=D-Val, K=N(Me)Arg, L=Gly, M=Asp

Part A—6-Bromomethyl-2-pyridinecarboxylic acid, methyl ester 6-methyl-picolinic acid (4.44 g, 32 mmol) was converted to its methyl ester by refluxing with a saturated solution of HCl in dry methanol for 4 hours. After evaporating the solvent, the residue was stirred with methylene chloride and neutralized with NaHCO$_3$. The organic layer was dried over anhydrous sodium sulfate and concentrated to yield 4.44 g (92%) of a yellow oil. $^1$HNMR (CDCl$_3$) 7.95 (d, 1H), 7.75 (t, 1H), 7.35 (d, 1H), 4.00 (s, 3H), 2.65 (s, 3H). MS (NH$_3$—CI) [M+H]$^+$=152. The ester was brominated without further purification.

A solution of methyl ester (1.00 g, 6.6 mmol) and NBS (1.20 g, 6.7 mmol) in CCl$_4$ was refluxed while being irradiated by a 60W tungsten filament lamp. After 3 h, additional NBS (0.60 g, 3.3 mmol) was added and refluxing and irradiation continued for another 3 h. Filtration of the solid, followed by concentration of the filtrate gave a brown residue. Residue was chromatographed to yield 0.56 g (white solid, mp 87°–89° C.) of dibrominated product {$^1$HNMR (CDCl$_3$) 8.15 (d, 1H), 8.10 (d, 1H), 7.95 (t, 1H), 6.75 (s, 1H), 4.00 (s, 3H). MS (NH$_3$—CI) [M+H]$^+$=310, [M+NH$_4$]$^+$=327} and 0.57 g (white solid, mp 68°–70° C.) of the monobrominated product {$^1$HNMR (CDCl$_3$) 8.05 (d, 1H), 7.85 (t, 1H), 7.70 (d, 1H), 4.50 (s, 2H), 4.00 (s, 3H). MS (NH$_3$—CI) [M]$^+$=230}

Part B—6-Azidomethyl-2-pyridinecarboxylic acid, methyl ester

A mixture of 6-bromomethyl-2-pyridinecarboxylic acid, methyl ester 0.50 g, 2.2 mmol) and sodium azide (0.21 g, 3.2 mmol) in DMF was stirred at room temperature overnight. The solvent was evaporated and the residue partitioned between ethyl acetate and water. The organic layer was washed with satd. NaCl, then dried over anhydrous Na$_2$SO$_4$. The solvent was evaporated to yield 0.39 g (93%) of the title compound as a yellow oil. $^1$HNMR (CDCl$_3$) 8.10 (d, 1H), 7.90 (t, 1H), 7.60 (d, 1H), 4.65 (s, 2H), 4.00 (s, 3H). MS (NH$_3$—CI) [M+H]$^+$193.

Part C—6-Aminomethyl-2-pyridinecarboxylic acid, methyl ester (from 6-Azidomethyl-2-pyridinecarboxylic acid, methyl ester)

Azidomethyl compound (0.35 g, 1.8 mmol) was hydrogenated for 1 h in a Parr-hydrogenator, at 32 psi hydrogen pressure, in ethanol containing 1 g of 10% Pd-C as catalyst and conc. HCl (0.33 ml, 2.2 eq.). The catalyst was filtered off and solvent evaporated to yield 0.43 g (100%) of dihydrochloride salt of the title compound as a white solid. $^1$HNMR (CD$_3$OD) 8.25 (d, 1H), 8.15 (t, 1H), 7.80 (d, 1H), 4.45 (s, 2H), 4.10 (s, 3H). MS (NH$_3$—CI) [M+H]$^+$=167.

Part D—6-Formyl-2-pyridinecarboxylic acid, methyl ester

An aqueous soln. of silver nitrate (~8 g, 50 mmol) was added to a soln. of 6-dibromomethyl-2-pyridinecarboxylic acid, methyl ester (1.90 g, 6.1 mmol) in ethanol. The reaction mixture was stirred at 55° C. for a total of 10 h. The rxn. mixture was saturated with sodium chloride and the solid filtered off. The filtrate was concentrated to give a white solid residue which upon chromatography on silica gel gave 0.7 g (70%) of white powder. $^1$HNMR (CDCl$_3$) 10.2 (s, 1H), 8.35 (d, 1H), 8.15 (d, 1H), 8.05 (t, 1H), 4.05 (s, 3H). MS (NH$_3$—CI) [M+H]$^+$=166, [M+NH$_4$]$^+$=183.

Part E—6-Aminomethyl-2-pyridinecarboxylic acid, methyl ester (from 6-Formyl-2-pyridinecarboxylic acid, methyl ester)

Formylpyridine (0.68 g,4.1 mmol) was converted to oxime by refluxing with hydroxylamine hydrochloride (0.68 g, 9.8 mmol) and pyridine (0.8 ml, 9.9 mmol) in ethanol for 16 h. The solvent was evaporated, the residue partitioned between ethyl acetate and water. The organic phase was treated with 10% aqueous citric acid, washed with satd. NaCl soln, then dried over anhydrous Na$_2$SO$_4$. Evaporation of the solvent gave 0.65 g (88%) of a white solid. $^1$HNMR (CDCl$_3$) 8.35 (s, 1H), 8.05 (t, 2H), 7.85 (t, 1H), 4.00(s, 3H). MS (NH$_3$—CI) [M+H]$^+$=181.

The oxime (0.77 g, 4.3 mmol) was was hydrogenated for 0.5 h in a Parr-hydrogenator, at 30 psi hydrogen pressure, in ethanol containing 0.85 g of 10% Pd-C as catalyst and conc. HCl (0.90 ml, 11 mmol). The catalyst was filtered off and solvent evaporated to yield 0.73 g (71%) of dihydrochloride salt of the title compound as a white solid. $^1$HNMR (CD$_3$OD) 8.15 (d, 1H), 8.05 (t, 1H), 7.70 (d, 1H), 4.40 (s, 2H), 4.00 (s, 3H). MS (NH$_3$—CI) [M+H]$^+$=167.

Part F—BOC-Asp(OCHX)-OSu

Dicyclohexylcarbodiimide (3.76 g, 18.3 mmol) was added to a solution of BOC-Asp(OCHX)-OH (5.22 g, 16.6 mmol) and N-hydroxysuccinimide (2.10 g, 18.3 mmol) in ethyl acetate (70 ml)/DMF (5 ml) mixture, at 0° C. The reaction mixture was stirred at 0° C for 1 h then at room temperature overnight. The solid was filtered off and the filtrate washed with 5% NaHCO$_3$ soln. (70 ml×1), water (70 ml×2), and saturated aq. NaCl. The organic phase was dried over anhydrous Na$_2$SO$_4$, then concentrated to give the desired succinimide ester as a white solid in quantitative yield. $^1$HNMR (CDCl$_3$) 5.65 (d, 1H), 5.00 (m, 1H), 4.85 (m, 1H), 3.05 (d of d, 1H), 2.90 (d of d, 1H), 2.80 (s, 4H), 2.00–1.20 (m, 11H), 1.40 (s, 9H). MS (NH$_3$—CI) [M+H]$^+$=413.

Part G—6-(BOC-Asp(OCHX))Aminomethyl-2-pyridinecarboxylic acid

6-Aminomethyl-2-pyridinecarboxylic acid, methyl ester (1.20 g, 5 mmol) was deesterified by treatment with aqueous KOH, followed by acidification with 10% HCl to pH 1. The aqueous soln. was concentrated and the residue stirred with ethanol and filtered. The filtrate upon evaporation and trituration with ether gave 0.80 g (71%) of a yellow solid. $^1$HNMR (CD$_3$OD) 8.2–8.0 (overlapping d of d, 2H), 7.7 (d, 1H), 4.4 (s, 2H).

The amino acid thus obtained (0.74 g, 3.3 mmol) was treated with NaHCO$_3$ (0.84 g, 10 mmol) and BOC-Asp(OCHX)-OSu (1.36 g, 3.3 mmol) in aqueous THF, at room temperature overnight. The reaction mixture was concentrated, then acidified to pH 1.5. The product was extracted in ethyl acetate. After the usual extractive workup, followed by silica gel chromatography 0.91 g (61%) of a white solid was obtained. $^1$HNMR (CDCl3) 8.15 (d, 1H), 7.9 (m, 2H), 7.5 (d, 1H), 5.8 (d, 1H), 4.8 (m, 1H), 4.7 (t, 1H), 4.6 (m, 1H), 3.0 (d of d, 1H), 2.75 (d of d, 1H), 1.9–1.1 (m, 11H), 1.40 (s, 9H). MS (FAB) [M]=449.

Part H—6-(TFA-Asp(OCHX))Aminomethyl-2-pyridinecarboxylic acid

Deprotection of the above BOC-derivative (0.58 g, 1.3 mmol) was carried out by treatment with a 60% TFA-CH$_2$Cl$_2$ soln at room temperature. Evaporation of the solvent followed by trituration with ether gave 0.56 g (93%) of a foamy TFA-salt. $^1$HNMR (CD$_3$OD) 8.1 (d, 1H), 7.95 (t, 1H), 7.60 (d, 1H), 4.8 (m, 1H), 4.6 (s, 2H), 4.35 (d of d, 1H), 3.1 (d of d, 1H), 2.95 (d of d, 1H), 1.9–1.2 (m, 10H). MS (NH$_3$—CI) [M+H]$^+$=350.

Part I—6-(BOC-D-Val-NMeArg(Tos)-Gly-Asp(OCHX))Aminomethyl-2-pyridinecarboxylic acid TFA-salt (0.55 g, 1.2 mmol) was dissolved in 1.5 ml DMF. Diisopropylethylamine was added dropwise, while stirring, to pH 8, followed by the addition of 1 equivalent of BOC-D-Val-NMeArg(Tos)-Gly-OSu (prepared from BOC-D-Val-NMeArg(Tos)-Gly-OH and N-hydroxysuccinimide, by the method described in Part-F). Workup consisted of evaporation of the solvent, addition of 30 ml water, acidification of the soln. to pH 1 and ethyl acetate extraction. The title compound was obtained as a white foamy solid (0.92 g, 99% yield). MS (FAB) [M+H]$^+$=930.

Part J—Cyclo(6-(D-Val-NMeArg(Tos)-Gly-Asp(OCHX))Aminomethyl-2-pyridinecarboxylate)

The BOC-pentapeptide, obtained in the previous step (0.89 g, 1 mmol), was deprotected and converted to its TFA-salt by treatment with 60% TFA—CH$_2$Cl$_2$ soln. Workup, as described in Part-H, gave 0.86 g (96%) of a white solid. MS (FAB) [M+H]$^+$=830.

0.86 g (1 mmol) of the pentapeptide-TFA-salt was stirred with HBTU (0.34 g, 1 mmol) in a 30% DMF/acetonitrile mixture. Diisopropylethylamine (0.50 ml, 2.8 mmol) was added and the rxn. mixture stirred at room temp. overnight. The solvent was evaporated and the residue stirred with ethyl acetate overnight. The resulting solid was filtered and dried to give 0.2 g (27%) of a white powder. MS (FAB) [M+H]$^+$=812.

Part K—Cyclo(6-(D-Val-NMeArg-Gly-Asp) Aminomethyl-2-pyridinecarboxylate).TFA-salt Cyclo(6-(BOC-D-Val-NMeArg(Tos)-Gly-Asp(OCHX)) Aminomethyl-2-pyridinecarboxylate) (0.2 g, 0.25 mmol) was reacted with anhydrous HF at 0° C. for 1h, in the presence of anisole (0.02 ml). The product was precipitated with ethyl ether and filtered. The white residue was dissolved in 10% aqueous acetic acid and lyophilized to give the title compound as a fluffy white solid (0.095 g, 60% calculated as the acetate salt). This product was purified by reversed-phase HPLC on a preparative VYDAC-C18 column (2.5 cm), using a 0.5%/min. gradient of 10–40% acetonitrile/water containing 0.1% TFA. Major fraction (collected at 6–9 min.) was concentrated, residue triturated with acetone and dried to give 0.015 g of the title compound. MS (FAB) [M+H]$^+$=576.

Example 4 cyclo-(D-Val-N(Me)Arg-Gly-Asp-[2-amino]-4-thiazoleacetate);

J=D-Val, K=N(Me)Arg, L=Gly, M=Asp

The title compound was prepared as shown in Scheme 1 below. Treatment of 4-chloroacetoacetate with thiourea in refluxing THF cleanly produced the 2-aminothiazole 1. Protection of the amino functionality and ester saponification gave in high yield the acid 2, ready for incorporation into the cyclic peptide.

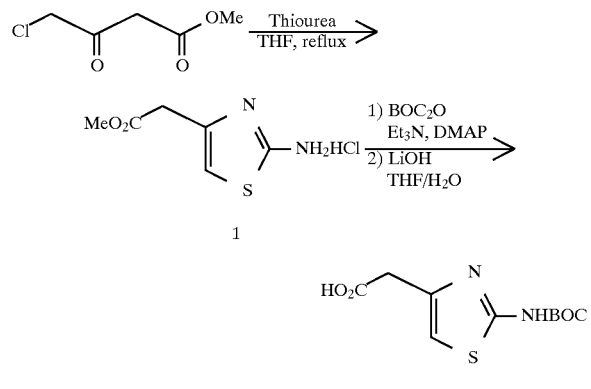

The conversion of 2 into the title compound is shown in Scheme 2 below. DCC-mediated condensation of 2 with 4'-nitro-benzophenone oxime produced the active ester as a mixture of oxime isomers, which upon TFA deprotection gave the amine salt 3. Coupling with BOC-Asp(CHX) followed by TFA deprotection afforded the amine salt 4, which was further coupled with the tripeptide BOC-D-Val-N(Me)Arg(Tos)-Gly to give, after deprotection, the amine salt 5. Cyclization was effected with diisopropylethylamine and acetic acid in CH₃CN to give cyclic peptide XK001 in 40% yield. Final deprotection with HF and HPLC purification produced the desired compound XK002.

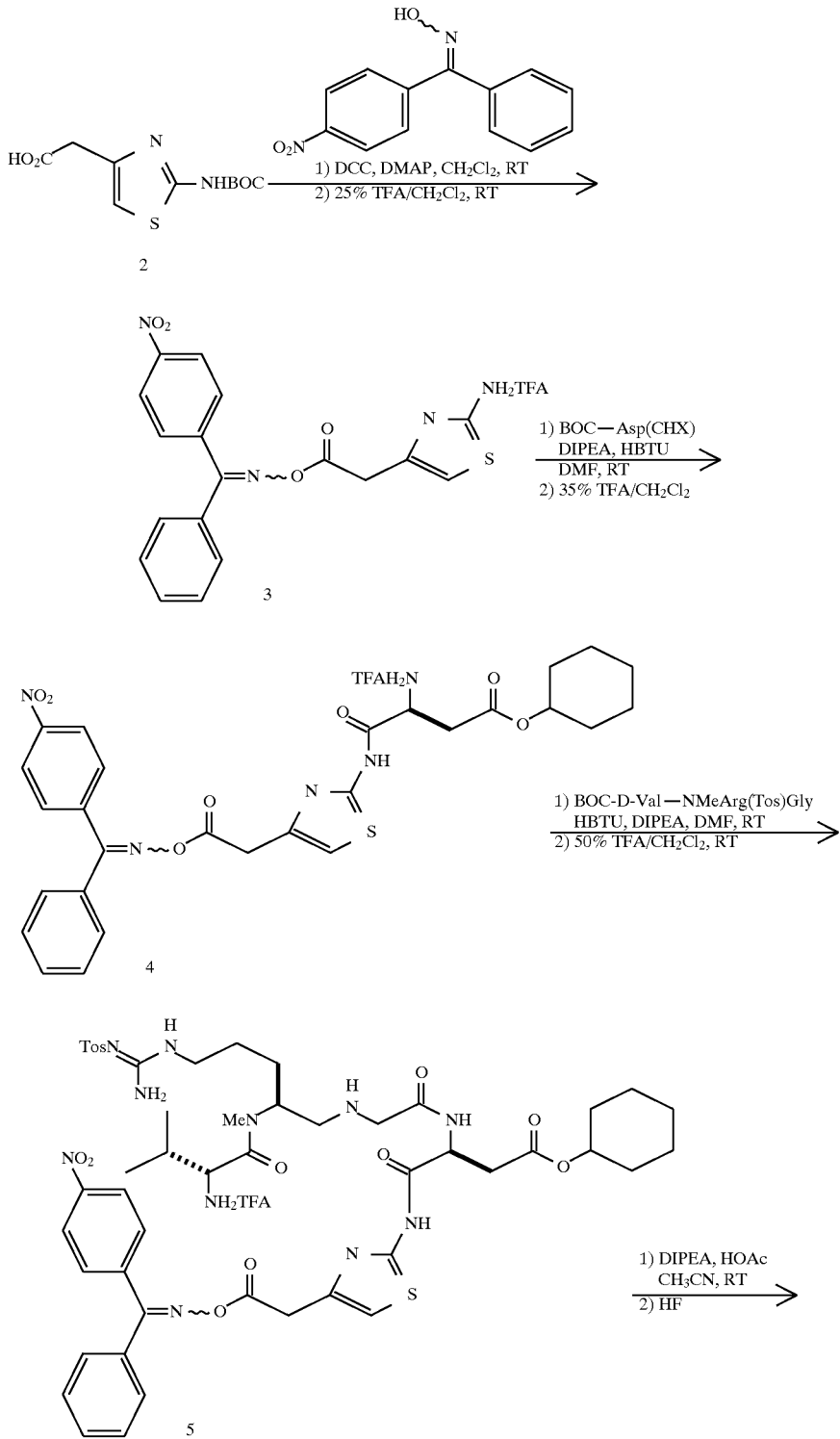

-continued
Scheme 2

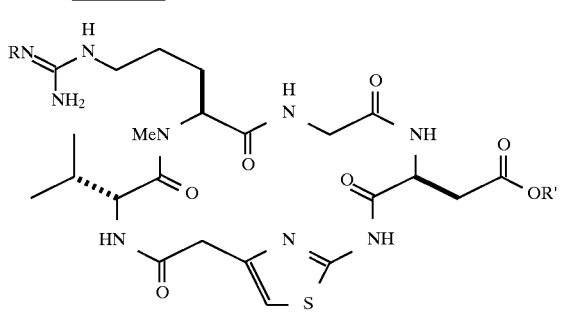

XK001 R = Tos, R' = cyclohexyl
XK002 R = H TFA, R' = H

Methyl 2-amino-4-thiazoleacetate hydrochloride salt (1)

To a solution of methyl 4-chloro-acetoacetate (4.0 g, 27 mmol) in 50 mL of THF was added thiourea (2.0 g, 27 mmol) and the resulting suspension was stirred at reflux for 5 h. The mixture was allowed to cool to room temperature. The white solid was filtered off and washed with ether to afford 5.0 g (90%) of the title compound. $^1$H NMR (D$_2$O) δ6.6 (broad s, 1H), 3.7 (broad s, 2H), 3.6 (broad s, 3H). MS (NH$_3$—CI) 173 (M+H)+(100%).

Methyl 2-(N-tert-butyloxycarbonyl)amino-4-thiazoleacetate

To a solution of methyl 2-amino-4-thiazoleacetate HCl (1) (2.7 g, 12.7 mmol) in 50 mL of methylene chloride at room temperature was added di-tert-butyl dicarbonate (2.8 g, 12.7 mmol), triethylamine (3.9 g, 38.1 mmol) and 4-dimethylaminopyridine (0.4 g, 3.2 mmol). The mixture was allowed to stir overnight and then was concentrated to a syrup. The residue was purified by flash chromatography (elution with 2:1 hexane/ethyl acetate) to afford 3.0 g (86%) of the title compound. $^1$H NMR (CDCl$_3$) δ9.86 (broad s, 1H), 6.76 (s, 1H), 3.77 (s, 2H), 3.71 (s, 3H), 1.55 (s, 9H). MS (NH$_3$—CI) 273 (M+H)+(100%), 217 (58%), 173 (15%).

2-(N-tert-Butyloxycarbonyl)amino-4-thiazoleacetic acid (2)

To a solution of methyl 2-(N-tert-butyloxycarbonyl) amino-4-thiazoleacetate (0.84 g, 3.1 mmol) in 8 mL of 2:1 THF/H$_2$O was added lithium hydroxide (0.26 g, 6.2 mmol). The mixture was allowed to stir at room temperature for 24 h and was then diluted with H$_2$O and ether. The layers were separated and the organic layer was discarded. The aqueous layer was acidified to pH 3 with 1N HCl and extracted with ethyl acetate. The organics were washed with brine, dried (MgSO$_4$) and concentrated to afford the title acid in near quantitative yield. $^1$H NMR (CDCl$_3$) δ6.69 (s,1H), 3.67 (s, 2H), 1.55 (s, 9H). MS (NH$_3$—CI) 259 (M+H)+(57%), 203 (28%), 159 (100%).

4'-Nitrobenzophenimino 2-(N-tert-butyloxycarbonyl) amino-4-thiazoleacetate.

To a solution of methyl 2-(N-tert-butoxycarbonyl)amino-4-thiazoleacetic acid 2 (3.09 g, 12.0 mmol) in 30 mL of methylene chloride at 0° C. was added 4'-nitro-benzophenone oxime (2.63 g, 10.9 mmol), dicyclohexylcarbodiimide (2.24 g, 10.9 mmol) and 4-dimethylaminopyridine (1.33 g, 10.9 mmol). The resulting mixture was allowed to stir at 0° C. for 30 min and then at room temperature for 18 h. The mixture was diluted with ethyl acetate and then washed consecutively with 10% aq HCl, saturated aq NaHCO$_3$, water and brine. The organics were dried (MgSO$_4$) and concentrated to afford the title compound as a mixture of oxime isomers which was used without further purification. $^1$H NMR (CDCl$_3$) δ8.2 (d, 2H), 7.7–7.2 (m, 7H), 6.62 (s, 1H), 3.80 and 3.78 (oxime isomers, s, 2H), 1.54 (s, 9H). MS (NH$_3$—CI) 483 (M+H)+(1%), 227 (100%).

4'-Nitrobenzophenimino 2-amino-4-thiazoleacetate trifluoroacetate salt (3)

To a solution of 4'-nitrobenzophenimino 2-(N-tert-butoxycarbonyl)amino-4-thiazoleacetate (4.6 g, 9.5 mmol) in 21 mL of methylene chloride was added 7 mL of trifluoroacetic acid (25% TFA/CH$_2$Cl$_2$). The solution was allowed to stir for 3 h at room temperature and then was concentrated to an oil. The oil was stirred with methylene chloride and hexane and then concentrated in vacuo to an oily solid (3) which was used without purification. $^1$H NMR (CDCl$_3$) δ 8.6 (broad s, 2H), 8.34 (d, 2H), 8.21 (d, 1H), 7.76 (d,1H), 7.5–7.3 (m, 5H), 6.4 (s, 1H), 3.72 (s, 2H). MS (NH$_3$—CI) 383 (M+H)+(1%).

4'-Nitrobenzophenimino N-(BOC)-Asp(CHX)-2-amino-4-thiazoleacetate

To a solution of BOC-Asp(CHX) (3.34 g, 10.6 mmol) in 10 mL of DMF was added diisopropylethylamine (3.01 g, 23.3 mmol) and HBTU (4.01 g, 10.6 mmol). This solution was stirred for 5 min and then 4'-nitrobenzophenimino 2-amino-4-thiazoleacetate trifluoroacetate salt 3 was added as a solution in 10 mL of DMF. The resulting solution was allowed to stir at room temperature for 18 h whereupon it was diluted with ethyl acetate and washed consecutively with water (twice), 10% aq HCl, saturated aq NaHCO$_3$ and brine. The organics were dried (MgSO$_4$) and concentrated to a solid. The solid was triturated with hexane and dried in vacuo to afford 6.0 g (83%) of the title compound as a yellow powder. $^1$H NMR (CDCl$_3$): consistent with proposed structure. MS (DCI—NH$_3$) 680 (M+H)+(100%).

4'-Nitrobenzophenimino Asp (CHX)-2-amino-4-thiazoleacetate trifluoroacetate salt (4)

To a solution of 4'-nitrobenzophenimino N-(BOC)-Asp (CHX)-2-amino-4-thiazoleacetate in 20 mL of methylene chloride was added 10.5 mL of trifluoroacetic acid (35% TFA/CH$_2$Cl$_2$). This solution was stirred at room temperature for 3 h and then was concentrated in vacuo to a tan solid which was used without purification. $^1$H NMR (CD$_3$OD): consistent with proposed structure. MS(FAB) 580 (M+H)+ (15%), 356 (100%).

4'-Nitrobenzophenimino N-(BOC)-D-Val-N(Me)Arg(Tos)-Gly-Asp(CHX)-2-amino-4-thiazoleacetate To a solution of 4'-nitrobenzophenimino Asp(CHX)-2-amino-4-thiazoleacetate trifluoroacetate salt 4 (1.0 g, 1.44 mmol) in 4 mL of DMF was added BOC-D-Val-N(Me)Arg (Tos)-Gly (0.86 g, 1.44 mmol), HBTU (0.55 g, 1.44 mmol) and diisopropylethylamine (0.56 g, 4.32 mmol). This solution was allowed to stir at room temperature for 18 h whereupon it was diluted with ethyl acetate and washed consecutively with water (twice), 10% aq HCl, saturated aq NaHCO$_3$ and brine. The organics were dried (MgSO$_4$) and concentrated. The residue was purified by flash chromatography (elution with 10:1 EtOAc/MeOH) to afford 1 g (60%) of the title compound as a yellow solid. $^1$H NMR (CDCl$_3$): consistent with proposed structure. MS (FAB) 1161 (M+H)+ (1%), 950.5 (100%).

4'-Nitrobenzophenimino D-Val-N(Me)Arg(Tos)-Gly-Asp (CHX)-2-amino-4-thiazoleacetate trifluoroacetate salt (5)

To a solution of 4'-nitrobenzophenimino N-(BOC)-D-Val-N(Me)Arg(Tos)-Gly-Asp(CHX)-2-amino-4-thiazoleacetate (0.8 g, 0.7 mmol) in 3 mL of methylene chloride was added 3 mL of trifluoroacetic acid (50% TFA/CH$_2$Cl$_2$). This solution was allowed to stir at room temperature for 2 h and then was concentrated in vacuo. The residue was triturated with ether and dried to afford 0.76 g (94%) of the title compound as a yellow solid. $^1$H NMR (CDCl$_3$): consistent with proposed structure. MS (FAB) 1060.4 (M+H)+(35%).

cyclo-(D-Val-N(Me)Arg(Tos)-Gly-Asp(CHX)-2-amino-4-thiazoleacetate) (XK001)

To a solution of 4'-nitrobenzophenimino D-Val-N(Me)Arg(Tos)-Gly-Asp(CHX)-2-amino-4-thiazoleacetate trifluoroacetate salt 5 (0.75 g, 0.64 mmol) in 65 mL of acetonitrile was added diisopropylethylamine (0.33 g, 2.56 mmol) and glacial acetic acid (0.15 g, 2.56 mmol). This solution was allowed to stir at room temperature for 72 h whereupon it was concentrated to an oil and dissolved in 1:1 ethyl acetate/n-butanol. This solution was washed with 10% aq HCl (twice) and brine, dried (MgSO$_4$) and concentrated to an oil. Trituration with ether gave a solid which was taken up in hot ethyl acetate. This mixture was allowed to cool to room temperature and then the solid was filtered and washed with ether to give a yellowish powder which was further purified by HPLC to afford 0.2 g (40%) of the title compound as an off-white solid. $^1$H NMR (DMSO-d6): consistent with proposed structure. MS (NH$_3$—Cl) 818 (M+H)+ (100%), 622 (25%).

cyclo-(D-Val-N(Me)Arg-Gly-Asp-2-amino-4-thiazoleacetate) trifluoroacetate salt (XK002).

The deprotection and HPLC purification was done as described for examples 1,2 and 3. 1H NMR (DMSO-d6): consistent with proposed structure. MS (FAB) 582.4 (M+H)+(100%).

TABLE 3

| Ex. No | R$^{31}$ | J | K | L | M | Platelet Aggregation Assay IC$_{50}$ |
|---|---|---|---|---|---|---|
| 1 | furan-2,5 | D-Val | N—Me—Arg | Gly | Asp | +++ |
| 2 | thiophene-2,5 | D-Val | N—Me—Arg | Gly | Asp | +++ |
| 3 | pyridine-2,6 | D-Val | N—Me—Arg | Gly | Asp | ++ |
| 4 | thiazole-2,5 | D-Val | N—Me—Arg | Gly | Asp | +++ |

In Table 3, +=IC$_{50}$ values of 10–100 uM in the platelet aggregation assay; ++=IC$_{50}$ of 1–10 uM in platelet aggregation assay; +++=IC$_{50}$ of <1 uM in platelet aggregation assay.

Utility

The compounds of this invention possess antiplatelet efficacy, as evidenced by their activity in standard platelet aggregation assays or platelet fibrinogen binding assays, as described below. A compound is considered to be active in these assays if it has an IC$_{50}$ value of less than about 1 mM. Platelet aggregation and fibrinogen binding assays which may used to demonstrate the antiplatelet activity of the compounds of the invention are described below.

Platelet Aggregation Assay

Venous blood was obtained from the arm of a healthy human donor who was drug-free and aspirin-free for at least two weeks prior to blood collection. Blood was collected into 10 ml citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 µl of PRP was added to each micro test tube, and transmittance was set to 0%. 20 µl of various agonists (ADP, collagen, arachidonate, epinephrine, thrombin) were added to each tube, and the aggregation profiles were plotted (% transmittance versus time). The results were expressed as % inhibition of agonist-induced platelet aggregation. For the IC$_{50}$ evaluation, the test compounds were added at various concentrations prior to the activation of the platelets.

Platelet-Fibrinogen Binding Assay

Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets (5×10$^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated, platelets was separated from the free form by centrifugation and then counted on a gamma counter. For an IC$_{50}$ evaluation, the test compounds were added at various concentrations prior to the activation of the platelets.

Dosage and Formulation

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.01 to 50 milligrams per kilogram of body weight.

Dosage forms (compositions) suitable for administration contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

In the present disclosure it should be understood that the specified materials and conditions are important in practicing the invention but that unspecified materials and conditions are not excluded so long as they do not prevent the benefits of the invention from being realized.

What is claimed is:

1. A compound of the formula:

$$\begin{array}{c} \text{(I)} \end{array}$$

or a pharmaceutically acceptable salt form thereof wherein:

$R^1$ is H, $C_1$–$C_4$ alkyl, phenyl, benzyl or phenyl($C_1$–$C_4$) alkyl;

$R^2$ is H or methyl;

$R^{10}$ is H, halogen, $C_1$–$C_8$ alkyl, phenyl or $C_1$–$C_4$ alkoxy;

n' is 0–2;

n" is 0–1;

$R^{31}$ is a 5 or 6 membered aromatic heterocycle, said heterocycle being substituted with 0–2 $R^{10}$, said heterocycle being selected from the group consisting of: furan, thiophene, pyrrole, imidazole, pyrazole, oxazole, isoxazole, thiazole, isothiazole, 1,2,4-triazole, 1,2,4-oxazole, 1,3,4-oxazole, 1,2,4-thiazole, 1,3,4thiazole, pyridine, pyridazine, pyrimidine, pyrazine, 1,2,3-, 1,2,4- and 1,3,5-triazine;

J is D-Ala, D-Val, D-Ile, D-Leu, D-Nle, Gly, D-phenylGly, D-Phe, Phe, D-Lys, D-Orn, D-Met, D-Pro, Pro, Ala, b-Ala, D-Tyr, D-Ser, N-MeGly, D-cyclohexyGly, D-cyclohexylmethylGly, D-norvaline, D-2-aminobutyric acid, D2-aminopentanoic acid, $N^e$-benzoyl-D-Lys, Val, Lys, or Ser;

K is aNMeArg, Arg, or P-guanidinylPhe;

L is Gly; and

M is selected from Asp, b-MeAsp, and NMeAsp.

2. A compound of claim 1 or a pharmaceutically acceptable salt form thereof, of the formula (II):

$$\begin{array}{c} \text{(II)} \end{array}$$

wherein:

$R^1$ is H, $C_1$–$C_4$ alkyl, phenyl, benzyl or phenyl($C_1$–$C_4$) alkyl;

$R^2$ is H or methyl;

$R^{10}$ is H, halogen, $C_1$–$C_8$ alkyl, phenyl or $C_1$–$C_4$ alkoxy;

$R^{31}$ is a 5 or 6 membered aromatic heterocycle, said heterocycle being substituted with 0–2 $R^{10}$, said heterocycle being selected from the group consisting of:

furan, thiophene, pyrrole, imidazole, pyrazole, oxazole, isoxazole, thiazole, isothiazole, 1,2,4-triazole, 1,2,4-oxazole, 1,3,4oxazole, 1,2,4-thiazole, 1,3,4-thiazole, pyridine, pyridazine, pyrimidine, pyrazine, 1,2,3-, 1,2,4- and 1,3,5-triazine.

J is D-Ala, D-Val, D-Ile, D-Leu, D-Nle, Gly, D-phenylGly, D-Phe, Phe, D-Lys, D-Orn, D-Met, D-Pro, Pro, Ala, b-Ala, D-Tyr, D-Ser, N-MeGly, D-cyclohexylGly, D-cyclohexylmethylGly, D-norvaline, D-2-aminobutyric acid, D-2-aminopentanoic acid, $N^e$-benzoyl-D-Lys, Val, Lys, or Ser;

K is aNMeArg, Arg, or P-guanidinylPhe;

L is Gly; and

M is selected from Asp, b-MeAsp, and NMeAsp.

3. A compound of claim 2 or a pharmaceutically acceptable salt form thereof, wherein:

$R^1$ is H or $C_1$–$C_4$ alkyl;

$R^2$ is H or methyl;

$R^{10}$ is H or halogen;

$R^{31}$ is a 5 or 6 membered aromatic heterocycle, said heterocycle being substituted with 0–2 $R^{10}$, said heterocycle being selected from the group consisting of: furan, thiophene, pyrrole, imidazole, pyrazole, oxazole, isoxazole, thiazole, isothiazole, 1,2,4-triazole, 1,2, 4oxazole, 1,3,4-oxazole, 1,2,4-thiazole, 1,3,4-thiazole, pyridine, pyridazine, pyrimidine, pyrazine, 1,2,3-, 1,2,4- and 1,3,5-triazine;

J is D-Ala, D-Val, D-Ile, D-Leu, D-Nle, Gly, D-phenylGly, D-Phe, Phe, D-Lys, D-Orn, D-Met, D-Pro, Pro, Ala, b-Ala, D-Tyr, D-Ser, N-MeGly, D-cyclohexylGly, D-cyclohexylmethylGly, D-norvaline, D-2-aminobutyric acid, D-2-aminopentanoic acid, $N^e$-benzoyl-D-Lys, Val, Lys, or Ser;

K is aNMeArg, Arg, or P-guanidinylPhe;

L is Gly; and

M is selected from Asp, b-MeAsp, and NMeAsp.

4. A compound of claim 3 or a pharmaceutically acceptable salt form thereof, wherein:

$R^1$ and $R^2$ are independently selected from H or methyl;

$R^{10}$ is H or halogen;

$R^{31}$ is a 5 or 6 membered aromatic heterocycle, said heterocycle being substituted with 0–2 $R^{10}$, said heterocycle being selected from the group consisting of:
2,5-furan, 2,5-thiophene, 2,5-pyrrole, 2,5-imidazole, 3,5-pyrazole, 2,5-oxazole, 3,5-isoxazole, 2,5-thiazole, 3,5-isothiazole, 2,6-pyridine, 2,6-pyridazine, 2,4-pyrimidine, and 3,5-pyrazine;

J is selected from D-Val, D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala;

K is αNMeArg;

L is Gly;

M is selected from Asp; β-MeAsp, and NMeAsp.

5. A method for the treatment of thrombosis which comprises administering to a host in need of such treatment a therapeutically effective amount of a compound of claim 1.

6. A method for the treatment of thrombosis which comprises administering to a host in need of such treatment a therapeutically effective amount of a compound of claim 2.

7. A method for the treatment of thrombosis which comprises administering to a host in need of such treatment a therapeutically effective amount of a compound of claim 3.

8. A method for the treatment of thrombosis which comprises administering to a host in need of such treatment a therapeutically effective amount of a compound of claim 4.

9. A pharmaceutical composition comprising a compound of claim 1 and a pharmaceutically acceptable carrier.

10. A pharmaceutical composition comprising a compound of claim 2 and a pharmaceutically acceptable carrier.

11. A pharmaceutical composition comprising a compound of claim 3 and a pharmaceutically acceptable carrier.

12. A pharmaceutical composition comprising a compound of claim 4 and a pharmaceutically acceptable carrier.

* * * * *